US011697843B2

(12) United States Patent
Schroeder et al.

(10) Patent No.: US 11,697,843 B2
(45) Date of Patent: *Jul. 11, 2023

(54) METHODS FOR CREATING DIRECTIONAL BISULFITE-CONVERTED NUCLEIC ACID LIBRARIES FOR NEXT GENERATION SEQUENCING

(71) Applicant: Tecan Genomics, Inc., Redwood City, CA (US)

(72) Inventors: Benjamin G. Schroeder, San Mateo, CA (US); Doug Amorese, Los Altos, CA (US)

(73) Assignee: Tecan Genomics, Inc., Redwood City, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 17/321,030

(22) Filed: May 14, 2021

(65) Prior Publication Data

US 2021/0285040 A1    Sep. 16, 2021

Related U.S. Application Data

(63) Continuation of application No. 14/991,340, filed on Jan. 8, 2016, now Pat. No. 11,028,430, which is a continuation of application No. 13/938,059, filed on Jul. 9, 2013, now abandoned.

(60) Provisional application No. 61/801,382, filed on Mar. 15, 2013, provisional application No. 61/669,613, filed on Jul. 9, 2012.

(51) Int. Cl.
  *C12Q 1/6858*    (2018.01)
  *C12Q 1/6855*    (2018.01)

(52) U.S. Cl.
  CPC ......... *C12Q 1/6858* (2013.01); *C12Q 1/6855* (2013.01)

(58) Field of Classification Search
  CPC . C12Q 1/6855; C12Q 1/6858; C12N 15/1093
  See application file for complete search history.

(56) References Cited

U.S. PATENT DOCUMENTS

| | | |
|---|---|---|
| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,728,775 A | 3/1988 | Van Straten |
| 4,876,187 A | 10/1989 | Duck et al. |
| 4,925,065 A | 5/1990 | Golias |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,312,757 A | 5/1994 | Matsuyama et al. |
| 5,384,242 A | 1/1995 | Oakes |
| 5,386,023 A | 1/1995 | Sanghvi et al. |
| 5,399,491 A | 3/1995 | Kacian et al. |
| 5,409,818 A | 4/1995 | Davey et al. |
| 5,418,149 A | 5/1995 | Gelfand et al. |
| 5,422,271 A | 6/1995 | Chen et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |

(Continued)

FOREIGN PATENT DOCUMENTS

| | | |
|---|---|---|
| CA | 2444926 A1 | 11/2002 |
| CN | 1661102 A | 8/2005 |

(Continued)

OTHER PUBLICATIONS

Margulies et al.(Nature 437.7057 (2005): 376-380; cited in IDS filed Dec. 10, 2021) (Year: 2005).*
Merriman, 2012, Progress in Ion Torrent semiconductor chip based sequencing, Electrophoresis, 35(23):3397-3417.
Miner, 2004, Molecular barcodes detect redundancy and contamination in hairpin-bisulfite PCR, Nucl Acids Res 32 (17):e135, 4 pages.
Morlan, 2012, Selective depletion of rRNA enables whole transcriptome profiling of archival fixed tissue, PLoSOne 7(8):e42882.
Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).

(Continued)

*Primary Examiner* — Sahana S Kaup
(74) *Attorney, Agent, or Firm* — Brown Rudnick LLP; Adam M. Schoen

(57) ABSTRACT

Provided herein are methods, compositions and kits for the generation of bisulfite-converted next generation sequencing (NGS) libraries. The methods, compositions and kits provided herein can be useful, for example, for the production of libraries from genomic DNA that allow for determination of the methylation status across the genome, i.e. the methylome. The methods, compositions and kits provided herein can also be utilized to query methylation status at a particular genomic locus or loci. Moreover, the methods provided herein can be employed for high-throughput sequencing of bisulfite-converted DNA while maintaining the directional (strandedness) information of the original nucleic acid sample.

20 Claims, 2 Drawing Sheets

Specification includes a Sequence Listing.

(56) References Cited

U.S. PATENT DOCUMENTS

| | | |
|---|---|---|
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissman et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Burg et al. |
| 6,107,023 A | 8/2000 | Reyes et al. |
| 6,110,709 A | 8/2000 | Ausubel et al. |
| 6,150,112 A | 11/2000 | Weissman et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,180,338 B1 | 1/2001 | Adams |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Macevicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Lukhtanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissman et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner et al. |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil Lastrucci |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B2 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,704,687 B2 | 4/2010 | Wang et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn |
| 7,846,733 B2 | 12/2010 | Kurn |

(56) References Cited

U.S. PATENT DOCUMENTS

| | | |
|---|---|---|
| 7,867,703 B2 | 1/2011 | Sampson et al. |
| 7,914,162 B1 | 3/2011 | Huang |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,209,130 B1 | 6/2012 | Kennedy et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 9,248,076 B2 | 2/2016 | Sullivan et al. |
| 9,546,399 B2 | 1/2017 | Amorese et al. |
| 9,650,628 B2 | 5/2017 | Amorese et al. |
| 9,702,004 B2 | 7/2017 | Van Eijk et al. |
| 9,745,627 B2 | 8/2017 | van Eijk et al. |
| 9,896,721 B2 | 2/2018 | Van Eijk et al. |
| 9,920,366 B2 | 3/2018 | Eltoukhy et al. |
| 10,036,012 B2 | 7/2018 | Amorese et al. |
| 10,102,337 B2 | 10/2018 | Scolnick et al. |
| 10,415,089 B2 | 9/2019 | Rava et al. |
| 10,457,995 B2 | 10/2019 | Falasaz |
| 10,570,451 B2 | 2/2020 | Salk et al. |
| 10,704,086 B2 | 7/2020 | Talasaz et al. |
| 10,738,364 B2 | 8/2020 | Talasaz |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weismann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197611 A1 | 12/2002 | Chagovetz |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0049861 A1 | 3/2003 | Woodward |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0211616 A1 | 11/2003 | Leong |
| 2003/0213905 A1 | 11/2003 | Lennon et al. |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquin et al. |
| 2004/0005614 A1 | 1/2004 | Kurn et al. |
| 2004/0022689 A1 | 2/2004 | Wulf et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064414 A1 | 3/2005 | Hanna |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0134633 A1 | 6/2006 | Chen et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0285430 A1 | 12/2006 | Seto |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224607 A1 | 9/2007 | Morgan et al. |
| 2007/0224613 A1 | 9/2007 | Strathmann |
| 2007/0231823 A1 | 10/2007 | McKernan et al. |
| 2007/0238122 A1 | 10/2007 | Mlbritton et al. |
| 2007/0263045 A1 | 11/2007 | Okazawa |
| 2008/0038727 A1 | 2/2008 | Spier |
| 2008/0087826 A1 | 4/2008 | Harris et al. |
| 2008/0103058 A1 | 5/2008 | Siddiqi |
| 2008/0131937 A1 | 6/2008 | Schroeder |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0217246 A1 | 9/2008 | Benn et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0123923 A1 | 5/2009 | Yamamoto et al. |
| 2009/0124514 A1 | 5/2009 | Fu et al. |
| 2009/0127589 A1 | 5/2009 | Rothberg et al. |
| 2009/0130721 A1 | 5/2009 | Kurn et al. |
| 2009/0148842 A1* | 6/2009 | Gormley ............. C12Q 1/6809 435/6.12 |
| 2009/0191566 A1 | 7/2009 | McKernan et al. |
| 2009/0203085 A1 | 8/2009 | Kurn et al. |
| 2009/0203531 A1 | 8/2009 | Kurn |
| 2009/0233802 A1 | 9/2009 | Bignell et al. |
| 2009/0233804 A1 | 9/2009 | Kurn et al. |
| 2009/0239232 A1 | 9/2009 | Kurn |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |

(56) References Cited

U.S. PATENT DOCUMENTS

| | | |
|---|---|---|
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0069250 A1 | 3/2010 | White, III et al. |
| 2010/0081174 A1* | 4/2010 | Dunn .................. C12Q 1/6827 435/91.1 |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0267043 A1 | 10/2010 | Braverman et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0009276 A1 | 1/2011 | Vermaas et al. |
| 2011/0015096 A1 | 1/2011 | Chiu |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0186466 A1 | 8/2011 | Kurowski et al. |
| 2011/0189679 A1 | 8/2011 | Kurn et al. |
| 2011/0203688 A1 | 8/2011 | Reed et al. |
| 2011/0224105 A1 | 9/2011 | Kurn et al. |
| 2011/0288780 A1 | 11/2011 | Rabinowitz et al. |
| 2011/0294132 A1 | 12/2011 | Kurn |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0107811 A1 | 5/2012 | Kelso et al. |
| 2012/0122701 A1 | 5/2012 | Ryan et al. |
| 2012/0149068 A1 | 6/2012 | Kurn |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0208705 A1 | 8/2012 | Steemers et al. |
| 2012/0220479 A1 | 8/2012 | Ericsson et al. |
| 2012/0220483 A1 | 8/2012 | Kurn et al. |
| 2012/0220494 A1 | 8/2012 | Samuels et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0252682 A1 | 10/2012 | Zhou et al. |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2012/0328487 A1 | 12/2012 | Saito et al. |
| 2013/0005585 A1 | 1/2013 | Anderson et al. |
| 2013/0059738 A1 | 3/2013 | Leamon et al. |
| 2013/0072390 A1 | 3/2013 | Wang et al. |
| 2013/0137582 A1 | 5/2013 | Ong et al. |
| 2013/0231253 A1 | 9/2013 | Amorese et al. |
| 2014/0031240 A1 | 1/2014 | Behlke et al. |
| 2014/0038188 A1 | 2/2014 | Kurn |
| 2014/0038236 A1 | 2/2014 | Kurn et al. |
| 2014/0051585 A1 | 2/2014 | Prosen et al. |
| 2014/0065692 A1 | 3/2014 | Kurn et al. |
| 2014/0186827 A1 | 7/2014 | Pieprzyk et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0274741 A1 | 9/2014 | Hunter et al. |
| 2014/0303000 A1 | 10/2014 | Armour |
| 2014/0378345 A1 | 12/2014 | Hindson et al. |
| 2015/0004600 A1 | 1/2015 | Wang et al. |
| 2015/0011396 A1 | 1/2015 | Schroeder et al. |
| 2015/0017635 A1 | 1/2015 | Myllykangas et al. |
| 2015/0037790 A1 | 2/2015 | Fox et al. |
| 2015/0101595 A1 | 4/2015 | Hancock et al. |
| 2015/0111208 A1 | 4/2015 | Umbarger et al. |
| 2015/0133319 A1 | 5/2015 | Fu et al. |
| 2015/0151300 A1 | 6/2015 | Williams et al. |
| 2015/0190802 A1 | 7/2015 | Oppenheimer et al. |
| 2015/0218620 A1 | 8/2015 | Behlke et al. |
| 2015/0284769 A1 | 10/2015 | Schroeder |
| 2015/0299767 A1 | 10/2015 | Armour et al. |
| 2015/0299784 A1 | 10/2015 | Fan et al. |
| 2015/0299812 A1 | 10/2015 | Talasaz |
| 2016/0016140 A1 | 1/2016 | Jovanovich et al. |
| 2016/0068889 A1 | 3/2016 | Gole et al. |
| 2016/0122756 A1 | 5/2016 | Armour |
| 2016/0130576 A1 | 5/2016 | Armour |
| 2016/0153039 A1 | 6/2016 | Amorese et al. |
| 2016/0203259 A1 | 7/2016 | Scolnick et al. |
| 2016/0220994 A1 | 8/2016 | Wright |
| 2016/0251711 A1 | 9/2016 | Amorese et al. |
| 2016/0265042 A1 | 9/2016 | Schroeder et al. |
| 2016/0275240 A1 | 9/2016 | Elga et al. |
| 2016/0296930 A1 | 10/2016 | Matear et al. |
| 2017/0356053 A1 | 12/2017 | Otto et al. |
| 2018/0127817 A1 | 5/2018 | Borchert et al. |
| 2018/0216174 A1 | 8/2018 | Shum et al. |
| 2018/0346977 A1 | 12/2018 | Alt et al. |

FOREIGN PATENT DOCUMENTS

| | | |
|---|---|---|
| CN | 101565746 A | 10/2009 |
| CN | 105890722 A | 8/2016 |
| EP | 0365627 B1 | 12/1993 |
| EP | 0329822 B1 | 6/1994 |
| EP | 0667393 A2 | 8/1995 |
| EP | 1071811 B1 | 3/2002 |
| EP | 0843735 B1 | 7/2002 |
| EP | 1362788 A2 | 11/2003 |
| EP | 2186563 A2 | 5/2010 |
| EP | 2192186 A1 | 6/2010 |
| EP | 2272976 A1 | 1/2011 |
| EP | 2322612 A1 | 5/2011 |
| EP | 2451973 A1 | 5/2012 |
| EP | 2511381 A1 | 10/2012 |
| EP | 2538228 A2 | 12/2012 |
| EP | 2599879 A1 | 6/2013 |
| EP | 1929039 B2 | 11/2013 |
| JP | 2015511819 A | 4/2015 |
| WO | 89/09284 A1 | 10/1989 |
| WO | 90/06044 A2 | 6/1990 |
| WO | 92/07951 A1 | 5/1992 |
| WO | 93/18052 A1 | 9/1993 |
| WO | 94/16090 A1 | 7/1994 |
| WO | 96/40998 A1 | 12/1996 |
| WO | 97/12061 A1 | 4/1997 |
| WO | 97/25416 A2 | 7/1997 |
| WO | 98/06736 A1 | 2/1998 |
| WO | 98/38296 A1 | 9/1998 |
| WO | 98/044151 A1 | 10/1998 |
| WO | 99/10540 A1 | 3/1999 |
| WO | 99/11819 A1 | 3/1999 |
| WO | 99/42618 A1 | 8/1999 |
| WO | 00/08208 A2 | 2/2000 |
| WO | 2000/09756 A1 | 2/2000 |
| WO | 00/018957 A1 | 4/2000 |
| WO | 00/39345 A1 | 7/2000 |
| WO | 2000/043531 A2 | 7/2000 |
| WO | 00/52191 A1 | 9/2000 |
| WO | 2000/55364 A2 | 9/2000 |
| WO | 00/70039 A1 | 11/2000 |
| WO | 01/20035 A2 | 3/2001 |
| WO | 01/23613 A1 | 4/2001 |
| WO | 01/46464 A1 | 6/2001 |
| WO | 01/57248 A2 | 8/2001 |
| WO | 01/64952 A2 | 9/2001 |
| WO | 02/00938 A2 | 1/2002 |
| WO | 02/28876 A2 | 4/2002 |
| WO | 02/29117 A2 | 4/2002 |
| WO | 02/36821 A2 | 5/2002 |

(56) References Cited

FOREIGN PATENT DOCUMENTS

| | | |
|---|---|---|
| WO | 02/48402 A2 | 6/2002 |
| WO | 02/060318 A2 | 8/2002 |
| WO | 02/072772 A2 | 9/2002 |
| WO | 02/072773 A2 | 9/2002 |
| WO | 02/081753 A1 | 10/2002 |
| WO | 02/090584 A2 | 11/2002 |
| WO | 03/004690 A2 | 1/2003 |
| WO | 2003/002736 A2 | 1/2003 |
| WO | 2003/012118 A1 | 2/2003 |
| WO | 03/022438 A1 | 3/2003 |
| WO | 03/027259 A2 | 4/2003 |
| WO | 03/078645 A2 | 9/2003 |
| WO | 03/083435 A2 | 10/2003 |
| WO | 03/106642 A2 | 12/2003 |
| WO | 04/011665 A2 | 2/2004 |
| WO | 2004/070007 A2 | 8/2004 |
| WO | 2004/092418 A2 | 10/2004 |
| WO | 2005/003375 A2 | 1/2005 |
| WO | 2005/003381 A1 | 1/2005 |
| WO | 2005/038427 A2 | 4/2005 |
| WO | 2005/065321 A2 | 7/2005 |
| WO | 2006/081222 A2 | 8/2006 |
| WO | 2006/086668 A2 | 8/2006 |
| WO | 2006/137733 A1 | 12/2006 |
| WO | 2007/018601 A1 | 2/2007 |
| WO | 2007/019444 A2 | 2/2007 |
| WO | 2007/030759 A2 | 3/2007 |
| WO | 2007/037678 A2 | 4/2007 |
| WO | 2007/052006 A1 | 5/2007 |
| WO | 2007/057652 A1 | 5/2007 |
| WO | 2007/073165 A1 | 6/2007 |
| WO | 2007/136717 A1 | 11/2007 |
| WO | 2008/005459 A2 | 1/2008 |
| WO | 2008/015396 A2 | 2/2008 |
| WO | 2008/033442 A2 | 3/2008 |
| WO | 2008/093098 A2 | 8/2008 |
| WO | 2008/115185 A2 | 9/2008 |
| WO | 2008150432 A1 | 12/2008 |
| WO | 2009/053039 A1 | 4/2009 |
| WO | 2009/102878 A2 | 8/2009 |
| WO | 2009/102896 A2 | 8/2009 |
| WO | 2009/112844 A1 | 9/2009 |
| WO | 2009/117698 A2 | 9/2009 |
| WO | 2009/120372 A2 | 10/2009 |
| WO | 2009/120374 A2 | 10/2009 |
| WO | 2010/003153 A2 | 1/2010 |
| WO | WO-2010003153 A2 * | 1/2010 ........... C12Q 1/6827 |
| WO | 2010/030683 A1 | 3/2010 |
| WO | 2010/039991 A2 | 4/2010 |
| WO | 2010/063711 A1 | 6/2010 |
| WO | 2010/064893 A1 | 6/2010 |
| WO | 2010/085715 A1 | 7/2010 |
| WO | 2010/091246 A2 | 8/2010 |
| WO | 2010/115154 A1 | 10/2010 |
| WO | 2010/129937 A2 | 11/2010 |
| WO | 2011/003630 A1 | 1/2011 |
| WO | 2011/009941 A1 | 1/2011 |
| WO | 2011/019964 A1 | 2/2011 |
| WO | 2011/032053 A1 | 3/2011 |
| WO | 2011032040 A1 | 3/2011 |
| WO | 2011/053987 A1 | 5/2011 |
| WO | 2011/151777 A1 | 12/2011 |
| WO | 2011/156529 A2 | 12/2011 |
| WO | 2012/013932 A2 | 2/2012 |
| WO | 2012/061832 A1 | 5/2012 |
| WO | 2012/054873 A3 | 8/2012 |
| WO | 2012/103154 A1 | 8/2012 |
| WO | 2013/059740 A1 | 4/2013 |
| WO | 2013/059746 A1 | 4/2013 |
| WO | 2013/112923 A1 | 8/2013 |
| WO | 2013/130674 A1 | 9/2013 |
| WO | 2013/130512 A3 | 10/2013 |
| WO | 2013/177220 A1 | 11/2013 |
| WO | 2013/190441 A2 | 12/2013 |
| WO | 2013/191775 A2 | 12/2013 |
| WO | 2014/028778 A1 | 2/2014 |
| WO | 2014/039556 A1 | 3/2014 |
| WO | 2014/082032 A1 | 5/2014 |
| WO | 2013/138510 A9 | 7/2014 |
| WO | 2014/144092 A1 | 9/2014 |
| WO | 2014/150931 A1 | 9/2014 |
| WO | 2015/031691 A1 | 3/2015 |
| WO | 2015/073711 A1 | 5/2015 |
| WO | 2015104302 A1 | 7/2015 |
| WO | 2015/131107 A1 | 9/2015 |
| WO | 2016/040476 A1 | 3/2016 |
| WO | 2018/102783 A1 | 6/2018 |
| WO | 2019/079724 A1 | 4/2019 |
| WO | 2019/104337 A1 | 5/2019 |

OTHER PUBLICATIONS

Mühlberger, 2011, Compputational Analysis Workflows for Omics Data Interpretation, In: Mayer B. (eds) Bioinformatics for Omics Data, Methods in Molecular Biology (Methods and Protocols), vol. 719, pp. 379-397, Chapter 17, Humana Press.

Nugen, 2014, User Guide Ovation Target Enrichment System, NuGEN Technologies Inc., San Carlos, CA (45 pages).

Nugen, 2016, Ovation RNA-Seq User Guide, NuGEN Technologies, Inc., San Carlos, CA (42 pages).

Plagnol, 2012, A robust model for read count data in exome sequencing experiments and implications for copy number variant calling, Bioinformatics 28(21):2747-2754.

Qiu, 2003, DNA sequence-based "bar-codes" for tracking the origins of expressed sequence tags from a maize cDNA library constructed using multiple mRNA sources, Plant Physiol 133:475-481.

Querfurth, 2012, Creation and application of immortalized bait libraries for targeted enrichment and next-generation sequencing, Biotechniques 52(6):375-380.

Ramsahoye, 2000, Non-CpG methylation is prevalent in embryonic stem cells and may be mediated by DNA methyltransferase 3a, Proc Natl Acad Sci USA, 97(10):5237-5242.

Ronaghi, 2001, Pyrosequencing sheds light on DNA sequencing, Genome Res 11:3-11.

Rothberg, 2011, An integrated semiconductor device enabling non-optical genome sequencing, Nature 475 (7356):348-352.

Sambrook, 2005, Mapping RNA with nuclease S1, Nat Meth 2:397-398.

Sathirapongsasuti, 2011, Exome sequencing-based copy-number variation and loss of heterozygosity detection: ExomeCNV, Bioinformatics 27(19):2648-2654.

Schiemer, 2011, Illumina TruSeq Adapters Demystified,TUFTS University Core Facility XP055357867 (5 pages).

Shapero, 2001, SNP Genotyping by multiplexed solid-phase amplification and fluorescent minisequencing, Genome Res 11:1926-1934.

Shendure, 2005, Accurate multiplex polony sequencing of an evolved bacterial genome, Science 309:1728.

Shiroguchi, 2012, Digital RNA sequencing minimizes sequence dependent bias and amplification noise with optimized single-molecule barcodes, PNAS, 109(4):1347-1352 and Supplemental Information, 22 pages.

Smith, 2010, Highly-multiplexed barcode sequencing: an efficient method for parallel analysis of pooled samples, Nucleic Acids Research, 38(13):e142, 7 pages.

Soni, 2007, Progress toward ultrafast DNA sequencing using solid-state nanopores, Clin Chem 53(11):1996-2001.

Sood, 2006, Methods for reverse genetic screening in zebrafish by resequencing and Tilling, Methods 39:220-227.

Staroscik, 2004, Calculator for determining the number of copies of a template, URI Genomics, webpage archive dated Apr. 6, 2017 (1 page), Retrieved from the internet on Mar. 7, 2018, from <https://web.archive.org/web/20170406174850/http://cels.uri.edu/gsc/cndna.html>.

Steffens, 2017, A versatile and low-cost open source pipetting robot for automation of toxicological and ecotoxicological bioassays, PLoS One 12(6):e0179636.

(56) References Cited

OTHER PUBLICATIONS

Stratagene, 1998, Gene characterization kits, Stratagene Catalog, p. 39 (2 pages).
Supplementary European search report and opinion dated Jan. 30, 2018, for European patent application No. 15830393.3 (6 pages).
Tewhey, 2009, Micrdroplet-based PCR enrichment for large-scali targeted sequencing, Nat Biotech 27(11):1025-1031.
The Ovation Ullralow System V2 User guide, part No. 0344, 0344NB, file name M01379_v5_User_Guide__Ovation_Ultralow_Library_Systems_V2_(Part_No.0344)_2215.pdf, available from nugen.com from NuGEN Technologies Inc., San Carlos, CA (30 pages).
Fill, 2003, Large-scale discovery of induced point mutations with high-throughput Tilling, Genome Res 13:524-530.
Torri, 2012, Next generation sequence analysis and computational genomics using graphical pipeline workflows, Genes, vol. 3, pp. 545-575.
Trapnell, 2010, Transcript assembly and quantification by RNA-Seq reveals unannotated transcripts and isoform switching during cell differentiation, Nat Biotech 28:511-515.
Trapnell, 2013, Differential analysis of gene regulation at transcript resolution with RNA-seq, Nat Biotech 31:46-53.
Truseq Nano DNA Library Prep guide, file name truseq-nano-dna-library-prep-guide-15041110-d.pdf, available from support.illumina.com, Illumina, Inc., San Diego, CA (40 pages).
Tucker, 2009, Massively parallel sequencing: the next big thing in genetic medicine, Am J Human Genet 85:142-154.
Unemo, 2004, Molecular typing of Neisseria gonorrhoeae isolates by pyrosequencing of highly polymorphic segments of the porB gene, J Clin Microb 42(7):2926-2934.
Van der Auwera, 2013, From FastQ data to high confidence variant calls, the Genome Analysis Toolkit Best Practices Pipeline, Current Protocols in Bioinformatics 11.10.1-11.10.33, WileyOnlineLibrary.com, 33 pages.
Vigal, 2002, A review on SNP and other types of molecular markers and their use in animal genetics, Genet Sel Evol 34:275-305.
Wagle, 2012, High-Throughput detection of actionable genomic alterations in clinical tumor samples by targeted massively parallel sequencing, Cancer Discovery, 2(1):82-93.
Walker, 1992, Strand displacement amplification—an isothermal, in vitro DNA amplification technique, Nucl Acids Res 20(7):1691-1696.
Westin 2000, Anchored multiplex amplification on a microelectronic chip array, Nat Biotech 18:199-204.
Wienholds, 2004, Target-selected gene inactivation in zebrafish, Meth Cell Biol 77:69-90.
Wolford, 2000, High-throughput SNP detection by using DNA pooling and denaturing high performance liquid chromatography (DHPLC), Hum Genet 107:483-487.
Xi, 2011, Copy number variation detection in whole-genome sequencing data using the Bayesian information criterion, PNAS 108(46):e1128-e1136.
Xu, 2012, FastUniq: A fast de novo duplicates removal tool for paired short reads, PLoSOne 7(12):e52249.
Ziller, 2011, Genomic distribution and inter-sample variation of non-CpG methylation across human cell types, PLoS Genet, 7(12):e1002389.
Amos, 2000, DNA pooling in mutation detection with reference to sequence analysis, Am J Hum Genet 66:1689-1692.
Applied Biosystems, 2010, BigDye Terminator v3.1 Cycle Sequencing Kit Protocol (72 pages).
Baldwin, 2009, Multilocus sequence typing of Cronobacter sakazakii and Cronobacter malonaticus reveals stable clonal structures with clinical significance which do not correlate with biotypes, BMC Microbiol 9(223):1-9.
Bao, 2014, Review of current methods, applications and data management for the bioinformatics analysis of whole exome sequencing, Cancer Informatics 13:S2, pp. 67-82.
Bellos, 2014, cnvCapSeq: detecting copy number variation in long-range targeted resequencing data, Nucleic Acids Res 42(20):e158.
Benson, 2013, Genbank, Nucl Acids Res 41:D36-D42.

Blomquist, 2013, Targeted RNA-Sequencing with Competitive Multiplex-PCR Amplicon Libraries, PLOS ONE 8(11):e79120.
Bodi, 2013, Comparison of commercially available target enrichment methods for next-generation sequencing, J Biomolecular Tech 24:73-86.
Borodina, 2011, A strand-specific library preparation protocol for RNA sequencing methods, Meth Enzymol 500:79-98.
Browning, 2011, Haplotype phasing: existing methods and new developments, Nature Rev Gen, 12(10):703-714.
Callow, 2004, Selective DNA amplification from complex genomes using universal double-sided adaptors, Nucl Acids Res 32(2):e21/1-6.
Church, 1988, Multiplexed DNA sequencing, Science 240:185-188.
Colbert, 2001, High-throughput screening for induced point mutations, Plant Physiol 126:480-484.
Collard, 2005, An introduction to markers, quantitative trait loci (QTL) mapping and marker-assisted selection for crop improvements: the basic concepts Euphytica 142:169-196.
Diao, 2015, Building highly-optimized, low latency pipelines for genomic data analysis, 7th Bienniel COnference on Innovative Data Systems Research (CIDR'15), January 4-7, Asilomar, California, USA, 12 pages.
Eminaga, 2013, Quantification of microRNA Expression with Next-Generation Sequencing, Unit 4.17 in Current Protocols in Molecular Biology, Wiley, New York, NY (14 pages).
Faircloth, 2012, Not all sequence tags are created equal: Designing and validating sequence identification tags robust to indels, PLoSONE 7(8):e42543.
Fakhrai-Rad, 2002, Pyroseqeuncing: An accurate detection platform for single nucleotide polymorphisms, Human Mutation 19:479-485.
Frederico, 1990, A sensitive genetic assay for the detection of cytosine deamination: determination of rate constants and the activation energy, Biochemistry 29(10):2532-2537.
Fromer, 2014, Using XHMM Software to Detect Copy Number Variation in Whole-Exome Sequencing Data, Curr Protoc Hum Genet 81(7.23):1-21.
Fu, 2014, Molecular indexing enables quantitative targeted RNA sequencing and reveals poor efficiencies in standard library preparations, PNAS 111(5):1891-1896 and Supporting Information, 8 pages.
Genereux, 2008, Errors in the bisulfite conversion of DNA: modulating inappropriate and failed conversion frequencies, Nucl Acids Res 36(22):e150.
Gonzales-Beltran, 2015, From Peer-REviewed to Peer-reproduced in scholary publishing: the complementary roles of data models and workflows in Bioinformatics, PLOS ONE 10(7):127612, 23 pages.
Grothues, 1993, PCR amplification of megabase DNA with tagged random primers (T-PCR), Nucl Acids Res 21:1321-1322.
Hajibabaei, 2005, Critical factors for assembling a high volume of DNA barcodes, Phil Trans R Soc B 360:1959-1967.
Head, 2015, Library construction for next-generation sequencing: Overviews and challenges, Biotechniques 56(2):61.
Ilumina, 2011, TruSeq RNA and DNA Sample Preparation Kits v2, 1-15 Illumina, dated 27 Apr. 27, 2011 (4 pages).
Ion Total RNA-Seq Kit v2, User Guide, 2012, Life Technologies (82 pages).
Jiang, 2015, CODEX: a normalization and copy number variation detection method for whole exome sequencing, Nucleic Acids Res 43(6):e39.
John, 2011, Detection of Viral microRNA with S1 Nuclease Protection Assay, Chapter 10 in Antiviral RNAi, van Rig, Ed. Springer.
Jones, 2007, The epigenomics of cancer, Cell, 128(4):683-592.
Kalari, 2014, MAP-Rseq: Mayo analysis pipeline for RNA sequencing, BMC bioinformatics, vol. 15, 224, 13 pages and Supplemental Information.
Karczewki, 2014, STORMSeq: an open-source user-friendly pipleline for processing personal genomics data in the cloud.PLOS ONE 9(1):e84860, 5 pages.
Kim, 2011, TopHat-Fusion: an algorithm for discovery of novel fusion transcripts, Cancer Discovery, vol. 12:R72, 15 pages.
Krumm, 2012, Copy number variation detection and genotyping from exome sequence data, Genome Res 22 (8):1525-1532.

(56) References Cited

OTHER PUBLICATIONS

Lai, 2004, Characterization of the maize endosperm transcriptome and its comparison to the rice genome, Genome Res14:1932-1937.
Langmead, 2009, Ultrafast and memory-efficient alignment of short DNA sequences to the human genome, Genome Biol 10:R25.
Levin, 2010, Comprehensive comparative analysis of strand-specific RNA sequencing methods, Nat Methods 7 (9):709-715.
Li, 2012, Contra: copy number analysis for targeted resequencing, Bioinformatics 28(10): 1307-1313.
Li, 2014, Bioinformatics pipelines for targeted resequencing and whole-exome sequencing of human and mouse genomes: a virtual appliance approach for instant deployment, PLOS ONE, 9(4):e95217 and Supplemental Information, 11 pages.
Liang, 2014, Copy number variation sequencing for comprehensive diagnosis of chromosome disease syndromes, The Journal of Molecular Diagnostics, 16(5), plus Supplemental Information, 15 pages.
Lindstrom, 2004, Pyrosequencing for detection of Lamivudine-resistant Hepatitis B virus, J Clin Microb 42 (10):4788-4795.
Liu, 2008, Sequence space coverage, entropy of genomes and the potential to detect non-human DNA in human samples, BMC Genomics 9(509):1-17.
Ma, 2015, Quantitative Analysis of Copy Number Variants Based on Real-Time LightCycler PCR, Curr Protoc Hum Genet 80:7.21 1-7.23 8.
Machine translation generated Jun. 18, 2021, of JP 2015511819 A (400 pages).
Machine translation generated on Mar. 7, 2018, of CN 105890722 by website of European Patent Office (4 pages).
Mag, 1991, Synthesis and selective cleavage of an oligodeoxynucleotide containing a bridged internucleotide 5'—phosphorothioate linkage, Nucleic Acids Res 19(7):1437-1441.
Margulies, 2005, Genome sequencing in open microfabricated high density picoliter reactors, Nature 437 (7057):376-380.
Mauk, 2018, Simple Approaches to Minimally-Instrumented, Microfluidic-Based Point-of-Care Nucleic Acid Amplification Tests, Biosensors 8(1):e17.
McCloskey, 2007, Encoding PCR products with batch-stamps and barcodes, Biochem Genet 45:761-767.

\* cited by examiner

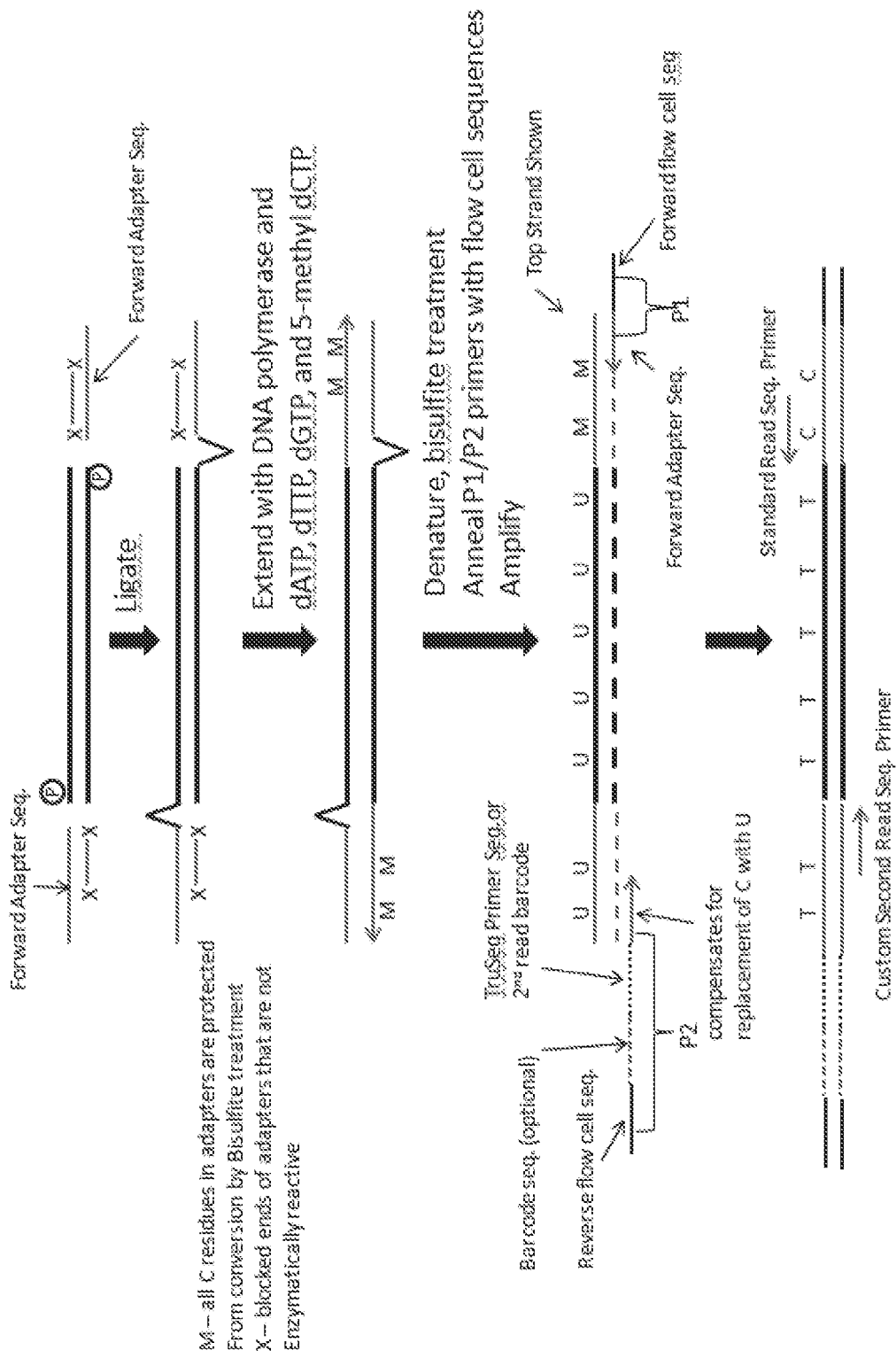

METHODS FOR CREATING DIRECTIONAL BISULFITE-CONVERTED NUCLEIC ACID LIBRARIES FOR NEXT GENERATION SEQUENCING

CROSS-REFERENCE

This application is a continuation of U.S. application Ser. No. 14/991,340, filed Jan. 8, 2016, which is a continuation of U.S. application Ser. No. 13/938,059, filed Jul. 9, 2013, which claims the benefit of U.S. Provisional Application Nos. 61/801,382, filed Mar. 15, 2013 and 61/669,613, filed Jul. 9, 2012, each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 14, 2021 is named NUGN-039-03US-Sequence-Listing and is 8 kilobytes in size.

BACKGROUND

Epigenomics, e.g., DNA methylation, play a role in mammalian development and disease. For example, DNA methylation is implicated in embryonic development, genomic imprinting and X-chromosome inactivation through regulation of transcriptional activity, chromatin structure and chromatin stability (Robertson, *Nat Review Genet* 6:597-610, 2005). Increased DNA methylation (hypermethylation) at promoter regions of genes can be associated with transcriptional silencing, whereas decreased methylation (hypomethylation) at promoter regions can be associated with increased gene activity. Aberrant methylation patterns can be associated with various human pathologies, including tumor formation and progression (Feinberg and Fogelstein, *Nature* 301:89-92, 1983; Esteller, *Nat Review Genet* 8: 286-298, 2007; and Jones and Paylin, *Cell* 128:683-692, 2007). Therefore, analysis of DNA methylation status across the human genome can be of interest.

DNA methylation can occur at the C5 position of cytosine residues. In mammals, 5-methylcytosine can appear in the CpG dinucleotide context (Ramsahoye et al., *Proc Natl Acad Sci USA* 97:5237-5242, 2000). Recent data suggests that approximately 25% of all cytosine methylation identified in stem cells can occur in non-CpG context (see Ziller et al., *PLoS Genet.* 7(12):e1002389, 2011). Although CpG dinucleotides can be underrepresented in the genome, stretches of sequences known as CpG islands can exist that are rich in CpG dinucleotides. These CpG islands can be associated with promoter regions and span several hundred nucleotides or more.

Methods for measuring DNA methylation at specific genomic loci include, for example, immunoprecipitation of methylated DNA, methyl-binding protein enrichment of methylated fragments, digestion with methylation-sensitive restriction enzymes, and bisulfite conversion followed by Sanger sequencing (reviewed in Laird, *Nat Review Genet* 11: 191-203, 2010). Bisulfite treatment can convert unmethylated cytosine residues into uracils (the readout of which can be thymine after amplification with a polymerase). Methylcytosines can be protected from conversion by bisulfite treatment to uracils. Following bisulfite treatment, methylation status of a given cytosine residue can be inferred by comparing the sequence to an unmodified reference sequence.

Techniques have been developed for profiling methylation status of the whole genome, i.e. the methylome, at a single-base resolution using high throughput sequencing technologies. Bisulfite conversion of genomic DNA combined with next generation sequencing (NGS), or BS-seq, is one strategy. Because of the high cost still associated with genome-wide methylation sequencing, variations of BS-seq technology that enable genome partitioning to enrich for regions of interest can be used. One such variation is reduced representation BS-seq (RRBS), which can involve digestion of a DNA sample with a methylation-insensitive restriction endonuclease that has CpG dinucleotide as a part of its recognition site, followed by bisulfite sequencing of the selected fragments (Meissner et al., *Nucleic Acids Res.* 33(18):5868-5877, 2005).

There is a need for improved methods for sequencing and analysis of bisulfite-converted DNA. In particular, methods for cost-effective genome-wide methylation NGS sequencing are needed. Such methods could enable retaining information on the original genomic DNA directionality (strandedness).

There is also a need for improved methods of analyzing transcription. Transcription is a process in which single-stranded RNA copies can be made from sections of double-stranded genomic DNA. In other words, only one of the two complementary strands of the genomic DNA (termed "the template strand"), can be used for transcription. Transcription start sites and direction can both be defined by specific promoter regions. However, in complex organisms, genes can have several different transcription start sites which can be active under different conditions. Moreover, recent transcriptome mapping studies have shown that much of the genome is transcribed, and in many instances transcripts from both strands of specific genomic loci are detectable. While some of these transcripts map to known protein-encoding genes, many can be derived from regions of DNA thought to be non-genic.

The process of fragmenting double-stranded DNA, such as genomic DNA, can result in a complete loss on any information on the transcriptional direction or strandedness. Preserving strandedness information can play a role in data analysis as it can allow determining the directionality of transcription and gene orientation, and it can facilitate the detection of opposing and overlapping transcripts. The methods, compositions, and kits provided herein can maintain the directional (strandedness) information of the original nucleic acid sample.

The methods described herein can also be used for the generation of directional next generation sequencing (NGS) libraries from bisulfite-converted DNA. Such methods can be useful, for example, for determining the methylation status across a genome, or alternatively, for determining the methylation status at given genomic loci. The methods described herein can provide an efficient, cost-effective strategy for high throughput sequencing of bisulfite-converted DNA, while simultaneously maintaining the directional information of the original sample.

SUMMARY

Provided herein are novel methods, compositions and kits for the construction of directional nucleic acid sequencing libraries from bisulfite-treated DNA. Specifically, in one aspect, methods and compositions are provided for generating nucleic acid libraries from bisulfite-converted DNA that are compatible with high throughput sequencing methods and simultaneously maintain the directional (strandedness) information of the original nucleic acid sample. The methods provided herein can be used to analyze the methylation status of a DNA sample in a specific genomic region or locus or to determine the methylation status across the genome.

In one aspect, provided herein is a method for the creation of bisulfite-converted directional NGS libraries using oligonucleotide adapters in which one or more cytosine residues has been replaced with 5-methylcytosine. In some embodiments, the method comprises: a) fragmenting genomic DNA, thereby generating DNA fragments; b) performing end repair on the DNA fragments; c) ligating a single adapter forming a partial duplex to both ends of each DNA fragment, where the long arm of the partial duplex adapter has one or more cytosine residues replaced with 5-methylcytosine; d) extending the adapter ends with a polymerase; e) denaturing DNA, thereby generating single-stranded DNA fragments; f) subjecting the single-stranded DNA fragments with ligated adapters to bisulfite treatment, thereby converting unprotected cytosine residues to uracils and creating unique PCR priming sites at 5' and 3' ends of the DNA fragments; g) performing PCR; and, optionally, h) sequencing and analyzing the amplified PCR products.

In some embodiments, the 5' and/or 3' ends of the short arm of the partial duplex adapter are blocked and enzymatically unreactive to prevent adapter dimer formation. In one embodiment, the 3' end of the short arm of the partial duplex adapter is blocked with a terminal dideoxycytosine (3ddC). In another embodiment, the 5' end of the short arm of the partial duplex adapter contains a biotin moiety. Other blocking methods include, but are not limited to, 1) incorporation of various modified nucleotides (for example, phosphorothiorate-modified bases) and 2) incorporation of non-nucleotide chemical moieties.

In some embodiments, step g) comprises annealing to the DNA fragments a sequence-specific oligonucleotide primer, or multiple sequence-specific oligonucleotide primers, that contain an additional identifier sequence, or a barcode sequence. In some embodiments, each oligonucleotide annealed in step g) comprises at least one of a plurality of barcode sequences, where each barcode sequence of the plurality of barcode sequences differs from every other barcode sequence in the plurality of barcode sequences.

In other embodiments, distinct adapters, each forming a partial duplex, are ligated to the ends of the DNA fragments instead of ligating a single partial duplex adapter to both ends of each DNA fragment.

In other embodiments, 5-methylcytosine capture (by, for instance, methyl-C binding protein or antibodies specific to 5-methylcytosine) is performed prior to bisulfite conversion, and cytosine analogs resistant to bisulfite treatment other than 5-methylcytosine are incorporated in the long arm of the duplex adapter. In one embodiment, one or more cytosine residues in the long arm of the duplex adapter are replaced by 5-hydroxycytosine. In another embodiment, one or more cytosine residues in the long arm of the duplex adapter are replaced by 5-hydroxymethylcytosine. In another embodiment, one or more cytosine residues in the long arm of the duplex adapter are replaced by 5-propynylcytosine.

In another aspect, provided herein are methods for the creation of bisulfite-converted directional NGS libraries using oligonucleotide adapters with no modified cytosines but instead performing the adapter extension step in the presence of 5-methyl dCTP. In some embodiments, the method comprises: a) fragmenting genomic DNA, thereby generating DNA fragments; b) performing end repair on the DNA fragments; c) ligating a single adapter forming a partial duplex to both ends of each DNA fragment; d) extending the adapter ends with a polymerase, where the dNTP mix contains 5-methyl dCTP instead of dCTP; e) subjecting the DNA fragments with ligated adapters to bisulfite treatment, thereby converting unprotected cytosine residues to uracils and creating unique PCR priming sites at the 5' and 3' ends of the DNA fragments; f) performing PCR; and optionally, g) sequencing and analyzing the amplified PCR products.

In some embodiments, the 5' and/or 3' ends of the short arm of the partial duplex adapter are blocked and enzymatically unreactive to prevent adapter dimer formation. In one embodiment, the 3' end of the short arm of the partial duplex adapter is blocked with a terminal dideoxycytosine (3ddC). In another embodiment, the 5' end of the short arm of the partial duplex adapter contains a biotin moiety. Other blocking methods include, but are not limited to, 1) incorporation of various modified nucleotides (for example, phosphorothiorate-modified bases) and 2) incorporation of non-nucleotide chemical moieties.

In some embodiments, step g) comprises annealing to the DNA fragments a sequence-specific oligonucleotide primer, or multiple sequence-specific oligonucleotide primers, that contain an additional identifier sequence, or a barcode sequence. In some embodiments, each oligonucleotide annealed in step g) comprises at least one of a plurality of barcode sequences, where each barcode sequence of the plurality of barcode sequences differs from every other barcode sequence in the plurality of barcode sequences.

In other embodiments, distinct adapters, each forming a partial duplex, are ligated to the ends of the DNA fragments instead of ligating a single partial duplex adapter to both ends of each DNA fragment.

In other embodiments, 5-methylcytosine capture (by, for instance, methyl-C binding protein or antibodies specific to 5-methylcytosine) is performed prior to bisulfite conversion, and cytosine analogs resistant to bisulfite treatment other than 5-methyl dCTP are used in the extension reaction in step d). In one embodiment, one or more cytosine residues in the long arm of the duplex adapter are replaced by 5-hydroxycytosine. In another embodiment, one or more cytosine residues in the long arm of the duplex adapter are replaced by 5-hydroxymethylcytosine. In another embodiment, one or more cytosine residues in the long arm of the duplex adapter are replaced by 5-propynylcytosine.

Kits for performing any of the methods described herein are also provided. Such kits may include reagents, enzymes and platforms for fragmentation, end repair, ligation, bisulfite treatment, amplification, and sequencing of nucleic acids. In one embodiment, a kit is provided comprising: a) an adapter or several adapters, b) one or more of oligonucleotide primers, and c) reagents for amplification. In another embodiment, the kit further comprises reagents for sequencing. A kit will preferably include instructions for employing the kit components as well as the use of any other reagent not included in the kit.

In one aspect, described herein is a method for generating a directional polynucleotide library comprising: (a) ligating a first strand of an adapter to each 5' end of one or more double stranded polynucleotides, wherein the adapter comprises a duplexed sequence comprising the first strand and a second strand, wherein the first strand comprises one or more modified cytosine bases resistant to bisulfite treatment;

(b) extending each 3' end of the one or more double stranded polynucleotides comprising a ligated first strand of the adapter using the ligated first strand of the adapter as a template; (c) treating the product of step b) with bisulfite, thereby converting unmodified cytosine bases in the one or more polynucleotides comprising adapters to uracil; (d) amplifying the product of step c) to generate an amplified polynucleotide comprising non-complementary adapter sequence at each end of each strand, thereby generating a directional polynucleotide library. In some embodiments, the method further comprises an additional step of sequencing the product of step (d). In some embodiments, the one or more double stranded polynucleotides are one or more fragments of one or more polynucleotides obtained from a sample. In some embodiments, the method further comprises fragmenting the one or more double stranded polynucleotides prior to step a) to generate fragmented double stranded polynucleotides. In some embodiments, the method further comprises end-repairing the fragmented double stranded polynucleotides. In some embodiments, the one or more double-stranded polynucleotides comprise double stranded DNA. In some embodiments, the DNA comprises genomic DNA or cDNA. In some embodiments, the second strand is incapable of ligation to either end of the one or more double stranded polynucleotides. In some embodiments, each end of the second strand is blocked and enzymatically unreactive. In some embodiments, a 3' end of the second strand comprises a terminal dideoxycytosine. In some embodiments, a 5' end of the second strand comprises a biotin moiety. In some embodiments, the method further comprises denaturing the product of step b) prior to step c), thereby generating single-stranded polynucleotide fragments comprising sequence of the first strand of the adapter at the 5' end and a sequence complementary to the sequence of the first strand of the adapter at the 3' end. In some embodiments, the amplifying comprises the use of a first primer and a second primer, wherein the first primer is directed against a sequence complementary to the first strand of the adapter comprising uracil residues following bisulfite treatment, and the second primer is directed against a sequence complementary to the first strand of the adapter. In some embodiments, the one or more modified cytosine bases comprise a cytosine analog resistant to bisulfite treatment. In some embodiments, the cytosine analog resistant to bisulfite treatment is 5-methylcytosine, 5-hydroxymethylcytosine, or 5-propynylcytosine. In some embodiments, the single-stranded polynucleotides comprising sequence of the first strand at the 5' end and the sequence complementary to the sequence of the first strand at the 3' end is captured prior to step c) wherein the capture is performed with a binding agent directed against the one or more modified cytosine bases. In some embodiments, the one or more modified cytosine bases comprises a cytosine analog resistant to bisulfite treatment. In some embodiments, the binding agent is a methylcytosine binding protein. In some embodiments, the methylcytosine binding protein is an anti-5-methylcytosine antibody. In some embodiments, the first and/or second primer further comprises a barcode sequence. In some embodiments, the double stranded polynucleotide fragments are captured, wherein the capture is performed with a binding agent directed against one or more modified cytosine residues present in the double-stranded polynucleotide fragments. In some embodiments, the binding agent is a 5-methylcytosine binding protein. In some embodiments, the 5-methylcytosine binding protein is a binding domain of a methyl-CpG binding (MBD) protein. In some embodiments, the methyl-CpG binding (MBD) protein comprises MBD2 or MECP2.

In one aspect, described herein is a method of generating a direction polynucleotide library comprising: (a) ligating a first strand of an adapter to each 5' end of one or more double stranded polynucleotides, wherein the adapter comprises a duplexed sequence comprising the first strand and a second strand; (b) extending each 3' end of the one or more double stranded polynucleotides comprising a ligated first strand of the adapter using the first strand of the adapter as a template, wherein the extension products comprise one or more modified cytosine bases resistant to bisulfite treatment; (c) treating the product of b) with bisulfite, thereby converting unmodified cytosine bases in the polynucleotide and adapter sequence to uracil; and (d) amplifying the product of step c) to generate an amplified polynucleotide comprising non-complementary adapter sequence at each end of each strand, thereby generating a directional polynucleotide library. In some embodiments, the method further comprises an additional step of sequencing the product of step (d). In some embodiments, the one or more double stranded polynucleotides are one or more fragments of one or more polynucleotides obtained from a sample. In some embodiments, the method further comprises fragmenting the one or more double stranded polynucleotides prior to step a) to generate fragmented double stranded polynucleotides. In some embodiments, the method further comprises end-repairing the fragmented double stranded polynucleotides. In some embodiments, the one or more double-stranded polynucleotides comprise double stranded DNA. In some embodiments, the DNA comprises genomic DNA or cDNA. In some embodiments, the second strand is incapable of ligation to either end of the one or more double stranded polynucleotides. In some embodiments, each end of the second strand is blocked and enzymatically unreactive. In some embodiments, a 3' end of the second strand comprises a terminal dideoxycytosine. In some embodiments, a 5' end of the second strand comprises a biotin moiety. In some embodiments, the method further comprises denaturing the product of step b) prior to step c), thereby generating single-stranded polynucleotide fragments comprising sequence of the first strand of the adapter at the 5' end and a sequence complementary to the sequence of the first strand of the adapter at the 3' end. In some embodiments, the amplifying comprises the use of a first primer and a second primer, wherein the first primer is directed against a sequence complementary to the first strand of the adapter comprising uracil residues following bisulfite treatment, and the second primer is directed against a sequence complementary to the first strand of the adapter. In some embodiments, the one or more modified cytosine bases comprise a cytosine analog resistant to bisulfite treatment. In some embodiments, the cytosine analog resistant to bisulfite treatment is 5-methylcytosine, 5-hydroxymethylcytosine, or 5-propynylcytosine. In some embodiments, the single-stranded polynucleotides comprising sequence of the first strand at the 5' end and the sequence complementary to the sequence of the first strand at the 3' end is captured prior to step c) wherein the capture is performed with a binding agent directed against the one or more modified cytosine bases. In some embodiments, the one or more modified cytosine bases comprises a cytosine analog resistant to bisulfite treatment. In some embodiments, the binding agent is a methylcytosine binding protein. In some embodiments, the methylcytosine binding protein is an anti-5-methylcytosine antibody. In some embodiments, the first and/or second primer further comprises a barcode sequence. In some embodiments, the double stranded polynucleotide fragments are captured, wherein the capture is performed with a binding agent directed against one or more modified cytosine residues present in the double-stranded polynucleotide fragments. In some embodiments, the binding agent is a 5-methylcytosine binding protein. In some embodiments, the 5-methylcytosine binding protein is a binding domain of a methyl-CpG binding (MBD) protein. In some embodiments, the methyl-CpG binding (MBD) protein comprises MBD2 or MECP2.

In one aspect, disclosed herein is a method for generating a directional polynucleotide libraries comprising: (a) ligating a first strand of an adapter to each 5' end of a double stranded polynucleotide, wherein the adapter comprises a duplexed sequence comprising the first strand and a second strand, wherein the first strand comprises one or more modified nucleotides resistant to conversion by a converting agent; (b) extending each 3' end of the double stranded polynucleotide comprising a ligated first strand of the adapter as a template; (c) treating a product of step b) with the converting agent, thereby converting one or more unmodified nucleotides to a different nucleotide; and (d) amplifying a product of step c) to generate an amplified polynucleotide comprising non-complementary adapter sequence at each end, thereby generating a directional nucleic acid library. In some embodiments, the method further comprises fragmenting and end-repairing the double stranded polynucleotide prior to step a). In some embodiments, the method further comprises denaturing the product of step b) prior to step c), thereby generating a single-stranded polynucleotide comprising sequence of the first strand at the 5' end and a sequence complementary to the sequence of the first strand at the 3' end. In some embodiments, the one or more modified nucleotides comprise a modified base resistant to conversion with the converting agent. In some embodiments, the converting agent is bisulfite and the modified base is a cytosine analog resistant to bisulfite treatment. In some embodiments, the cytosine analog is 5-methyl dCTP, 5-hydroxymethyl dCTP, or 5-propynyl dCTP. In some embodiments, treatment with bisulfite converts unmodified cytosine to uracil. In some embodiments, the method further comprises an additional step of sequencing the amplified polynucleotide fragment comprising non-complementary adapter sequence at each end. In some embodiments, the double-stranded nucleic acid is a fragment of a polynucleotide obtained from a sample. In some embodiments, the double-stranded polynucleotide comprises double stranded DNA. In some embodiments, the DNA comprises genomic DNA or cDNA. In some embodiments, the second strand is incapable of ligation to either end of the double stranded polynucleotide. In some embodiments, each end of the second strand is blocked and enzymatically unreactive. In some embodiments, a 3' end of the second strand comprises a terminal dideoxycytosine. In some embodiments, a 5' end of the second strand comprises a biotin moiety. In some embodiments, the amplifying comprises the use of a first primer and a second primer wherein the first primer is directed against the sequence complementary to the first strand altered by the treatment with the converting agent, while the second primer is directed against a sequence complementary to the first strand of the adapter.

In one aspect, disclosed herein is a method of generating a direction nucleic acid library comprising: (a) ligating a first strand of an adapter to each 5' end of a double stranded polynucleotide, wherein the adapter comprises a duplexed sequence comprising the first strand and a second strand; (b) extending each 3' end of the double stranded nucleic acid comprising a ligated first strand of the adapter as a template, wherein the extension product comprises one or more modified nucleotides resistant to treatment with a converting agent; (c) treating the product of b) with the converting agent, thereby converting one or more unmodified nucleotide to a different nucleotide; and (d) amplifying the product of step c) to generate an amplified polynucleotide comprising non-complementary adapter sequence at each end, thereby generating a directional nucleic acid library. In some embodiments, the method further comprises fragmenting and end-repairing the double stranded polynucleotide prior to step a). In some embodiments, the method further comprises denaturing the product of step b) prior to step c), thereby generating a single-stranded polynucleotide comprising sequence of the first strand at the 5' end and a sequence complementary to the sequence of the first strand at the 3' end. In some embodiments, the one or more modified nucleotides comprise a modified base resistant to conversion with the converting agent. In some embodiments, the converting agent is bisulfite and the modified base is a cytosine analog resistant to bisulfite treatment. In some embodiments, the cytosine analog is 5-methyl dCTP, 5-hydroxymethyl dCTP, or 5-propynyl dCTP. In some embodiments, treatment with bisulfite converts unmodified cytosine to uracil. In some embodiments, the method further comprises an additional step of sequencing the amplified polynucleotide fragment comprising non-complementary adapter sequence at each end. In some embodiments, the double-stranded nucleic acid is a fragment of a polynucleotide obtained from a sample. In some embodiments, the double-stranded polynucleotide comprises double stranded DNA. In some embodiments, the DNA comprises genomic DNA or cDNA. In some embodiments, the second strand is incapable of ligation to either end of the double stranded polynucleotide. In some embodiments, each end of the second strand is blocked and enzymatically unreactive. In some embodiments, a 3' end of the second strand comprises a terminal dideoxycytosine. In some embodiments, a 5' end of the second strand comprises a biotin moiety. In some embodiments, the amplifying comprises the use of a first primer and a second primer wherein the first primer is directed against the sequence complementary to the first strand altered by the treatment with the converting agent, while the second primer is directed against a sequence complementary to the first strand of the adapter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features provided herein are set forth with particularity in the appended claims. A better understanding of the features and advantages provided herein will be obtained by reference to the following description that sets forth illustrative embodiments, in which the principles provided herein are utilized, and the accompanying drawings of which:

FIG. 2 depicts generation of a directional, bisulfite-converted NGS library using unmodified partial duplex adapters and adapter extension in the presence of 5-methyl dCTP.

DETAILED DESCRIPTION

I. Overview

Figure 1:
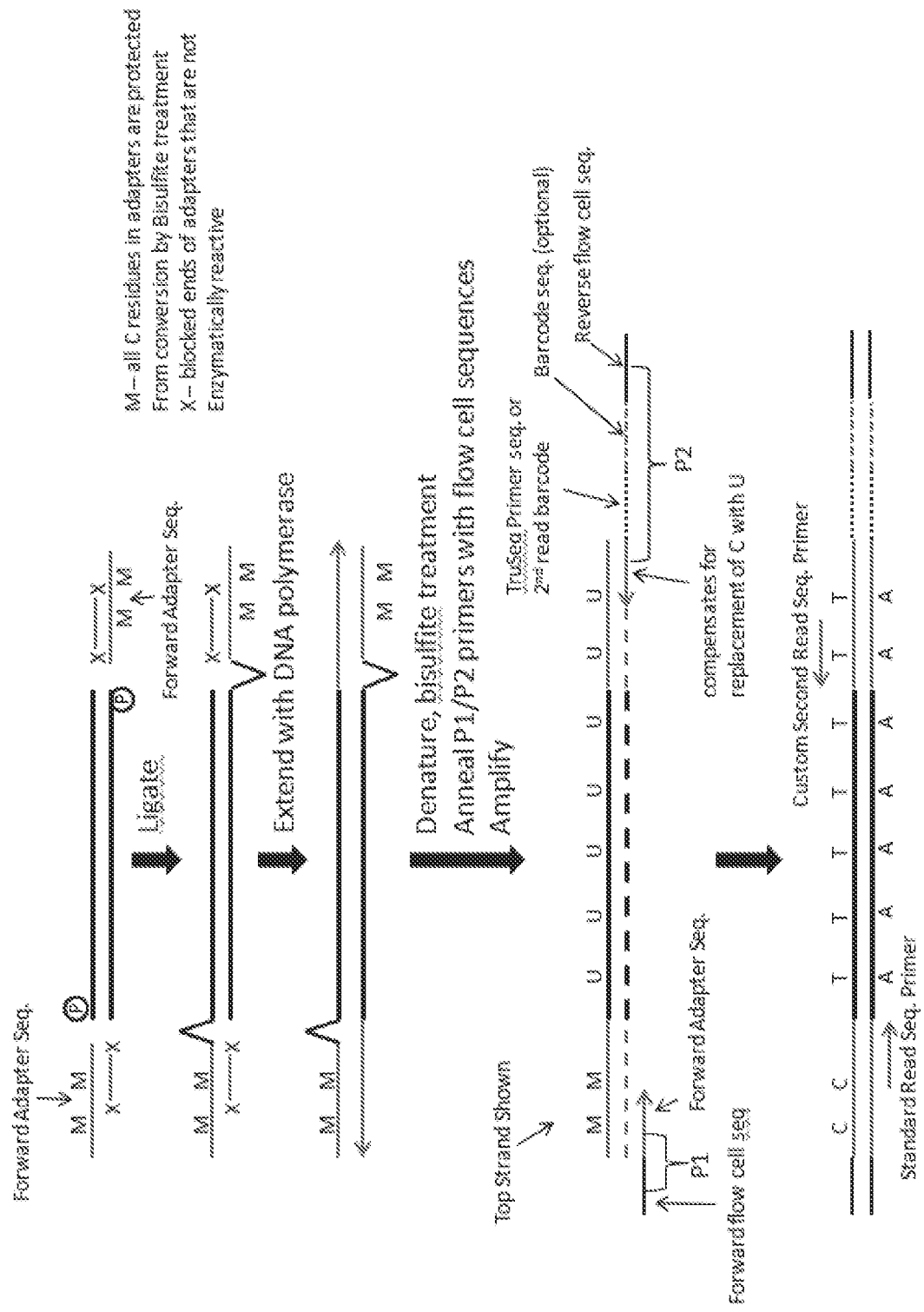
FIG. 1 depicts generation of a directional, bisulfite-converted next generation sequencing (NGS) library using modified partial duplex-forming adapters comprising 5-methylcytosine residues incorporated into the ligation strand of the adapters.

Provided herein are methods, compositions, and kits for the construction of directional nucleic acid sequencing libraries from bisulfite-treated DNA. In one aspect, provided herein are methods, compositions, and kits for generating nucleic acid libraries from bisulfite-converted DNA that are compatible with high throughput sequencing methods and simultaneously maintain the directional (strandedness) information of the original nucleic acid sample. The methods can be used to analyze the methylation status of a DNA sample in a specific genomic region or locus or to determine the methylation status across the genome.

FIG. 1 illustrates an embodiment of a method for generating a directional library using modified duplex adapters. In some cases, a modified duplex adapter is joined, e.g., ligated, to a double-stranded polynucleotide, e.g., double stranded DNA. The modified duplex adapter comprises at least one modified nucleotide, e.g., 5'-methycytosine, in a first strand, and all of the cytosines in the first strand are 5-methylcytosines. In some cases, only the strand of the adapter comprising the at least one modified nucleotide is joined to one end (e.g., 5' end) of a first strand of the double stranded polynucleotide. Adapters can be joined to one end of each strand of the double-stranded polynucleotide, e.g., a first adapter can be ligated to the 5' end of the first strand the double-stranded polynucleotide, and a second adapter can be ligated to the 5' end of the second strand of the double-stranded polynucleotide. The first and second adapter can be the same adapter. The strand of each adapter not ligated to the double-stranded polynucleotide can be blocked for use in enzymatic reactions at one or both ends. In some cases, the strand of the first adapter joined to the 5' end of the first strand of the double stranded polynucleotide serves as template for extension of the non-ligated end (3' end) of the second strand of the double stranded polynucleotide. The strand of second adapter joined to the 5' end of the second strand of the double-stranded polynucleotide serves as template for extension of the non-ligated end (3' end) of the first strand of the double-stranded polynucleotide. In some cases, the double stranded polynucleotide with each end comprising adapter sequence is denatured, thereby generating single stranded polynucleotides. In some cases, the single stranded polynucleotides comprising adapter sequence are treated with a converting agent, e.g., bisulfite, which converts unmodified cytosines to uracils, thereby generating single stranded polynucleotides comprising non-complementary ends. In some cases, the single stranded polynucleotides comprising non-complementary ends are amplified using primers directed against sequence present in the non-complementary ends, thereby generating amplified products comprising with strands with non-complementary ends.

FIG. 2 illustrates an embodiment for generating a directional library using unmodified duplex adapters. An unmodified duplex adapter is joined to a double-stranded polynucleotide. In this example, only a first strand of the duplex adapter is ligated to one end (e.g., 5' end) of the first strand of the double stranded polynucleotide. One strand of a second adapter is ligated to the 5' end of a second strand of the double stranded polynucleotide. The first adapter and second adapter can be the same adapter. In some cases, the strands of the adapters ligated to the 5' ends of the double stranded polynucleotide serve as templates for extension of the non-ligated ends (3' ends) of each strand of the double stranded polynucleotide. At least one modified nucleotide (e.g., 5-methylcytosine) is incorporated into the extension products, thereby generating a double stranded polynucleotide with individual strands comprising complementary 5' and 3' ends. In some cases, the double stranded polynucleotide is denatured, thereby generating single stranded polynucleotides comprising complementary 5' and 3' ends. In some cases, the single stranded polynucleotides are treated with a converting agent, e.g., bisulfite, which converts unmodified cytosines to uracil. In some cases, treatment with bisulfite generates single stranded polynucleotides comprising non-complementary 5' and 3' ends. In some cases, the single stranded polynucleotides are amplified using primers directed against sequence present in the non-complementary ends, wherein a first primer is directed against sequence present in one end (e.g. the 3' end) and a second primer is directed against sequence present in the other, non-complementary, end (e.g. 5' end), thereby generating amplified products comprising non-complementary ends.

II. Strand-Specific Selection

The compositions, methods, and kits provided herein can be used for retaining directional information in double-stranded DNA. The terms "strand specific," "directional," or "strandedness" can refer to the ability to differentiate in a double-stranded polynucleotide between the two strands that are complementary to one another. The term "strand marking" can refer to any method for distinguishing between the two strands of a double-stranded polynucleotide. The term "selection" can refer to any method for selecting between the two strands of a double-stranded polynucleotide.

In some cases embodiments, one strand of a double-stranded polynucleotide is marked or labeled by incorporation of a modified nucleotide or nucleotides. In some cases, strand marking is accomplished by ligation of a duplex adapter to the double-stranded polynucleotide, wherein one of the two strands of the duplex adapter comprises at least one modified nucleotide. A modified base or nucleotide can be incorporated into a strand of the adapter at about, more than, less than, or at least every 1, 2, 3, 4, 5, 6, 7, 8, 9, 10, 15, 20, 25, 30, 40, 50, 65, 75, 85, 90, 95, 100, 110, 120, 130, 140, 150, 160, 170, 180, 190, 200, 225, or 250 nucleotides. In some cases, the modified nucleotide is incorporated about, more than, less than, or at least every 200, 100, 50, 25, 20, 15, 10, or 5 nucleotides. In another embodiment, the modified nucleotide is incorporated about, more than, less than, or at least every 5 to 10, 10 to 15, 15 to 20, 20 to 25, 25 to 50, 50 to 100, 100 to 150, or 150 to 200 nucleotides. In other embodiments, a duplex adapter containing no modified nucleotides is ligated to a double-stranded polynucleotide, and strand marking by incorporation of modified nucleotides, e.g., 5-methylcytosine, occurs during extension of the adapters by a polymerase. In some cases, strand marking further comprises subjecting polynucleotides to a treatment by a biological or chemical agent that can differentiate between polynucleotide strands containing only unmodified nucleotides and polynucleotide strands containing at least one modified nucleotide. In some cases, bisulfite treatment is used to distinguish between polynucleotide strands containing unmodified cytosines from polynucleotide strands containing modified cytosine residues.

The methods described herein can be used to generate directional libraries from double-stranded polynucleotides obtained from any source. In some cases, one strand of a duplex adapter comprises several cytosine analogs which are protected from bisulfite conversion in place of cytosine residues, while the other strand of the duplex adapter contains no cytosine analogs. The cytosine analogs can be 5-methylcytosine (5-MeC), 5-hydroxymethylcytosine or 5-propynylcytosine. Following bisulfite treatment and PCR, distinct sequences and priming sites can be created at each end of the polynucleotide fragments (due to one arm of the duplex adapter having cytosine analogs that are protected from cytosine to uracil conversion), thereby maintaining directional (strandedness) information of the original polynucleotide sample. In some cases, an additional feature of a duplex adapter is that the 5' and 3' ends of the one strand of the partial duplex adapter comprises an enzymatically unreactive blocking group.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

Based on the methods described herein, the retention of the directionality and strand information of the polynucleotide template can be determined with greater than 50% efficiency. The efficiency of retention of directionality and strand orientation using the methods described herein can be >50%, >55%, >60%, >65%, >70%, >75%, >80%, >85%, >90%, or >95%. The efficiency of retention of directionality and strand orientation can be >99%. The methods described herein can be used to generate directional polynucleotide libraries wherein greater than 50% of the polynucleotides in the polynucleotide library comprise a specific strand orientation. The retention of a specific strand orientation using the methods described herein can be >50%, >55%, >60%, >65%, >70%, >75%, >80%, >85%, >90%, or >95%. The retention of specific strand orientation of polynucleotides in the directional polynucleotide library can be >99%.

III. Polynucleotides, Samples, and Nucleotides

The directional nucleic acid library can be generated from a polynucleotides obtained from a source of polynucleotides. The polynucleotides can be single-stranded or double stranded. In some cases, the polynucleotide is DNA. The DNA can be obtained and purified using standard techniques in the art and include DNA in purified or unpurified form. The DNA can be mitochondrial DNA, cell-free DNA, complementary DNA (cDNA), or genomic DNA. In some cases, the polynucleotide is genomic DNA. The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosome 1, 2, 3, 4, 5, 6, 7, 8, 9, 10, 11, 12, 13, 14, 15, 16, 17, 18, 19, 20, 21, 22, X, or Y. In some cases, the DNA is double-stranded DNA. In some cases, the double-stranded DNA is genomic DNA. In some cases, the DNA is cDNA. In some cases, the cDNA is double-stranded cDNA. In some cases, the cDNA is derived from RNA, wherein the RNA is subjected to first strand synthesis followed by second strand synthesis. The RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs. First strand synthesis can be performed using any number of RNA dependent DNA polymerases known in the art.

The source of polynucleotides for use in the methods described herein can be a sample comprising the polynucleotides. The polynucleotides can be isolated from the sample and purified by any of the methods known in the art for purifying the nucleic acid from the sample. The sample can be derived from a non-cellular entity comprising polynucleotides (e.g., a virus) or from a cell-based organism (e.g., member of archaea, bacteria, or eukarya domains). In some cases, the sample is obtained from a swab of a surface, such as a door or bench top.

The sample can from a subject, e.g., a plant, fungi, eubacteria, archeabacteria, protest, or animal. The subject can be an organism, either a single-celled or multi-cellular organism. The subject can be cultured cells, which can be primary cells or cells from an established cell line, among others. The sample can be isolated initially from a multicellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant.

The sample can be from a subject (e.g., human subject) who is healthy. In some cases, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be from a subject who is known to have a genetic disease, disorder or condition. In some cases, the subject is known to be wild-type or mutant for a gene, or portion of a gene, e.g., CFTR, Factor VIII (F8 gene), beta globin, hemachromatosis, G6PD, neurofibromatosis, GAPDH, beta amyloid, or pyruvate kinase gene. In some cases, the status of the subject is either known or not known, and the subject is tested for the presence of a mutation or genetic variation of a gene, e.g., CFTR, Factor VIII (F8 gene), beta globin, hemachromatosis, G6PD, neurofibromatosis, GAPDH, beta amyloid, or pyruvate kinase gene.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can be taken from a subject.

The sample can comprise nucleic acid. The nucleic acid can be, e.g., mitochondrial DNA, genomic DNA, mRNA, siRNA, miRNA, cRNA, single-stranded DNA, double-stranded DNA, single-stranded RNA, double-stranded RNA, tRNA, rRNA, or cDNA. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc. Nucleic acids can be extracted from a sample by means available to one of ordinary skill in the art.

The sample can be processed to render it competent for fragmentation, ligation, denaturation, and/or amplification. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

The methods described herein can be used for analyzing or detecting one or more target polynucleotides. The term polynucleotide, or grammatical equivalents, can refer to at least two nucleotides covalently linked together. A polynucleotide described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-0 atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The polynucleotides can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The term "unmodified nucleotide" or "unmodified dNTP" can refer to the four deoxyribonucleotide triphosphates dATP (deoxyadenosine triphosphate), dCTP (deoxycytidine triphosphate), dGTP (deoxyguanosine triphosphate) and dTTP (deoxythymidine triphosphate) that can normally used as building blocks in the synthesis of DNA.

The term "modified nucleotide," "modified dNTP," or "nucleotide analog," can refer to any molecule suitable for substituting one corresponding unmodified nucleotide. The modified nucleotide or dNTP render the polynucleotide more or less susceptible to degradation or alteration by a suitable degrading or altering agent. In some cases, the modified nucleotide substitutes for cytosine, which in its unmodified state undergoes conversion to uracil when subjected to bisulfite treatment. In some cases, the modified nucleotide substituting for cytosine is 5-methylcytosine. In some cases, the modified nucleotide substituting for cytosine is 5-hydroxymethylcytosine. In some cases, the modified nucleotide is 5-propynylcytosine.

The term "barcode" can refer to a known polynucleotide sequence that allows some feature of a polynucleotide with which the barcode is associated to be identified. In some cases, the feature of the polynucleotide to be identified is the sample from which the polynucleotide is derived. In some cases, barcodes are at least 3, 4, 5, 6, 7, 8, 9, 10, 11, 12, 13, 14, 15, or more nucleotides in length. In some cases, barcodes are shorter than 10, 9, 8, 7, 6, 5, or 4 nucleotides in length. A oligonucleotide (e.g., primer or adapter) can comprise about, more than, less than, or at least 1, 2, 3, 4, 5, 6, 7, 8, 9, or 10 different barcodes. In some cases, barcodes associated with some polynucleotides are of different length than barcodes associated with other polynucleotides. Barcodes can be of sufficient length and comprise sequences that can be sufficiently different to allow the identification of samples based on barcodes with which they are associated. In some cases, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, each barcode in a plurality of barcodes differ from every other barcode in the plurality at at least three nucleotide positions, such as at least 3, 4, 5, 6, 7, 8, 9, 10, or more positions. In some cases, an adapter comprises at least one of a plurality of barcode sequences. In some cases, barcodes for a second adapter oligonucleotide are selected independently from barcodes for a first adapter oligonucleotide. In some cases, first adapter oligonucleotides and second adapter oligonucleotides having barcodes are paired, such that adapters of the pair comprise the same or different one or more barcodes. In some cases, the methods described herein further comprise identifying the sample from which a target polynucleotide is derived based on a barcode sequence to which the target polynucleotide is joined. A barcode can comprise a polynucleotide sequence that when joined to a target polynucleotide serves as an identifier of the sample from which the target polynucleotide was derived.

IV. Generating Directional Libraries Using Modified Duplex-Forming Adapters

In one aspect, a method is provided for generating a directional, bisulfite-converted nucleic acid library using modified duplex-forming adapters. The nucleic acid library generated using modified duplex-forming adapters can maintain directional (strandedness) information of the original nucleic acid sample. In some cases, the original nucleic acid is DNA. In some cases, the DNA is double-stranded DNA. In some cases, the double-stranded DNA is genomic DNA. In some cases, the DNA is cDNA. In some cases, the cDNA is double-stranded cDNA.

The method can comprise fragmenting a double stranded polynucleotide to produce double stranded polynucleotide fragments. In some cases, fragmentation can be achieved through methods known in the art. Fragmentation can be through physical fragmentation methods and/or enzymatic fragmentation methods. Physical fragmentation methods can include nebulization, sonication, and/or hydrodynamic shearing. In some cases, the fragmentation can be accomplished mechanically comprising subjecting the nucleic acid to acoustic sonication. In some cases, the fragmentation comprises treating the nucleic acid with one or more enzymes under conditions suitable for the one or more enzymes to generate breaks in the double-stranded nucleic acid. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g, from New England Biolabs). For example, digestion with DNase I can induce random double-stranded breaks in DNA in the absence of $Mg^{++}$ and in the presence of $Mn^{++}$. In some cases, fragmentation comprises treating DNA with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the DNA leaves overhangs having a predictable sequence. In some cases, the method includes the step of size selecting the fragments via standard methods known in the art such as column purification or isolation from an agarose gel.

In some cases, the polynucleotide, for example DNA, can be fragmented into a population of fragmented polynucleotides of one or more specific size range(s). In some cases, the fragments can have an average length from about 10 to about 10,000 nucleotides or base pairs. In some cases, the fragments have an average length from about 50 to about 2,000 nucleotides or base pairs. In some cases, the fragments have an average length from about 100 to about 2,500, about 10 to about 1000, about 10 to about 800, about 10 to about 500, about 50 to about 500, about 50 to about 250, or about 50 to about 150 nucleotides or base pairs. In some cases, the fragments have an average length less than 10,000 nucleotides or bp, less than 7,500 nucleotides or bp, less than 5,000 nucleotides or bp, less than 2,500 nucleotides or bp, less than 2,000 nucleotides or bp, less than 1,500 nucleotides or bp, less than 1,000 nucleotides or bp, less than 500 nucleotides or bp, less than 400 nucleotides or bp, less than 300 nucleotides or bp, less than 200 nucleotides or bp, or less than 150 nucleotides or bp. In some cases, the polynucleotide fragments have an average length of about, more than, less than, or at least 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 nucleotides or base pairs.

In some cases, polynucleotide fragments generated by fragmentation are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the double stranded nucleic acid fragments to produce blunt ends wherein the ends of the polynucleotide fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, double stranded polynucleotide fragments are captured using a binding agent directed against an epigenetic modification within the sequence of the polynucleotide fragments. The epigenetic modification can be methylation. In some cases, the double stranded polynucleotide fragments are captured using a binding agent directed against 5-methylcytosine residues in the double-stranded polynucleotide fragments. The binding agent can be an antibody, or the binding domain of a protein directed against 5-methylcytosine residues. The protein can be a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2.

The method can further comprise ligating an adapter to the double-stranded polynucleotide fragments. Ligation can be blunt end ligation or sticky or cohesive end ligation. The ligation can be performed with any of the enzymes known in the art for performing ligation (e.g. T4 DNA ligase). The adapter can be any type of adapter known in the art including, but not limited to, a conventional duplex or double stranded adapter. The adapter can comprise DNA, RNA, or a combination thereof. The adapters can be about, less than about, or more than about 10, 15, 20, 25, 30, 35, 40, 45, 50, 55, 60, 65, 70, 75, 80, 90, 100, or 200 nucleotides in length. The adapters can be a duplex adapter, partial duplex adapter, or single stranded adapter. In some cases, the adapter is a duplex adapter. In some cases, the duplex adapters comprises about, less than about, or more than about 10, 15, 20, 25, 30, 35, 40, 45, 50, 55, 60, 65, 70, 75, 80, 90, 100, or 200 nucleotides in length. In some cases, the adapter is a partial duplex adapter, wherein the adapter comprises a long strand and a short strand. In some cases, a partial duplex adapter has overhangs of about, more than, less than, or at least 1, 2, 3, 4, 5, 6, 7, 8, 9, 10, 11, 12, 13, 14, 15, 16, 17, 18, 19, or 20 nucleotides. In some cases, the overhang is a 5' overhang. In some cases, the overhang is a 3' overhang. In some cases, the partial duplex adapter comprises a 5' and 3' overhang. In some cases, the adapter comprises duplexed sequence. In some cases, the adapters comprise about, more than, less than, or at least 5, 6, 7, 8, 9, 10, 12, 12, 13, 14, 15, 16, 17, 18, 19, 20, 21, 22, 23, 24, 25, 30, 35, 40, 45, 50, 55, 60, 65, 70, 75, 80, 90, 100, 200, or more of base paired or duplexed sequence. In some cases, the adapter comprises a single stranded adapter. In some cases, a single-stranded adapter comprises about, more than, less than, or at least 10, 15, 20, 25, 30, 35, 40, 45, 50, 55, 60, 65, 70, 75, 80, 90, 100, or 200 nucleotides in length. In some cases, the single-stranded adapter forms a stem-loop or hairpin structure. In some cases, the stem of the hairpin adapter is about, less than about, or more than about 1, 2, 3, 4, 5, 6, 7, 8, 9, 10, 11, 12, 13, 14, 15, 20, 25, 30, 35, 40, 45, 50, 75, 100, or more nucleotides in length. In some cases, the loop sequence of a hairpin adapter is about, less than about, or more than about 5, 10, 15, 20, 25, 30, 35, 40, 45, 50, or more nucleotides in length. The adapter can further comprise known or universal sequence and, thus, allow generation and/or use of sequence specific primers for the universal or known sequence. In some cases, an adapter comprises one or more barcodes. In some cases, the one or more barcodes are in a stem and/or a loop.

In some cases, an adapter is marked via incorporation of at least one modified dNTP. In some cases, the modified dNTP comprises a nucleotide analog resistant to conversion by treatment with a converting agent. The nucleotide analog can be a cytosine analog. The converting agent can be any biological, biochemical, and/or chemical agent capable of altering the base composition of a dNTP. In some cases, the converting agent is a chemical. In some cases, the converting agent is the chemical compound bisulfite or sodium bisulfite. In some cases, the adapter comprises a cytosine analog resistant to conversion by bisulfite treatment. In some cases, the long strand of a partial duplex adapter comprises cytosine analog residues in place of cytosine residues, which are protected from bisulfite conversion, while the short strand of the partial duplex adapter does not comprise cytosine analog residues in place of cytosine residues. In some cases, the short strand of a partial duplex adapter comprises cytosine analog residues in place of cytosine residues, which are protected from bisulfite conversion, while the long strand of the partial duplex adapter does not comprise cytosine analog residues in place of cytosine residues. In some cases, both the long and short strand of a partial duplex adapter comprises cytosine analog residues in place of cytosine residues. In some cases, the cytosine analog is 5-methylcytosine. In some cases, the cytosine analog is 5-hydroxymethylcytosine. In some cases, the cytosine analog is 5-propynylcytosine. A strand can comprise a modified cytosine at about, more than, less than, or at least every 1, 2, 3, 4, 5, 6, 7, 8, 9, 10, 15, 20, 25, 30, 40, 50, 65, 75, 85, 90, 95, 100, 110, 120, 130, 140, 150, 160, 170, 180, 190, 200, 225, or 250 nucleotides. In some cases, ligation of an adapter to a double stranded polynucleotide is by blunt end ligation. In some cases, ligation of an adapter to a double stranded polynucleotide is by cohesive or sticky end ligation, wherein an overhang in the adapter hybridizes to an overhang in the double stranded polynucleotide comprising complementary sequence. In some cases, an adapter comprising a modified dNTP (e.g. a cytosine analog resistant to bisulfite treatment) comprises a ligation strand or first strand capable of ligation to a 5'end of the polynucleotide fragments and a non-ligation strand or second strand incapable of ligation to either end of the polynucleotide fragments. In some cases, the duplex adapter is a partial duplex adapter, wherein the adapter comprises a long strand and a short strand, and wherein the long strand is the ligation strand or first strand, while the short strand is the non-ligation strand or second strand. In some cases, the partial duplex has strands of unequal length. In some cases, the partial duplex comprises an overhang at one end of the adapter and a blunt end at another end of the adapter. The overhang can be at the 3' end or the 5' end. In some cases, the partial duplex comprises an overhang at each end of the adapter. The overhang can be of equal length or unequal length. In some cases, the 5' end of the ligation strand does not comprise a 5' phosphate group. In some cases, the 5' end of the ligation strand does comprise a 5' phosphate, wherein the 3' end of the polynucleotide lacks a free 3' hydroxyl.

In some cases, the 3' and/or 5' ends of the non-ligation strand comprise a blocking group and are enzymatically unreactive. The blocking group can be a dideoxynucleotide (ddCMP, ddAMP, ddTMP, or ddGMP), various modified nucleotides (e.g. phosphorothioate-modified nucleotides), or non-nucleotide chemical moieties. In some cases, the blocking group comprises a nucleotide analog that comprises a blocking moiety. The blocking moiety can mean a part of the nucleotide analog that inhibits or prevents the nucleotide analog from forming a covalent linkage to a second nucleotide or nucleotide analog. For example, in the case of nucleotide analogs having a pentose moiety, a reversible blocking moiety can prevent formation of a phosphodiester bond between the 3' oxygen of the nucleotide and the 5' phosphate of the second nucleotide. Reversible blocking moieties can include phosphates, phosphodiesters, phosphotriesters, phosphorothioate esters, and carbon esters. In some cases, a blocking moiety can be attached to the 3' position or 2' position of a pentose moiety of a nucleotide analog. A reversible blocking moiety can be removed with a deblocking agent. The 3' end of the non-ligation strand can be modified to comprise a blocking group, for example, a dideoxynucleotide (ddCMP, ddAMP, ddTMP, or ddGMP) to prevent polymerase extension. The blocking group at the 3' end of the non-ligation strand can be a nucleotide terminator. In some cases, the block at the 3' end of the non-ligation strand comprises a terminal dideoxycytosine. The 5' end of the non-ligation strand can be modified to comprise a blocking group. The blocking group at the 5' end of the non-ligation strand can be a spacer (C3 phosphoramidite, triethylene glycol (TEG), photo-cleavable, hexa-ethyleneglycol), inverted dideoxy-T, biotin, thiol, dithiol, hexanediol, digoxigenin, an azide, alkynes, or an amino modifier. The biotin blocking group can be photocleavable biotin, biotin-triethylene glycol (TEG), biotin-dT, desthiobiotin-TEG, biotin-azide, or dual biotin. In some cases, the block at the 5' end of the non-ligation strand comprises a biotin moiety. In some cases, the 5' end of the non-ligation strand does not comprise a 5' phosphate. The 5' end can be removed by treatment with an enzyme. The enzyme can be a phosphatase. In some cases, the 5' end of the non-ligation strand is dephosphorylated by treatment with alkaline phosphatase. In some cases, the 5' end of the non-ligation strand does comprise a 5' phosphate, wherein the 3' end of the polynucleotide lacks a free 3' hydroxyl. In some cases, the non-ligation strand comprises a block at the 3' end comprising terminal dideoxycytosine and a block at the 5' end comprising a biotin moiety. In some cases, distinct adapters as described herein are ligated to a 5' end of a double strand polynucleotide.

In some cases, the adapter is a hairpin adapter comprising a stem-loop, wherein both strands of the stem comprise a modified dNTP (e.g. a cytosine analog resistant to bisulfite treatment). In some cases, the stem-loop adapter comprises a ligation or first strand and a non-ligation or second strand as described herein. In some cases, the 3' end of the stem comprises the ligation strand, while the 5' end of the stem comprises the non-ligation strand. In some cases, the 5' end of the stem does not comprise a 5' phosphate. In some cases, the 5' end of the stem comprises a 5' phosphate, while the 3' ends of the double strand polynucleotide lacks a free 3' hydroxyl. In some cases, the 5' end of the stem comprises a blocking group. The blocking group can be any of the blocking groups described herein. In some cases, the stem comprises an overhang. The overhang can be a 5' overhang or a 3' overhang and can comprise DNA, RNA, or both. A stem-loop adapter can be ligated to a double stranded polynucleotide by the methods described herein. In some cases, a stem loop adapter comprises a replication block. The replication block can be a non-replicable base or region in the loop or in a region of the stem adjacent to the loop comprising abasic sites. The replication block can comprise an inverted repeat. Abasic sites can be generated in the stem-loop by any of the methods known in the art, which can include, but is not limited to, incorporation of dUTP during generating of the adapter followed by treatment with dU-glycosylase (which is also referred to as Uracyl-DNA Glycosylase or UDC). In some cases, the replication block is removable or cleavable.

In some cases, the adapter comprises a ligation or first strand as described herein, and a non-ligation or second strand, wherein the non-ligation or second strand comprises RNA residues. In some cases, the adapter comprises a ligation or first strand as described herein, and a non-ligation or second strand, wherein the ligation or first strand comprises RNA residues.

In some cases, the ligation of an adapter to a first strand of a double stranded polynucleotide fragments creates a nick or break in the backbone between the non-ligation strand of the adapter and the 3' end of the second strand of the double-stranded polynucleotide fragments, wherein the non-ligation strand is not joined to the 3' end of the second strand of the polynucleotide fragments. In this case, the 5' end of the ligation strand does not comprise a 5' phosphate group. Further to this case, ligation of an adapter to the polynucleotide fragment can generate a polynucleotide fragment comprising the ligation strand comprising a cytosine analog joined to a first and second 5' end of the polynucleotide fragments. In some cases, the 5' end of the ligation strand comprises a 5' phosphate group, and the 3' ends of the polynucleotide fragment lacks a free 3' hydroxyl. Further to this case, ligation of an adapter to the polynucleotide fragment can generate a polynucleotide fragment comprising the ligation strand comprising a cytosine analog joined to a first and second 5' end of the polynucleotide fragments. In some cases, the ligation strand comprising a cytosine analog of distinct adapters are joined to a first and second 5' end of the double stranded polynucleotide fragments.

The method can further comprise performing an extension reaction. The extension reaction can be performed using any number of methods known in the art including, but not limited to, the use of a DNA dependent DNA polymerase with strand displacement activity and all four dNTPs (i.e. dATP, dTTP, dCTP, and dGTP), wherein the dNTPs are unmodified. In some cases, the extension reaction is performed with a DNA polymerase and unmodified dNTPs (i.e. dATP, dTTP, dCTP, and dGTP). In some cases, the extension reaction extends the 3' ends of the polynucleotide fragments, whereby a non-ligation strand of an adapter is removed. The non-ligation strand can be removed by being displaced, degraded, or denatured. In some cases, the non-ligation strand of the joined adapter is removed by heat denaturation, and the 3' ends of the polynucleotide fragment are extended with a polymerase without strand displacement activity. In some cases, the melting temperature of the non-ligation strand bound to the ligation strand can be lower than the melting temperature of the two strands of the polynucleotide fragment to which the ligation strand of the adapter is joined. In some cases, the non-ligation strand is displaced by a polymerase comprising strand displacement activity during extension of the 3' ends of the double stranded polynucleotide fragment. In some cases, the adapter is a hairpin adapter and the extension reaction displaces the non-ligation strand of the stem. In some cases, the displaced strand of the stem adapter remains connected to the ligation strand of the stem via the loop. In some cases, the loop comprises a cleavage site for an enzyme (i.e. restriction endonuclease). In some cases, the cleavage site is within a replication block. In some cases, the cleavage site is cleaved, thereby removing the non-ligation strand of the stem. In these cases, the ligation strand of the stem comprises the modified nucleotide (i.e. nucleotide with cytosine analog resistant to bisulfite treatment). In some cases, the ligation strand serves as the template, wherein the extension reaction generates sequence complementary to the ligation strand. In some cases a single adapter is ligated to the 5' ends of the double stranded polynucleotide fragment, whereby extension of the 3' ends of the polynucleotide fragment generates polynucleotide fragments comprising complementary adapter sequences at the 3' and 5' ends. In some cases, distinct adapters are ligated to the 5' ends of the double stranded polynucleotide fragment, whereby extension of the 3' ends of the polynucleotide fragment generates polynucleotide fragments comprising distinct adapter sequences at the 3' and 5' ends of each strand. Further to this case, the ligation strands of the distinct adapters can comprise a modified dNTP (i.e. modified dCTP comprising a cyotsine analog resistant to bisulfite treatment). In some cases, the adapter ligated to the polynucleotide fragments comprises a non-ligation strand comprising RNA thereby forming a DNA/RNA heteroduplex with the ligation strand, wherein the extension reaction extends the 3' ends of the polynucleotide fragments following degradation of the RNA in the non-ligation strand using an agent capable of degrading RNA in a DNA/RNA heteroduplex. The agent can be an enzyme. The enzyme can be RNase H. In this embodiment, the ligation or first strand serves as the template, wherein the extension reaction generates sequence complementary to the ligation or first strand, thereby generating polynucleotide fragments comprising complementary adapter sequences at the 3' and 5' ends.

In some cases, the duplex adapter is a partial duplex adapter, wherein the adapter comprises a long strand and a short strand, wherein both the long strand and the short strand are capable of ligation. In some cases, the long strand comprises a modified dNTP (e.g. a cytosine analog resistant to bisulfite treatment). In some cases, the short strand comprises a modified dNTP (e.g. a cytosine analog resistant to bisulfite treatment). In these cases, the partial duplex adapter comprises a 5' overhang and a blunt end, or both a 5' and 3' overhang. In order to reduce the formation of primer dimers, the 3' end of the short arm of the adapter can comprise a blocking group and can be enzymatically unreactive. The blocking group can be any of the blocking groups described herein. In some cases, the short arm of the adapter comprises a reversible blocking group, wherein the reversible blocking group can be removed following ligation of the adapter to the double stranded polynucleotide. In some cases, unligated adapter is removed by washing and/or degradation following ligation and prior to removal of the reversible blocking group. In some cases, the method can further comprise performing an extension reaction. The extension reaction can be performed using any number of methods known in the art including, but not limited to, the use of a DNA dependent DNA polymerase with strand displacement activity and all four dNTPs (i.e. dATP, dTTP, dCTP, and dGTP), wherein the dNTPs are unmodified. In some cases, the extension reaction is performed with a DNA polymerase and unmodified dNTPs (i.e. dATP, dTTP, dCTP, and dGTP). In some cases, the extension reaction extends the 3' ends of short strand of the adapters ligated to the ends of the double stranded polynucleotide fragments, thereby generating polynucleotide fragments comprising complementary adapter sequences at the 3' and 5' ends In some cases, double stranded polynucleotide fragments comprising adapter sequence at the 3' and 5' ends are captured prior to treatment with a converting agent. In some cases, the double stranded polynucleotide fragments are captured using a binding agent directed against modified dNTPs in the double-stranded polynucleotide fragments with adapters. The modified dNTP can be a modified dCTP comprising a cytosine analog. The cytosine analog can be 5-methylcytosine, 5-hydroxymethylcytosine or 5-propynylcytosine. The binding agent can be an antibody, or the binding domain of a protein directed against a cytosine analog. In some cases, the binding domain is directed against 5-methylcytosine residues. The binding domain can be from a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2. In some cases, one or both strands of the adapter sequence on the end(s) of the double stranded polynucleotide fragments comprise a cytosine analog other than 5-methylcytosine, wherein the double stranded polynucleotide fragments are captured using the binding domain of a methyl-CpG-binding domain (i.e. MBD2 or MECP2). The cytosine analog other than 5-methylcytosine can be 5-hydroxymethylcytosine or 5-propynylcytosine.

In some cases, the method further comprises a denaturing step, wherein the polynucleotide fragments comprising adapter sequences at the 3' and 5' ends are denatured. Denaturation can be achieved using any of the methods known in the art which can include, but are not limited to, heat denaturation, and/or chemical denaturation. Heat denaturation can be performed by raising the temperature of the reaction mixture to be above the melting temperature of the polynucleotide fragments comprising adapter sequence at both ends. The melting temperature can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, 85, 86, 87, 88, 89, 90, 91, 92, 93, 94, or 95 degrees C. The temperature can be raised above the melting temperature by about, more than, less than, or at least 1, 2, 3, 4, 5, 6, 7, 8, 9, or 10 degrees C. Chemical denaturation can be performed using bases (i.e. NaOH), and/or competitive denaturants (i.e. urea, or formaldehyde). In some cases, denaturation generates single stranded polynucleotides fragments comprising complementary adapter sequence at the 3' and 5' ends. In some cases, denaturation generates single stranded polynucleotides fragments comprising distinct adapter sequence at the 3' and 5' ends.

In some cases, single stranded polynucleotide fragments comprising adapter sequence at the 3' and 5' ends are captured prior to treatment with a converting agent. In some cases, the polynucleotide fragments are captured by a binding agent directed against one or more modified dNTPs present in the adapter sequence. In some cases, the modified dNTP is a nucleotide base analog. In some cases, the binding agent is a binding protein. In some cases, the binding protein is an antibody directed against the modified dNTP. In some cases, the binding protein is an antibody directed against the modified dNTP, wherein the modified dNTP is a nucleotide analog. In some cases, the single stranded polynucleotide fragments comprising adapter sequence at the 3' and 5' ends are captured prior to treatment with a bisulfite. In some cases, the nucleic acid fragments (polynucleotides) are captured by a binding agent directed against one or more elements present in the adapter sequence. In some cases, the one or more elements comprise a cytosine analog. In some cases, the cytosine analog is 5-methylcytosine. In some cases, the binding agent is a 5-methylcytosine binding protein. In some cases, the binding protein is an anti-5-methylcytosine antibody. In some cases, 5-methylcytosine capture is performed prior to bisulfite treatment, wherein the cytosine analog resistant to bisulfite treatment is a cytosine analog other than 5-methylcytosine. In some cases, the cytosine analog can be 5-hydroxymethylcytosine or 5-propynylcytosine. The one or more elements can be introduced during the extension reaction. In some cases a modified nucleotide can be incorporated during the extension reaction, wherein the modified nucleotide contains a tag. The tag can be a biotin moiety. In some cases, the binding agent is avidin, streptavidin, or an anti-biotin antibody.

Following denaturation, and optional capture by a binding agent, the single-stranded polynucleotide fragments comprising adapter sequence at the 3' and 5' ends can be treated with a converting agent. In some cases, treatment of the single-stranded polynucleotide fragments with a converting agent alters the sequence of the complement of the ligation strand as well as the first and second strands of the double stranded polynucleotide fragment, while leaving the sequence of the ligation or first strand unchanged. In some cases, a single adapter is ligated to the 5' ends of the polynucleotide fragments, whereby treatment with a converting agent generates single stranded polynucleotide fragments comprising non-complementary sequence at the 5' and 3' ends. In some cases, distinct adapters are ligated to the 5' ends of the polynucleotide fragments, whereby treatment with a converting agent generates single stranded polynucleotide fragments wherein the non-ligation strands of the distinct adapters is altered to be non-complementary to the ligation strands of the distinct adapters. In some embodiments, the sequence of the ligation or first strand of the adapter marks the 5' end of the polynucleotide fragments, thereby maintaining the strandedness of the polynucleotide fragment and thus providing information on directionality.

In some cases, the single-stranded nucleic acid fragments are treated with a converting agent wherein the converting agent is bisulfite. In some cases, treatment of the single-stranded polynucleotide fragments converts cytosine residues in the polynucleotide fragment and the complement of the ligation or first strand to uracil residues while the cytosine analogs in the ligation or first strand are resistant to conversion. In some cases, treatment of the single stranded polynucleotide fragments with bisulfite generates single stranded polynucleotide fragments comprising non-complementary adapter sequence at the 5' and 3' ends. In some cases, the sequence of the ligation strand of the adapter unaltered by bisulfite treatment marks the 5' end of the polynucleotide fragments, thereby maintaining the strandedness of the polynucleotide fragment and thus providing information on directionality. In some cases, distinct adapters are ligated to the 5' ends of the polynucleotide fragments, whereby treatment with a bisulfite generates single stranded polynucleotide fragments wherein cytosine residues in the non-ligation strands of the distinct adapters are converted to uracil residues, whereby the sequence of the non-ligation strand is no longer complementary to the ligation strands of the distinct adapters.

In some cases, the method further comprises amplifying the single-stranded polynucleotide fragments comprising adapter sequences at the 3' and 5' ends. In some cases, amplification of the single-stranded polynucleotide fragments comprising adapter sequence at the 3' and 5' ends generates directional polynucleotide libraries. In some cases, one end of the polynucleotide fragment marks the orientation of the original polynucleotide strand to which it is appended due to its resistance to conversion by the converting agent, whereby the sequence in said end is resistant to conversion to a different sequence by treatment with the converting agent. In some cases, amplification of the single-stranded polynucleotide fragments comprising adapter sequence at the 3' and 5' ends generates directional polynucleotide libraries wherein one end of the polynucleotide fragments marks the orientation of the original polynucleotide strand to which it is appended due to its resistance to conversion by bisulfite treatment. In some cases, the cytosine residues present in said end are resistant to conversion to uracil residues by bisulfite treatment In some cases, amplifying the single stranded polynucleotide fragments comprising adapter sequence at the 3' and 5' ends comprises the use of a first primer and a second primer. In some cases, the first primer is directed against sequence complementary to the ligation or first strand of an adapter altered following treatment with a converting agent. In some cases, the second primer is directed against sequence complementary to the ligation or first strand of an adapter, wherein the ligation or first strand to which said complementary sequence is complementary is not altered by treatment with the converting agent. In some cases, the converting agent is bisulfite, whereby treatment with bisulfite converts cytosine residues in the sequence complementary to the ligation or first strand to uracil residues. In some cases, the first primer is directed against sequence complementary to the ligation or first strand of the adapter comprising uracil residues following bisulfite treatment. In some cases, the second primer is directed against sequence complementary to the ligation or first strand of the adapter, wherein the ligation or first strand to which said complementary sequence is complementary to does not contain uracil residues following bisulfite treatment. The single stranded polynucleotide fragments comprising adapter sequence at the 3' and 5' ends can represent a first strand of a double stranded polynucleotide fragment or a second strand of a double stranded polynucleotide fragment. In some cases, a single adapter is ligated to the 5' ends of the polynucleotide, whereby the first and second strands can comprise non-complementary sequence following treatment with the converting agent (i.e. bisulfite treatment). In some cases, distinct adapters are ligated to the 5' ends of the polynucleotide fragments, whereby treatment with bisulfite generates single stranded polynucleotide fragments from a first strand of a double stranded polynucleotide fragment or a second strand of a double stranded polynucleotide fragment, wherein cytosine residues in the non-ligation strands of the distinct adapters are converted to uracil residues. In these cases, the sequence of the non-ligation strand is no longer complementary to the ligation strands of the distinct adapters. Amplifying the single stranded polynucleotide fragments comprising adapter sequence at the 3' and 5' ends can produce amplification products from either or both of the first and second strand of the double stranded polynucleotide fragment following treatment with the converting agent (i.e. bisulfite). In some cases, the first and/or second primer further comprises one or more identifier sequences. In some cases, the identifier sequences comprise a non-hybridizable tail on the first and/or second primer. The identifier sequence can be a barcode sequence, a flow cell sequence, and/or an index sequence. In some cases, the index sequence is a Truseq primer sequence compatible with the next generation sequencing platform produced by Illumina. In some cases, the first and/or second primer can bind to a solid surface. The solid surface can be a planar surface or a bead. The planar surface can be the surface of a chip, microarray, well, or flow cell. In some cases, the first and/or second primer comprises one or more sequence elements products of the amplification reaction (i.e. amplification products) to a solid surface, wherein the one or more sequences are complementary to one or more capture probes attached to a solid surface.

In some cases, methods for generating a polynucleotide library using modified duplex-forming adapters described herein further comprise determining the methylation status of the input double stranded polynucleotide. In some cases, the input polynucleotide is genomic DNA and the amplification of single-stranded polynucleotide fragments comprising non-complementary sequence at the 3' and 5' ends is followed by sequencing. Further to this embodiment, the methylation status of the genomic DNA can be determined by comparing the sequence obtained from the sequencing of the single-stranded polynucleotide fragments comprising non-complementary sequence at the 3' and 5' ends representing either or both of the first and second strand of the double stranded polynucleotide following treatment with converting agent (i.e. bisulfite treatment) generated by the methods described herein against a reference sequence. The reference sequence can be the sequence of the genomic DNA (either or both strands) not subjected to alteration by treatment with the converting agent. The comparing can be performed on a computer. The comparing can be done on a computer using a sequence alignment tool or program. The sequence alignment tool or program can map bisulfite treated sequencing reads to a genome of interest and perform methylation calls. The bisulfite sequencing mapping tool can be the Bismark program. In some cases, the comparing comprises performing a nucleotide alignment between the sequence obtained from the sequencing of the single-stranded DNA fragments comprising non-complementary sequence at the 3' and 5' ends generated by the methods described herein with a reference sequence on a computer using any of the nucleotide alignment programs known in the art (e.g. Bismark). In some cases, the methods described herein can be used to determine the methylation status of a specific locus or region of genomic DNA or the entire genome (i.e. the methylome). In some cases, following bisulfite treatment, the methylation status of a given cytosine residue is inferred by comparing the sequence to an unmodified reference sequence.

Sequencing can be any method of sequencing, including any of the next generation sequencing (NGS) methods described herein. In some cases, the NGS method comprises sequencing by synthesis. In some embodiments, sequencing is performed with primers directed against known or universal sequence introduced into the nucleic acid fragments by the adapter ligated to the nucleic acid fragments. In some cases, the primers used for sequencing are directed against adapter sequence unaltered by treatment with a converting agent. In some cases, primers used for sequencing are directed against adapter sequence altered by treatment with a converting agent. The converting agent can be bisulfite, wherein bisulfite treatment converts cytosine residues to uracil residues. In some cases, the sequencing primers are directed against adapter sequence comprising thymine residues following bisulfite treatment and amplification. In some cases, the sequencing primers are directed against adapter sequence wherein the adapter sequence is resistant to conversion by bisulfite treatment. In this embodiment, the adapter sequence to which the sequencing primers are directed does not comprise thymine residues following bisulfite treatment and amplification. In some cases, sequencing is performed with primers directed against identifier sequence introduced into the polynucleotide fragments by the first and/or second primer used to amplify single-stranded polynucleotide fragments comprising non-complementary sequence at the 3' and 5' ends. The identifier sequence can be a barcode sequence, a flow cell sequence, and/or index sequence. In some cases, the index sequence is a Truseq primer sequence compatible with the next generation sequencing platform produced by Illumina.

A schematic exemplary of an embodiment of the methods described herein for generating a directional, bisulfite converted library using modified partial duplex-forming adapters is shown in FIG. 1. As illustrated in FIG. 1, an adapter is ligated to a 5' end on each strand of a double stranded polynucleotide fragment. The 5' ends of the double stranded polynucleotide fragments comprise 5' phosphates, whereas the adapter does not comprise 5' phosphates. The adapter is a partial duplex adapter, wherein the partial duplex comprises a long arm comprising forward adapter sequence hybridized to a short arm, wherein the short arm of the adapter hybridizes to the 3' portion of the long arm of the adapter to produce a blunt end. All the cytosine residues in the long arm of the partial duplex adapter are 5-methylcytosine residues, and both the 5' and 3' ends of the short arm are blocked such that neither end is enzymatically reactive. Thus, the long arm of the adapter serves as the ligation strand, while the short arm of the adapter serves as the non-ligation strand. Following ligation, the long arm of the adapter is joined to the 5'end of each of the strands of the double stranded polynucleotide fragment, while a nick exists between the 3' end of each of the strands of the double stranded polynucleotide fragments and the short arm of the two adapters. The nick is filled in using a DNA polymerase, wherein the 3' ends of the double stranded polynucleotide fragment are extended using the long arm of the adapter as template, displacing the short arm of the adapter. Following the extension, the double stranded polynucleotide fragments are denatured, thereby generating single stranded polynucleotide fragments comprising the ligation strand (i.e. the long arm of the adapter comprising 5-methylcytosine(s)) at the 5' end and the complement of the ligation strand at the 3' end, wherein the complement of the ligation strand comprises unmodified cytosine residues. The single-stranded polynucleotide fragments are then subjected to bisulfite treatment by any of the methods known in the art, wherein 5-methylcytosine residues are left intact, while cytosine residues are converted to the base uracil. Thus, bisulfite treatment generates single stranded polynucleotide fragments comprising non-complementary adapter sequences at each end, wherein the 5' end comprises the ligation strand comprising non-converted 5-methylcytosine residues, while the 3' end comprises the complement of the ligation strand wherein the cytosine residues are converted to uracil. The single-stranded polynucleotide fragments further comprise polynucleotide sequence between the non-complementary ends, wherein cytosine residues within the polynucleotide sequence have been converted to uracil residues following bisulfite treatment. The single stranded polynucleotide fragments are then amplified (i.e. via PCR) using the primer pair (P1/P2) shown in FIG. 1. The P2 primer comprises at least of portion of the sequence of the ligation strand, wherein the sequence compensates for the conversion of cytosine to uracil following bisulfite treatment in the sequence such that adenine bases are present within the P2 primer in order to base pair with uracil bases generated following bisulfite treatment. As shown in FIG. 1, the P2 primer further comprises a non-hybridizable tail, wherein the tail comprises a reverse flow cell sequence, a TruSeq primer sequence or a second read barcode sequence, and optional barcode sequence. The optional barcode sequence can be added for embodiments whereby barcoded libraries are generated. The P1 primer comprises a non-hybridizable tail portion comprising a forward flow cell sequence and a hybridizable portion comprising at least a portion of the ligation strand sequence, wherein the base composition has not been altered by bisulfite treatment (i.e. the sequence represents ligation strand sequence prior to bisulfite treatment). Following amplification with the P1/P2 primers, an amplification product comprising double stranded polynucleotide sequence appended with non-complementary adapter sequence at each end derived from the ligated adapter and flow cell sequences as depicted in FIG. 1 are generated. The amplification products are compatible with the next generation sequencing platform developed by Illumina via the flow cell and Truseq primer sequences introduced during amplification and can be sequenced using sequencing primers directed against sequence present in the sequence appended to each end of the input polynucleotide sequence following ligation, bisulfite treatment, and amplification. Sequencing is performed using a standard read primer directed against at least a portion of the forward adapter sequence and a custom second read sequencing primer directed against the adapter sequence whose sequence has been altered by bisulfite treatment adapter sequence. The methylation status of the input double stranded polynucleotide is determined by comparing the sequence of the input polynucleotide within the amplification product to the sequence of the original input polynucleotide.

V. Generating a Directional Library Using Unmodified Duplex-Forming Adapters

In another aspect, a method for generating a directional, bisulfite-converted polynucleotide library using unmodified duplex-forming adapters is provided. A polynucleotide library generated using unmodified duplex-forming adapters can maintain directional (strandedness) information of the original polynucleotide sample. In some cases, the polynucleotide is DNA. In some cases, the DNA is double-stranded DNA. In some cases, the double-stranded DNA is genomic DNA. In some cases, the DNA is cDNA. In some cases, the cDNA is double-stranded cDNA.

The method can comprise fragmenting a double stranded polynucleotide to produce double stranded polynucleotide fragments. In some cases, fragmentation can be achieved through methods known in the art. Fragmentation can be through physical fragmentation methods and/or enzymatic fragmentation methods. Physical fragmentation methods can include nebulization, sonication, and/or hydrodynamic shearing. In some cases, the fragmentation can be accomplished mechanically comprising subjecting the nucleic acid to acoustic sonication. In some cases, the fragmentation comprises treating the nucleic acid with one or more enzymes under conditions suitable for the one or more enzymes to generate breaks in the double-stranded nucleic acid. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g, from New England Biolabs). For example, digestion with DNase I can induce random double-stranded breaks in DNA in the absence of $Mg^{++}$ and in the presence of $Mn^{++}$. In some cases, fragmentation comprises treating DNA with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the DNA leaves overhangs having a predictable sequence. In some cases, the method includes the step of size selecting the fragments via standard methods known in the art such as column purification or isolation from an agarose gel.

In some cases, the polynucleotide, for example DNA, can be fragmented into a population of fragmented polynucleotides of one or more specific size range(s). In some cases, the fragments can have an average length from about 10 to about 10,000 nucleotides or base pairs. In some cases, the fragments have an average length from about 50 to about 2,000 nucleotides or base pairs. In some cases, the fragments have an average length from about 100 to about 2,500, about 10 to about 1000, about 10 to about 800, about 10 to about 500, about 50 to about 500, about 50 to about 250, or about 50 to about 150 nucleotides or base pairs. In some cases, the fragments have an average length less than 10,000 nucleotides or bp, less than 7,500 nucleotides or bp, less than 5,000 nucleotides or bp, less than 2,500 nucleotides or bp, less than 2,000 nucleotides or bp, less than 1,500 nucleotides or bp, less than 1,000 nucleotides or bp, less than 500 nucleotides or bp, less than 400 nucleotides or bp, less than 300 nucleotides or bp, less than 200 nucleotides or bp, or less than 150 nucleotides or bp. In some cases, the polynucleotide fragments have an average length of about, more than, less than, or at least 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 nucleotides or base pairs in length In some cases, the polynucleotide fragments generated by fragmentation are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the double stranded nucleic acid fragments to produce blunt ends wherein the ends of the polynucleotide fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, double stranded polynucleotide fragments are captured using a binding agent directed against an epigenetic modification within the sequence of the polynucleotide fragments. The epigenetic modification can be methylation. In some cases, the double stranded polynucleotide fragments are captured using a binding agent directed against 5-methylcytosine residues in the double-stranded polynucleotide fragments. The binding agent can be an antibody, or the binding domain of a protein directed against 5-methylcytosine residues. The protein can be a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2.

The method can further comprise ligating an adapter to the double-stranded polynucleotide fragments. Ligation can be blunt end ligation or sticky or cohesive end ligation. The ligation can be performed with any of the enzymes known in the art for performing ligation (e.g. T4 DNA ligase). The adapter can be any type of adapter known in the art including, but not limited to, a conventional duplex or double stranded adapter. The adapter can comprise DNA, RNA, or a combination thereof. The adapters can be about, less than about, or more than about 10, 15, 20, 25, 30, 35, 40, 45, 50, 55, 60, 65, 70, 75, 80, 90, 100, or 200 nucleotides in length. The adapters can be a duplex adapter, partial duplex adapter, or single stranded adapter. In some cases, the adapter is a duplex adapter. In some cases, the duplex adapters comprises about, less than about, or more than about 10, 15, 20, 25, 30, 35, 40, 45, 50, 55, 60, 65, 70, 75, 80, 90, 100, or 200 nucleotides in length. In some cases, the adapter is a partial duplex adapter, wherein the adapter comprises a long strand and a short strand. In some cases, a partial duplex adapter has overhangs of about, more than, less than, or at least 1, 2, 3, 4, 5, 6, 7, 8, 9, 10, 11, 12, 13, 14, 15, 16, 17, 18, 19, or 20 nucleotides. In some cases, the overhang is a 5' overhang. In some cases, the overhang is a 3' overhang. In some cases, the partial duplex adapter comprises a 5' and 3' overhang. In some cases, the adapter comprises duplexed sequence. In some cases, the adapters comprise about, more than, less than, or at least 5, 6, 7, 8, 9, 10, 12, 12, 13, 14, 15, 16, 17, 18, 19, 20, 21, 22, 23, 24, 25, 30, 35, 40, 45, 50, 55, 60, 65, 70, 75, 80, 90, 100, 200, or more of base paired or duplexed sequence. In some cases, the adapter comprises a single stranded adapter. In some cases, a single-stranded adapter comprises about, more than, less than, or at least 10, 15, 20, 25, 30, 35, 40, 45, 50, 55, 60, 65, 70, 75, 80, 90, 100, or 200 nucleotides in length. In some cases, the single-stranded adapter forms a stem-loop or hairpin structure. In some cases, the stem of the hairpin adapter is about, less than about, or more than about 1, 2, 3, 4, 5, 6, 7, 8, 9, 10, 11, 12, 13, 14, 15, 20, 25, 30, 35, 40, 45, 50, 75, 100, or more nucleotides in length. In some cases, the loop sequence of a hairpin adapter is about, less than about, or more than about 5, 10, 15, 20, 25, 30, 35, 40, 45, 50, or more nucleotides in length. The adapter can further comprise known or universal sequence and, thus, allow generation and/or use of sequence specific primers for the universal or known sequence. In some cases, an adapter comprises a barcode.

In some cases, ligation of an adapter to a double stranded polynucleotide is by blunt end ligation. In some cases, ligation of an adapter to a double stranded polynucleotide is by cohesive or sticky end ligation, wherein an overhang in the adapter hybridizes to an overhang in the double stranded polynucleotide comprising complementary sequence. In some cases, an adapter comprises a ligation strand or first strand capable of ligation to a 5'end of the polynucleotide fragments and a non-ligation strand or second strand incapable of ligation to either end of the polynucleotide fragments. In some cases, the duplex adapter is a partial duplex adapter, wherein the adapter comprises a long strand and a short strand, and wherein the long strand is the ligation strand or first strand, while the short strand is the non-ligation strand or second strand. In some cases, the partial duplex has strands of unequal length. In some cases, the partial duplex comprises an overhang at one end of the adapter and a blunt end at another end of the adapter. The overhang can be at the 3' end or the 5' end. In some cases, the partial duplex comprises an overhang at each end of the adapter. The overhang can be of equal length or unequal length. In some cases, the 5' end of the ligation strand does not comprise a 5' phosphate group. In some cases, the 5' end of the ligation strand does comprise a 5' phosphate, wherein the 3' end of the polynucleotide lacks a free 3' hydroxyl.

In some cases, the 3' and/or 5' ends of the non-ligation strand comprise a blocking group and are enzymatically unreactive. The blocking group can be a dideoxynucleotide (ddCMP, ddAMP, ddTMP, or ddGMP), various modified nucleotides (e.g. phosphorothioate-modified nucleotides), or non-nucleotide chemical moieties. In some cases, the blocking group comprises a nucleotide analog that comprises a blocking moiety. The blocking moiety can mean a part of the nucleotide analog that inhibits or prevents the nucleotide analog from forming a covalent linkage to a second nucleotide or nucleotide analog. For example, in the case of nucleotide analogs having a pentose moiety, a reversible blocking moiety can prevent formation of a phosphodiester bond between the 3' oxygen of the nucleotide and the 5' phosphate of the second nucleotide. Reversible blocking moieties can include phosphates, phosphodiesters, phosphotriesters, phosphorothioate esters, and carbon esters. In some cases, a blocking moiety can be attached to the 3' position or 2' position of a pentose moiety of a nucleotide analog. A reversible blocking moiety can be removed with a deblocking agent. The 3' end of the non-ligation strand can be modified to comprise a blocking group, for example, a dideoxynucleotide (ddCMP, ddAMP, ddTMP, or ddGMP) to prevent polymerase extension. The blocking group at the 3' end of the non-ligation strand can be a nucleotide terminator. In some cases, the block at the 3' end of the non-ligation strand comprises a terminal dideoxycytosine. The 5' end of the non-ligation strand can be modified to comprise a blocking group. The blocking group at the 5' end of the non-ligation strand can be a spacer (C3 phosphoramidite, triethylene glycol (TEG), photo-cleavable, hexa-ethyleneglycol), inverted dideoxy-T, biotin, thiol, dithiol, hexanediol, digoxigenin, an azide, alkynes, or an amino modifier. The biotin blocking group can be photocleavable biotin, biotin-triethylene glycol (TEG), biotin-dT, desthiobiotin-TEG, biotin-azide, or dual biotin. In some cases, the block at the 5' end of the non-ligation strand comprises a biotin moiety. In some cases, the 5' end of the non-ligation strand does not comprise a 5' phosphate. The 5' end can be removed by treatment with an enzyme. The enzyme can be a phosphatase. In some cases, the 5' end of the non-ligation strand is dephosphorylated by treatment with alkaline phosphatase. In some cases, the 5' end of the non-ligation strand does comprise a 5' phosphate, wherein the 3' end of the polynucleotide lacks a free 3' hydroxyl. In some cases, the non-ligation strand comprises a block at the 3' end comprising terminal dideoxycytosine and a block at the 5' end comprising a biotin moiety. In some cases, distinct adapters as described herein are ligated to a 5' end of a double strand polynucleotide.

In some cases, the adapter is a hairpin adapter comprising a stem-loop. In some cases, the stem-loop adapter comprises a ligation or first strand and a non-ligation or second strand as described herein. In some cases, the 3' end of the stem comprises the ligation strand, while the 5' end of the stem comprises the non-ligation strand. In some cases, the 5' end of the stem does not comprise a 5' phosphate. In some cases, the 5' end of the stem comprises a 5' phosphate, while the 3' ends of the double strand polynucleotide lacks a free 3' hydroxyl. In some cases, the 5' end of the stem comprises a blocking group. The blocking group can be any of the blocking groups described herein. In some cases, the stem comprises an overhang. The overhang can be a 5' overhang or a 3' overhang. The stem-loop adapter can be ligated to a double stranded polynucleotide by the methods described herein. In some cases, the stem loop adapter comprises a replication block. The replication block can be a non-replicable base or region in the loop or in a region of the stem adjacent to the loop comprising abasic sites. The replication block can comprise an inverted repeat. Abasic sites can be generated in the stem-loop by any of the methods known in the art, which can include, but is not limited to, incorporation of dUTP during generating of the adapter followed by treatment with dU-glycosylase (which is also referred to as Uracyl-DNA Glycosylase or UDG). In some cases, the replication block is removable or cleavable.

In some cases, the adapter comprises a ligation or first strand as described herein, and a non-ligation or second strand, wherein the non-ligation or second strand comprises RNA residues. In some cases, the adapter comprises a ligation or first strand as described herein, and a non-ligation or second strand, wherein the ligation or first strand comprises RNA residues.

In some cases, the ligation of an adapter to a first strand of a double stranded polynucleotide fragments creates a nick or break in the backbone between the non-ligation strand of the adapter and the 3' end of the second strand of the double-stranded polynucleotide fragments, wherein the non-ligation strand is not joined to the 3' end of the second strand of the polynucleotide fragments. In this case, the 5' end of the ligation strand does not comprise a 5' phosphate group. Further to this case, ligation of an adapter to the polynucleotide fragment can generate a polynucleotide fragment comprising the ligation strand joined to a first and second 5' end of the polynucleotide fragments. In some cases, the 5' end of the ligation strand comprises a 5' phosphate group, and the 3' ends of the polynucleotide fragment lacks a free 3' hydroxyl. Further to this case, ligation of the adapter to the polynucleotide fragment can generate a polynucleotide fragment comprising the ligation strand joined to a first and second 5' end of the polynucleotide fragments. In some cases, the ligation strand of distinct adapters are joined to a first and second 5' end of the double stranded polynucleotide fragments.

The method can further comprise performing an extension reaction. The extension reaction can be performed using any number of methods known in the art including, but not limited to, the use of a DNA dependent DNA polymerase with strand displacement activity and dNTPs (i.e. dATP, dTTP, dCTP, and dGTP), wherein one of the dNTPs is modified. In some cases, the extension reaction is performed with a DNA polymerase, 3 unmodified dNTPs, and one modified dNTP. In some cases, the modified dNTP comprises a nucleotide analog resistant to conversion by treatment with a converting agent. The modified dNTP can be dCTP. The nucleotide analog can be a cytosine analog. In some cases, a 1:1, 1:2, 1:3, 1:4, 1:5, 1:6, 1:10, 1:15, 1:20 or higher ratio of modified to non-modified nucleotide can be used in the reaction mixture for the extension reaction. A strand can comprise a modified dNTP at about, more than, less than, or at least every 1, 2, 3, 4, 5, 6, 7, 8, 9, 10, 15, 20, 25, 30, 40, 50, 65, 75, 85, 90, 95, 100, 110, 120, 130, 140, 150, 160, 170, 180, 190, 200, 225, or 250 nucleotides. In some cases, the modified dCTP is 5-methyl-dCTP. In some cases, the modified dCTP is 5-hydroxymethyl-dCTP. In some cases, the modified dCTP is 5-propynyl-dCTP. The converting agent can be any biological, biochemical, and/or chemical agent capable of altering the base composition of a dNTP. In some cases, the converting agent is a chemical.

In some cases, the converting agent is the chemical compound bisulfite or sodium bisulfite. In some cases, the extension reaction extends the 3' ends of the polynucleotide fragments, whereby a non-ligation strand of an adapter is removed. The non-ligation strand can be removed by being displaced, degraded, or denatured. In some cases, the non-ligation strand of the joined adapter is removed by heat denaturation, and the 3' ends of the polynucleotide fragment are extended with a polymerase without strand displacement activity. In this case, the melting temperature of the non-ligation strand bound to the ligation strand is lower than the melting temperature of the two strands of the polynucleotide fragment to which the ligation strand of the adapter is joined. In some cases, the non-ligation strand is displaced by a polymerase comprising strand displacement activity during extension of the 3' ends of the double stranded polynucleotide fragment. In some cases, the adapter is a hairpin adapter and the extension reaction displaces the non-ligation strand of the stem. In some cases, the displaced strand of the stem adapter remains connected to the ligation strand of the stem via the loop. In some cases, the loop comprises a cleavage site for an enzyme (i.e. restriction endonuclease). In some cases, the cleavage site is within a replication block. In some cases, the cleavage site is cleaved, thereby removing the non-ligation strand of the stem. In these cases, the ligation strand of the stem comprises the modified nucleotide (i.e. nucleotide with cytosine analog resistant to bisulfite treatment). In some cases, the ligation strand serves as the template, wherein the extension reaction generates sequence complementary to the ligation strand. In some cases a single adapter is ligated to the 5' ends of the double stranded polynucleotide fragment, whereby extension of the 3' ends of the polynucleotide fragment generates polynucleotide fragments comprising complementary adapter sequences at the 3' and 5' ends. In some cases, distinct adapters are ligated to the 5' ends of the double stranded polynucleotide fragment, whereby extension of the 3' ends of the polynucleotide fragment generates polynucleotide fragments comprising distinct adapter sequences at the 3' and 5' ends. Further to this case, the ligation strands of the distinct adapters comprise a modified dNTP (i.e. modified dCTP comprising a cytosine analog resistant to bisulfite treatment). In some cases, the adapter ligated to the polynucleotide fragments comprises a non-ligation strand comprising RNA thereby forming a DNA/RNA heteroduplex with the ligation strand, wherein the extension reaction extends the 3' ends of the polynucleotide fragments following degradation of the RNA in the non-ligation strand using an agent capable of degrading RNA in a DNA/RNA heteroduplex. The agent can be an enzyme. The enzyme can be RNaseH. In this embodiment, the ligation or first strand serves as the template, wherein the extension reaction generates sequence complementary to the ligation or first strand, thereby generating polynucleotide fragments comprising complementary adapter sequences at the 3' and 5' ends.

In some cases, the duplex adapter is a partial duplex adapter, wherein the adapter comprises a long strand and a short strand, wherein both the long strand and the short strand are capable of ligation. In these cases, the partial duplex adapter comprises a 5' overhang and a blunt end, or both a 5' and 3' overhang. In order to reduce the formation of primer dimers, the 3' end of the short arm of the adapter can comprise a blocking group and can be enzymatically unreactive. The blocking group can be any of the blocking groups described herein. In some cases, the short arm of the adapter comprises a reversible blocking group, wherein the reversible blocking group can be removed following ligation of the adapter to the double stranded polynucleotide. In some cases, unligated adapter is removed by washing and/or degradation following ligation and prior to removal of the reversible blocking group. In some cases, the method can further comprise performing an extension reaction. The extension reaction can be performed using any number of methods known in the art including, but not limited to, the use of a DNA dependent DNA polymerase with strand displacement activity and dNTPs (i.e. dATP, dTTP, dCTP, and dGTP), wherein one of the dNTPs is modified. In some cases, the extension reaction is performed with a DNA polymerase, 3 unmodified dNTPs, and one modified dNTP. In some cases, the modified dNTP comprises a nucleotide analog resistant to conversion by treatment with a converting agent. The modified dNTP can be dCTP. The nucleotide analog can be a cytosine analog. In some cases, a 1:1, 1:2, 1:3, 1:4, 1:5, 1:6, 1:10, 1:15, 1:20 or higher ratio of modified to non-modified nucleotide can be used in the reaction mixture for the extension reaction. A strand can comprise a modified dNTP at about, more than, less than, or at least every 1, 2, 3, 4, 5, 6, 7, 8, 9, 10, 15, 20, 25, 30, 40, 50, 65, 75, 85, 90, 95, 100, 110, 120, 130, 140, 150, 160, 170, 180, 190, 200, 225, or 250 nucleotides. In some cases, the modified dCTP is 5-methyl-dCTP. In some cases, the modified dCTP is 5-hydroxymethyl-dCTP. In some cases, the modified dCTP is 5-propynyl-dCTP. In some cases, the extension reaction extends the 3' ends of short strand of the adapters ligated to the ends of the double stranded polynucleotide fragments, thereby generating polynucleotide fragments comprising complementary adapter sequences at the 3' and 5' ends.

In some cases, double stranded polynucleotide fragments comprising adapter sequence at the 3' and 5' ends are captured prior to treatment with a converting agent. In some cases, the double stranded polynucleotide fragments are captured using a binding agent directed against modified dNTPs in the double-stranded polynucleotide fragments with adapters. The modified dNTP can be a modified dCTP comprising a cytosine analog. The cytosine analog can be 5-methylcytosine, 5-hydroxymethylcytosine or 5-propynylcytosine. The binding agent can be an antibody, or the binding domain of a protein directed against a cytosine analog. In some cases, the binding domain is directed against 5-methylcytosine residues. The binding domain can be from a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2. In some cases, one or both strands of the adapter sequence on the end(s) of the double stranded polynucleotide fragments comprise a cytosine analog other than 5-methylcytosine, wherein the double stranded polynucleotide fragments are captured using the binding domain of a methyl-CpG-binding domain (i.e. MBD2 or MECP2). The cytosine analog other than 5-methylcytosine can be 5-hydroxymethylcytosine or 5-propynylcytosine.

In some cases, the method further comprises a denaturing step, wherein the polynucleotide fragments comprising adapter sequences at the 3' and 5' ends are denatured. Denaturation can be achieved using any of the methods known in the art which can include, but not limited to, heat denaturation, and/or chemical denaturation. Heat denaturation can be performed by raising the temperature of the reaction mixture to be above the melting temperature of the polynucleotide fragments comprising adapter sequence at both ends. The melting temperature can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, 85, 86, 87, 88, 89, 90, 91, 92, 93, 94, or 95 degrees C. The temperature can be raised above the melting temperature by about, more than, less than, or at least 1, 2, 3, 4, 5, 6, 7, 8, 9, or 10 degrees C. Chemical denaturation can be performed using bases (i.e. NaOH), and/or competitive denaturants (i.e. urea, or formaldehyde). In some cases, denaturation generates single stranded polynucleotides fragments comprising complementary adapter sequence at the 3' and 5' ends. In some cases, denaturation generates single stranded polynucleotides fragments comprising distinct adapter sequence at the 3' and 5' ends.

In some cases, single stranded polynucleotide fragments comprising adapter sequence at the 3' and 5' ends are captured prior to treatment with a converting agent. In some cases, the polynucleotide fragments are captured by a binding agent directed against one or more modified dNTPs present in the adapter sequence. In some cases, the modified dNTP is a nucleotide base analog. In some cases, the binding agent is a binding protein. In some cases, the binding protein is an antibody directed against the modified dNTP. In some cases, the binding protein is an antibody directed against the modified dNTP, wherein the modified dNTP is a nucleotide analog. In some cases, the single stranded polynucleotide fragments comprising adapter sequence at the 3' and 5' ends are captured prior to treatment with a bisulfite. In some cases, the nucleic acid fragments (polynucleotides) are captured by a binding agent directed against one or more elements present in the adapter sequence. In some cases, the one or more elements comprise a cytosine analog. In some cases, the cytosine analog is 5-methylcytosine. In some cases, the binding agent is a 5-methylcytosine binding protein. In some cases, the binding protein is an anti-5-methylcytosine antibody. In some cases, 5-methylcytosine capture is performed prior to bisulfite treatment, wherein the cytosine analog resistant to bisulfite treatment is a cytosine analog other than 5-methylcytosine. In some cases, the cytosine analog can be 5-hydroxymethylcytosine or 5-propynylcytosine. The one or more elements can be introduced during the extension reaction. In some cases a modified nucleotide can be incorporated during the extension reaction, wherein the modified nucleotide contains a tag. The tag can be a biotin moiety. In some cases, the binding agent is avidin, streptavidin, or an anti-biotin antibody.

Following denaturation and optional capture by a binding agent, the single-stranded polynucleotide fragments comprising adapter sequence at the 3' and 5' ends can be treated with a converting agent. In some cases, treatment of the single-stranded polynucleotide fragments with a converting agent alters the sequence of the complement of the ligation strand as well as the first and second strands of the double stranded polynucleotide fragment, while leaving the sequence of the ligation or first strand unchanged. In some cases, a single adapter is ligated to the 5' ends of the polynucleotide fragments, whereby treatment with a converting agent generates single stranded polynucleotide fragments comprising non-complementary sequence at the 5' and 3' ends. In some cases, distinct adapters are ligated to the 5' ends of the polynucleotide fragments, whereby treatment with a converting agent generates single stranded polynucleotide fragments wherein the non-ligation strands of the distinct adapters is altered to be non-complementary to the ligation strands of the distinct adapters. In some embodiments, the sequence of the ligation or first strand of the adapter marks the 5' end of the polynucleotide fragments, thereby maintaining the strandedness of the polynucleotide fragment and thus providing information on directionality.

In some cases, the single-stranded nucleic acid fragments are treated with a converting agent wherein the converting agent is bisulfite. In some cases, treatment of the single-stranded polynucleotide fragments converts cytosine residues in the polynucleotide fragment and the complement of the ligation or first strand to uracil residues while the cytosine analogs in the ligation or first strand are resistant to conversion. In some cases, treatment of the single stranded polynucleotide fragments with bisulfite generates single stranded polynucleotide fragments comprising non-complementary adapter sequence at the 5' and 3' ends. In some cases, the sequence of the ligation strand of the adapter unaltered by bisulfite treatment marks the 5' end of the polynucleotide fragments, thereby maintaining the strandedness of the polynucleotide fragment and thus providing information on directionality. In some cases, distinct adapters are ligated to the 5' ends of the polynucleotide fragments, whereby treatment with a bisulfite generates single stranded polynucleotide fragments wherein cytosine residues in the non-ligation strands of the distinct adapters are converted to uracil residues, whereby the sequence of the non-ligation strand is no longer complementary to the ligation strands of the distinct adapters.

In some cases, the method further comprises amplifying the single-stranded polynucleotide fragments comprising adapter sequences at the 3' and 5' ends. In some cases, amplification of the single-stranded polynucleotide fragments comprising adapter sequence at the 3' and 5' ends generates directional polynucleotide libraries. In some cases, one end of the polynucleotide fragment marks the orientation of the original polynucleotide strand to which it is appended due to its resistance to conversion by the converting agent, whereby the sequence in said end is resistant to conversion to a different sequence by treatment with the converting agent. In some cases, amplification of the single-stranded polynucleotide fragments comprising adapter sequence at the 3' and 5' ends generates directional polynucleotide libraries wherein one end of the polynucleotide fragments marks the orientation of the original polynucleotide strand to which it is appended due to its resistance to conversion by bisulfite treatment. In some cases, the cytosine residues present in said end are resistant to conversion to uracil residues by bisulfite treatment In some cases, amplifying the single stranded polynucleotide fragments comprising adapter sequence at the 3' and 5' ends comprises the use of a first primer and a second primer. In some cases, the first primer is directed against sequence complementary to the ligation or first strand of an adapter altered following treatment with a converting agent. In some cases, the second primer is directed against sequence complementary to the ligation or first strand of an adapter, wherein the ligation or first strand to which said complementary sequence is complementary is not altered by treatment with the converting agent. In some cases, the converting agent is bisulfite, whereby treatment with bisulfite converts cytosine residues in the sequence complementary to the ligation or first strand to uracil residues. In some cases, the first primer is directed against sequence complementary to the ligation or first strand of the adapter comprising uracil residues following bisulfite treatment. In some cases, the second primer is directed against sequence complementary to the ligation or first strand of the adapter, wherein the ligation or first strand to which said complementary sequence is complementary to does not contain uracil residues following bisulfite treatment. The single stranded polynucleotide fragments comprising adapter sequence at the 3' and 5' ends can represent a first strand of a double stranded polynucleotide fragment or a second strand of a double stranded polynucleotide fragment. In some cases, a single adapter is ligated to the 5' ends of the polynucleotide, whereby the first and second strands can comprise non-complementary sequence following treatment with the converting agent (i.e. bisulfite treatment). In some cases, distinct adapters are ligated to the 5' ends of the polynucleotide fragments, whereby treatment with bisulfite generates single stranded polynucleotide fragments from a first strand of a double stranded polynucleotide fragment or a second strand of a double stranded polynucleotide fragment, wherein cytosine residues in the non-ligation strands of the distinct adapters are converted to uracil residues. In these cases, the sequence of the non-ligation strand is no longer complementary to the ligation strands of the distinct adapters. Amplifying the single stranded polynucleotide fragments comprising adapter sequence at the 3' and 5' ends can produce amplification products from either or both of the first and second strand of the double stranded polynucleotide fragment following treatment with the converting agent (i.e. bisulfite). In some cases, the first and/or second primer further comprises one or more identifier sequences. In some cases, the identifier sequences comprise a non-hybridizable tail on the first and/or second primer. The identifier sequence can be a barcode sequence, a flow cell sequence, and/or an index sequence. In some cases, the index sequence is a Truseq primer sequence compatible with the next generation sequencing platform produced by Illumina. In some cases, the first and/or second primer can bind to a solid surface. The solid surface can be a planar surface or a bead. The planar surface can be the surface of a chip, microarray, well, or flow cell. In some cases, the first and/or second primer comprises one or more sequence elements products of the amplification reaction (i.e. amplification products) to a solid surface, wherein the one or more sequences are complementary to one or more capture probes attached to a solid surface.

In some cases, methods for generating a polynucleotide library using modified duplex-forming adapters described herein further comprise determining the methylation status of the input double stranded polynucleotide. In some cases, the input polynucleotide is genomic DNA and the amplification of single-stranded polynucleotide fragments comprising non-complementary sequence at the 3' and 5' ends is followed by sequencing. Further to this embodiment, the methylation status of the genomic DNA can be determined by comparing the sequence obtained from the sequencing of the single-stranded polynucleotide fragments comprising non-complementary sequence at the 3' and 5' ends representing either or both of the first and second strand of the double stranded polynucleotide following treatment with converting agent (i.e. bisulfite treatment) generated by the methods described herein against a reference sequence. The reference sequence can be the sequence of the genomic DNA (either or both strands) not subjected to alteration by treatment with the converting agent. The comparing can be performed on a computer. The comparing can be done on a computer using a sequence alignment tool or program. The sequence alignment tool or program can map bisulfite treated sequencing reads to a genome of interest and perform methylation calls. The bisulfite sequencing mapping tool can be the Bismark program. In some cases, the comparing comprises performing a nucleotide alignment between the sequence obtained from the sequencing of the single-stranded DNA fragments comprising non-complementary sequence at the 3' and 5' ends generated by the methods described herein with a reference sequence on a computer using any of the nucleotide alignment programs known in the art (e.g. Bismark). In some cases, the methods described herein can be used to determine the methylation status of a specific locus or region of genomic DNA or the entire genome (i.e. the methylome). In some cases, following bisulfite treatment, the methylation status of a given cytosine residue is inferred by comparing the sequence to an unmodified reference sequence.

Sequencing can be any of the next generation sequencing (NGS) methods described herein. In some cases, the NGS method comprises sequencing by synthesis. In some embodiments, sequencing is performed with primers directed against known or universal sequence introduced into the nucleic acid fragments by the adapter ligated to the nucleic acid fragments. In some cases, the primers used for sequencing are directed against adapter sequence unaltered by treatment with a converting agent. In some cases, primers used for sequencing are directed against adapter sequence altered by treatment with a converting agent. The converting agent can be bisulfite, wherein bisulfite treatment converts cytosine residues to uracil residues. In some cases, the sequencing primers are directed against adapter sequence comprising thymine residues following bisulfite treatment and amplification. In some cases, the sequencing primers are directed against adapter sequence wherein the adapter sequence is resistant to conversion by bisulfite treatment. In this embodiment, the adapter sequence to which the sequencing primers are directed does not comprise thymine residues following bisulfite treatment and amplification. In some cases, sequencing is performed with primers directed against identifier sequence introduced into the polynucleotide fragments by the first and/or second primer used to amplify single-stranded polynucleotide fragments comprising non-complementary sequence at the 3' and 5' ends. The identifier sequence can be a barcode sequence, a flow cell sequence, and/or index sequence. In some cases, the index sequence is a Truseq primer sequence compatible with the next generation sequencing platform produced by Illumina.

A schematic exemplary of an embodiment of the methods described herein for generating a directional, bisulfite converted library using unmodified partial duplex-forming adapters is shown in FIG. 2. As illustrated in FIG. 2, adapters are ligated to each 5' end of each strand of a double stranded polynucleotide fragment. The double stranded polynucleotide fragment comprises 5' phosphates, whereas the adapters do not comprise 5' phosphates. The adapter is a partial duplex adapter, wherein the partial duplex comprises a long arm comprising forward adapter sequence hybridized to a short arm, wherein the short arm of the adapter hybridizes to the 3' end of the long arm of the adapter. None of the cytosine residues in the partial duplex adapter comprise 5-methylcytosine residues, and both the 5' and 3' ends of the short arm are blocked such that neither end is enzymatically reactive. Thus, the long arm of the adapter serves as the ligation strand, while the short arm of the adapter serves as the non-ligation strand. Following ligation, only the long arm of the adapter is joined to the 5'ends of the double stranded polynucleotide fragment, thereby creating a nick or break in the polynucleotide backbone between the 3' ends of each of the strands of the double stranded DNA fragments and the short arm of the adapters. The nick is filled in using a DNA polymerase, wherein the 3' ends of the double stranded DNA fragment are extended using the long arm of the adapter as template, and the short arm of the adapter is displaced. As depicted in FIG. 2, extension of the 3' ends of the double stranded DNA fragments occurs in the presence of dATP, dGTP, dTTP, and 5-methyl dCTP. Thus, extension of the 3'ends of the double-stranded DNA fragments generates double stranded DNA fragments comprising the ligation strand of the adapter on the 5' ends and the complement of the ligation strand comprising 5-methylcytosines at the 3' ends. Following extension, the double-stranded DNA fragments are denatured, thereby generating single stranded DNA fragments comprising the ligation strand at the 5' end and the complement of the ligation strand comprising 5-methylcytosine at the 3' end, wherein the ligation strand does not comprise 5-methylcytosines. The single-stranded DNA fragments are then subjected to bisulfite treatment by any of the methods known in the art, wherein 5-methylcytosine residues are left intact, while cytosine residues are converted to the base uracil. Thus, bisulfite treatment in FIG. 2 generates single stranded DNA fragments comprising non-complementary end sequences, wherein the 5' end comprises the ligation strand comprising the base uracil wherever bisulfite treatment has converted a cytosine residue, while the 3' end comprises the complement of the ligation strand comprising non-converted 5-methylcytosine residues. The single-stranded DNA fragments further comprise the DNA fragment between the non-complementary ends, wherein cytosine residues within the DNA fragment have been converted to uracil residues following bisulfite treatment. The single stranded DNA fragments are then amplified (i.e. via PCR) using the primer pair (P1/P2) shown in FIG. 2. As shown in FIG. 2, the P2 primer comprises at least of portion of the sequence of the ligation strand, wherein the sequence compensates for the conversion of cytosine to uracil following bisulfite treatment in said sequence. As shown in FIG. 2, the P2 primer further comprises a non-hybridizable tail, wherein the tail comprises a reverse flow cell sequence, a TruSeq primer sequence or a second read barcode sequence, and optional barcode sequence. The additional barcode sequence can be added for embodiments whereby barcoded libraries are generated. The P1 primer comprises a non-hybridizable tail portion comprising a forward flow cell sequence and a hybridizable portion comprising at least a portion of the ligation strand sequence, wherein the cytosines have not been converted to uracil. Following amplification with the P1/P2 primers, double stranded DNA complexes appended with non-complementary ends derived from the ligated adapter and flow cell sequences as depicted in FIG. 2 are generated. The double-stranded DNA complexes are compatible with the next generation sequencing platform developed by Illumina via the flow cell and Truseq primer sequences introduced during amplification and can be sequenced using sequencing primers directed against sequence present in the appended adapters. Sequencing is performed using a standard read primer directed against at least a portion of the forward adapter sequence and a custom second read sequencing primer directed against the bisulfite converted adapter sequence.

VI. Oligonucleotides

The term "oligonucleotide" can refer to a polynucleotide chain, typically less than 200 residues long, e.g., between 15 and 100 nucleotides long, but also intended to encompass longer polynucleotide chains. Oligonucleotides can be single- or double-stranded. The terms "primer" and "oligonucleotide primer" can refer to an oligonucleotide capable of hybridizing to a complementary nucleotide sequence. The term "oligonucleotide" can be used interchangeably with the terms "primer," "adapter," and "probe."

The term "hybridization"/"hybridizing" and "annealing" can be used interchangeably and can refer to the pairing of complementary nucleic acids.

The term "primer" can refer to an oligonucleotide, generally with a free 3' hydroxyl group, that is capable of hybridizing with a template (such as a target polynucleotide, target DNA, target RNA or a primer extension product) and is also capable of promoting polymerization of a polynucleotide complementary to the template. A primer can contain a non-hybridizing sequence that constitutes a tail of the primer. A primer can still be hybridizing to a target even though its sequences may not fully complementary to the target.

Primers can be oligonucleotides that can be employed in an extension reaction by a polymerase along a polynucleotide template, such as in PCR or cDNA synthesis, for example. The oligonucleotide primer can be a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, 90%, 95%, or 100%, complementarity to a sequence or primer binding site.

Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to the genetic targets described herein. In some cases, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some cases, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 50 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer can be calculated using software programs such as Net Primer (free web based program at http://www.premierbiosoft.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the TM can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

"Complementary" can refer to complementarity to all or only to a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. A target polynucleotide can be larger than an oligonucleotide primer or primers as described previously.

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer can be a random sequence. Oligonucleotide primers comprising random sequences can be referred to as "random primers", as described below. In yet other cases, an oligonucleotide primer such as a first primer or a second primer comprises a set of primers such as for example a set of first primers or a set of second primers. In some cases, the set of first or second primers can comprise a mixture of primers designed to hybridize to a plurality (e.g. about, more than, less than, or at least 2, 3, 4, 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, or 25,000) target sequences. In some cases, the plurality of target sequences can comprise a group of related sequences, random sequences, a whole transcriptome or fraction (e.g. substantial fraction) thereof, or any group of sequences such as mRNA.

The term "adapter" can refer to an oligonucleotide of known sequence, the ligation of which to a target polynucleotide or a target polynucleotide strand of interest enables the generation of amplification-ready products of the target polynucleotide or the target polynucleotide strand of interest. Various adapter designs can be used. Suitable adapter molecules include single or double stranded nucleic acid (DNA or RNA) molecules or derivatives thereof, stem-loop nucleic acid molecules, double stranded molecules comprising one or more single stranded overhangs of 1, 2, 3, 4, 5, 6, 7, 8, 9, 10 bases or longer, proteins, peptides, aptamers, organic molecules, small organic molecules, or any adapter molecules known in the art that can be covalently or non-covalently attached, such as for example by ligation, to the double stranded nucleic acid fragments. The adapters can be designed to comprise a double-stranded portion which can be ligated to double-stranded nucleic acid (or double-stranded nucleic acid with overhang) products.

Adapter oligonucleotides can have any suitable length, at least sufficient to accommodate the one or more sequence elements of which they are comprised. In some cases, adapters are about, less than about, or more than about 10, 15, 20, 25, 30, 35, 40, 45, 50, 55, 60, 65, 70, 75, 80, 90, 100, 200, or more nucleotides in length. In some cases, the adapter is stem-loop or hairpin adapter, wherein the stem of the hairpin adapter is about, less than about, or more than about 1, 2, 3, 4, 5, 6, 7, 8, 9, 10, 11, 12, 13, 14, 15, 20, 25, 30, 35, 40, 45, 50, 75, 100, or more nucleotides in length. Stems can be designed using a variety of different sequences that result in hybridization between the complementary regions on a hairpin adapter, resulting in a local region of double-stranded DNA. For example, stem sequences can be utilized that are from 15 to 18 nucleotides in length with equal representation of G:C and A:T base pairs. Such stem sequences are predicted to form stable dsDNA structures below their predicted melting temperatures of .about.45 degree C. Sequences participating in the stem of the hairpin can be perfectly complementary, such that each base of one region in the stem hybridizes via hydrogen bonding with each base in the other region in the stem according to Watson-Crick base-pairing rules. Alternatively, sequences in the stem can deviate from perfect complementarity. For example, there can be mismatches and or bulges within the stem structure created by opposing bases that do not follow Watson-Crick base pairing rules, and/or one or more nucleotides in one region of the stem that do not have the one or more corresponding base positions in the other region participating in the stem. Mismatched sequences can be cleaved using enzymes that recognize mismatches. The stem of a hairpin can comprise DNA, RNA, or both DNA and RNA. In some cases, the stem and/or loop of a hairpin, or one or both of the hybridizable sequences forming the stem of a hairpin, comprise nucleotides, bonds, or sequences that are substrates for cleavage, such as by an enzyme, including but not limited to endonucleases and glycosylases. The composition of a stem can be such that only one of the hybridizable sequences forming the stem is cleaved. For example, one of the sequences forming the stem can comprise RNA while the other sequence forming the stem consists of DNA, such that cleavage by an enzyme that cleaves RNA in an RNA-DNA duplex, such as RNase H, cleaves only the sequence comprising RNA. One or both strands of a stem and/or loop of a hairpin can comprise about, more than, less than, or at least 1, 2, 3, 4, 5, 6, 7, 8, 9, 10, 11, 12, 13, 14, 15, 16, 17, 18, 19, or 20 non-canonical nucleotides (e.g. uracil), and/or methylated nucleotides. In some cases, the loop sequence of a hairpin adapter is about, less than about, or more than about 5, 10, 15, 20, 25, 30, 35, 40, 45, 50, or more nucleotides in length.

An adapter can comprise at least two nucleotides covalently linked together. An adapter as used herein can contain phosphodiester bonds, although in some cases, as outlined below, nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-0 atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. Adapters can be single stranded or double stranded, as specified, or contain portions of both double stranded or single stranded sequence. Depending on the application, adapters can be DNA, RNA, or a hybrid, where the adapter contains any combination of deoxyribo- and ribo-nucleotides, and any combination of bases, including uracil, adenine, thymine, cytosine, guanine, inosine, xathanine hypoxathanine, isocytosine, isoguanine, etc.

Various ligation processes and reagents are known in the art and can be useful for carrying out the methods provided herein. For example, blunt ligation can be employed. Similarly, a single dA nucleotide can be added to the 3'-end of the double-stranded DNA product, by a polymerase lacking 3'-exonuclease activity and can anneal to an adapter comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g, from New England Biolabs, Roche).

VII. RNA-Dependent DNA Polymerases

RNA-dependent DNA polymerases for use in the methods and compositions provided herein can be capable of effecting extension of a primer according to the methods provided herein. Accordingly, an RNA-dependent DNA polymerase can be one that is capable of extending a nucleic acid primer along a nucleic acid template that is comprised at least predominantly of ribonucleotides. Suitable RNA-dependent DNA polymerases for use in the methods, compositions, and kits provided herein include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from *E. coli*, can be employed for the degradation of the starting RNA sample and the formation of the double stranded cDNA. Combinations of RTs can also contemplated, including combinations of different non-mutant RTs, combinations of different mutant RTs, and combinations of one or more non-mutant RT with one or more mutant RT.

VIII. DNA-Dependent DNA Polymerases

DNA-dependent DNA polymerases for use in the methods and compositions provided herein can be capable of effecting extension of a primer according to the methods provided herein. Accordingly, a DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods provided herein include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and *E. coli* DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension can be performed using a polymerase comprising strong strand displacement activity such as for example Bst polymerase. In other cases, the primer extension can be performed using a polymerase comprising weak or no strand displacement activity. One skilled in the art can recognize the advantages and disadvantages of the use of strand displacement activity during the primer extension step, and which polymerases can be expected to provide strand displacement activity (see e.g., New England Biolabs Polymerases). For example, strand displacement activity can be useful in ensuring whole transcriptome coverage during the random priming and extension step. Strand displacement activity can further be useful in the generation of double stranded amplification products during the priming and extension step. Alternatively, a polymerase which comprises weak or no strand displacement activity can be useful in the generation of single stranded nucleic acid products during primer hybridization and extension that can be hybridized to the template nucleic acid.

In some cases, the double stranded products generated by the methods described herein can be end repaired to produce blunt ends for the adapter ligation applications described herein. Generation of the blunt ends on the double stranded products can be generated by the use of a single strand specific DNA exonuclease such as for example exonuclease 1, exonuclease 7 or a combination thereof to degrade overhanging single stranded ends of the double stranded products. Alternatively, the double stranded products can be blunt ended by the use of a single stranded specific DNA endonuclease for example but not limited to mung bean endonuclease or S1 endonuclease. Alternatively, the double stranded products can be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded products of the primer extension reaction. In still other cases, the products of the extension reaction can be made blunt ended by filling in the overhanging single stranded ends of the double stranded products. For example, the fragments can be incubated with a polymerase such as T4 DNA polymerase or Klenow polymerase or a combination thereof in the presence of one or more dNTPs to fill in the single stranded portions of the double stranded products. Alternatively, the double stranded products can be made blunt by a combination of a single stranded overhang degradation reaction using exonucleases and/or polymerases, and a fill-in reaction using one or more polymerases in the presence of one or more dNTPs.

In another embodiment, the adapter ligation applications described herein can leave a gap between a non-ligation strand of the adapters and a strand of the double stranded product. In these instances, a gap repair or fill-in reaction can be used to append the double stranded product with the sequence complementary to the ligation strand of the adapter. Gap repair can be performed with any number of DNA dependent DNA polymerase described herein. In some cases, gap repair can be performed with a DNA dependent DNA polymerase with strand displacement activity. In some cases, gap repair can be performed using a DNA dependent DNA polymerase with weak or no strand displacement activity. In some cases, the ligation strand of the adapter can serve as the template for the gap repair or fill-in reaction. In some cases, gap repair can be performed using Taq DNA polymerase.

IX. Methods of Amplification

The methods, compositions and kits described herein can be useful to generate amplification-ready products for downstream applications such as massively parallel sequencing (i.e. next generation sequencing methods) or hybridization platforms. Methods of amplification are well known in the art. Examples of PCR techniques that can be used include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR(PCR-RFLP), PCR-RFLP/RT-PCR-RFLP, hot start PCR, nested PCR, in situ polony PCR, in situ rolling circle amplification (RCA), bridge PCR, picotiter PCR, digital PCR, droplet digital PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA), single primer isothermal amplification (SPIA, see e.g. U.S. Pat. No. 6,251,639), Ribo-SPIA, or a combination thereof. Other amplification methods that can be used herein include those described in U.S. Pat. Nos. 5,242,794; 5,494,810; 4,988,617; and 6,582, 938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference. In some cases, the amplification methods can be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the genomic DNA, rather than the genomic DNA itself. In some cases, at least 200, 175, 150, 125, 100, 90, 80, 70, 60, 50, 40, 30, 20, 10, or 0 droplets have zero copies of a target nucleic acid.

PCR can involve in vitro amplification based on repeated cycles of denaturation, oligonucleotide primer annealing, and primer extension by thermophilic template dependent polynucleotide polymerase, which can result in the exponential increase in copies of the desired sequence of the polynucleotide analyte flanked by the primers. In some cases, two different PCR primers, which anneal to opposite strands of the DNA, can be positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes can hybridize with each complementary strand of the nucleic acid analyte, if present, and ligase can be employed to bind each pair of probes together resulting in two templates that can serve in the next cycle to reiterate the particular nucleic acid sequence.

SDA (Westin et al 2000, Nature Biotechnology, 18, 199-202; Walker et al 1992, Nucleic Acids Research, 20, 7, 1691-1696), can involve isothermal amplification based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Some aspects of the methods described herein can utilize linear amplification of nucleic acids or polynucleotides. Linear amplification can refer to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some cases, the amplification is exponential, e.g. in the enzymatic amplification of specific double stranded sequences of DNA by a polymerase chain reaction (PCR). In other embodiments the amplification method is linear. In other embodiments the amplification method is isothermal.

X. Applications

One aspect of the methods and compositions disclosed herein is that they can be efficiently and cost-effectively utilized for downstream analyses, such as next generation sequencing or hybridization platforms, with minimal loss of biological material of interest. The methods described herein can be particularly useful for generating high throughput sequencing libraries from bisulfite-converted DNA, for methylation analysis across an entire genome, or methylome.

For example, the methods described herein can be useful for sequencing by the method commercialized by Illumina, as described U.S. Pat. Nos. 5,750,341; 6,306,597; and 5,969,119. Directional (strand-specific) nucleic acid libraries can be prepared using the methods described herein, and the selected single-stranded nucleic acid is amplified, for example, by PCR. The resulting nucleic acid is then denatured and the single-stranded amplified polynucleotides can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell is imaged. The identity of the first base for each cluster is then recorded. Cycles of sequencing can be performed to determine the fragment sequence one base at a time.

In some cases, the methods described herein can be useful for preparing target polynucleotides for sequencing by the sequencing by ligation methods commercialized by Applied Biosystems (e.g., SOLiD sequencing). Directional (strand-specific) nucleic acid libraries can be prepared using the methods described herein, and the selected single-stranded nucleic acid can then be incorporated into a water in oil emulsion along with polystyrene beads and amplified by for example PCR. In some cases, alternative amplification methods can be employed in the water-in-oil emulsion such as any of the methods provided herein. The amplified product in each water microdroplet formed by the emulsion interact, bind, or hybridize with the one or more beads present in that microdroplet leading to beads with a plurality of amplified products of substantially one sequence. When the emulsion is broken, the beads float to the top of the sample and are placed onto an array. The methods can include a step of rendering the nucleic acid bound to the beads stranded or partially single stranded. Sequencing primers are then added along with a mixture of four different fluorescently labeled oligonucleotide probes. The probes bind specifically to the two bases in the polynucleotide to be sequenced immediately adjacent and 3' of the sequencing primer to determine which of the four bases are at those positions. After washing and reading the fluorescence signal form the first incorporated probe, a ligase is added. The ligase cleaves the oligonucleotide probe between the fifth and sixth bases, removing the fluorescent dye from the polynucleotide to be sequenced. The whole process is repeated using a different sequence primer, until all of the intervening positions in the sequence are imaged. The process allows the simultaneous reading of millions of DNA fragments in a 'massively parallel' manner. This 'sequence-by-ligation' technique uses probes that encode for two bases rather than just one allowing error recognition by signal mismatching, leading to increased base determination accuracy.

In other embodiments, the methods are useful for preparing target polynucleotides for sequencing by synthesis using the methods commercialized by 454/Roche Life Sciences, including but not limited to the methods and apparatus described in Margulies et al., Nature (2005) 437:376-380 (2005); and U.S. Pat. Nos. 7,244,559; 7,335,762; 7,211,390; 7,244,567; 7,264,929; and 7,323,305. Directional (strand-specific) nucleic acid libraries can be prepared using the methods described herein, and the selected single-stranded nucleic acid is amplified, for example, by PCR. The amplified products can then be immobilized onto beads, and compartmentalized in a water-in-oil emulsion suitable for amplification by PCR. In some cases, alternative amplification methods other than PCR can be employed in the water-in-oil emulsion such as any of the methods provided herein. When the emulsion is broken, amplified fragments remain bound to the beads. The methods can include a step of rendering the nucleic acid bound to the beads single stranded or partially single stranded. The beads can be enriched and loaded into wells of a fiber optic slide so that there is approximately 1 bead in each well. Nucleotides are flowed across and into the wells in a fixed order in the presence of polymerase, sulfhydrolase, and luciferase. Addition of nucleotides complementary to the target strand results in a chemiluminescent signal that is recorded such as by a camera. The combination of signal intensity and positional information generated across the plate allows software to determine the DNA sequence.

In other embodiments, the methods are useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276, 720; and in U.S. Patent Application Publication Nos. US20090061439; US20080087826; US20060286566; US20060024711; US20060024678; US20080213770; and US20080103058. Directional (strand-specific) nucleic acid libraries can be prepared using the methods described herein, and the selected single-stranded nucleic acid is amplified, for example, by PCR. The amplified products can then be immobilized onto a flow-cell surface. The methods can include a step of rendering the nucleic acid bound to the flow-cell surface stranded or partially single stranded. Polymerase and labeled nucleotides are then flowed over the immobilized DNA. After fluorescently labeled nucleotides are incorporated into the DNA strands by a DNA polymerase, the surface is illuminated with a laser, and an image is captured and processed to record single molecule incorporation events to produce sequence data.

In some cases, the methods described herein can be useful for sequencing by the method commercialized by Pacific Biosciences as described in U.S. Pat. Nos. 7,462,452; 7,476, 504; 7,405,281; 7,170,050; 7,462,468; 7,476,503; 7,315, 019; 7,302,146; 7,313,308; and U.S. Patent Application Publication Nos. US20090029385; US20090068655; US20090024331; and US20080206764. Directional (strand-specific) nucleic acid libraries can be prepared using the methods described herein, and the selected single-stranded nucleic acid is amplified, for example, by PCR. The nucleic acid can then be immobilized in zero mode waveguide arrays. The methods can include a step of rendering the nucleic acid bound to the waveguide arrays single stranded or partially single stranded. Polymerase and labeled nucleotides are added in a reaction mixture, and nucleotide incorporations are visualized via fluorescent labels attached to the terminal phosphate groups of the nucleotides. The fluorescent labels are clipped off as part of the nucleotide incorporation. In some cases, circular templates are utilized to enable multiple reads on a single molecule.

Another example of a sequencing technique that can be used in the methods described herein is nanopore sequencing (see e.g. Soni G V and Meller A. (2007) Clin Chem 53:

1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods described herein is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Another example of a sequencing technique that can be used in the methods described herein is DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adapters (Ad1) can be attached to the ends of the fragments. The adapters can be used to hybridize to anchors for sequencing reactions. DNA with adapters bound to each end can be PCR amplified. The adapter sequences can be modified so that complementary single strand ends bind to each other forming circular DNA. The DNA can be methylated to protect it from cleavage by a type IIS restriction enzyme used in a subsequent step. An adapter (e.g., the right adapter) can have a restriction recognition site, and the restriction recognition site can remain non-methylated. The non-methylated restriction recognition site in the adapter can be recognized by a restriction enzyme (e.g., AcuI), and the DNA can be cleaved by AcuI 13 bp to the right of the right adapter to form linear double stranded DNA. A second round of right and left adapters (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adapter (Ad3) can be ligated to the right and left flank of the linear DNA, and the resulting fragment can be PCR amplified. The adapters can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adapters (Ad4) can be ligated to the DNA, the DNA can be amplified (e.g., by PCR), and modified so that they bind each other and form the completed circular DNA template. Rolling circle replication (e.g., using Phi 29 DNA polymerase) can be used to amplify small fragments of DNA. The four adapter sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adapter sequences can be determined.

In some cases, the sequencing technique can comprise paired-end sequencing in which both the forward and reverse template strand can be sequenced. In some cases, the sequencing technique can comprise mate pair library sequencing. In mate pair library sequencing, DNA can be fragments, and 2-5 kb fragments can be end-repaired (e.g., with biotin labeled dNTPs). The DNA fragments can be circularized, and non-circularized DNA can be removed by digestion. Circular DNA can be fragmented and purified (e.g., using the biotin labels). Purified fragments can be end-repaired and ligated to sequencing adapters.

In some cases, a sequence read is about, more than about, less than about, or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or 3000 bases. In some cases, a sequence read is about 10 to about 50 bases, about 10 to about 100 bases, about 10 to about 200 bases, about 10 to about 300 bases, about 10 to about 400 bases, about 10 to about 500 bases, about 10 to about 600 bases, about 10 to about 700 bases, about 10 to about 800 bases, about 10 to about 900 bases, about 10 to about 1000 bases, about 10 to about 1500 bases, about 10 to about 2000 bases, about 50 to about 100 bases, about 50 to about 150 bases, about 50 to about 200 bases, about 50 to about 500 bases, about 50 to about 1000 bases, about 100 to about 200 bases, about 100 to about 300 bases, about 100 to about 400 bases, about 100 to about 500 bases, about 100 to about 600 bases, about 100 to about 700 bases, about 100 to about 800 bases, about 100 to about 900 bases, or about 100 to about 1000 bases.

The number of sequence reads from a sample can be about, more than about, less than about, or at least about 100, 1000, 5,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000.

The depth of sequencing of a sample can be about, more than about, less than about, or at least about 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, 110×, 120×, 130×, 140×, 150×, 160×, 170×, 180×, 190×, 200×, 300×, 400×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, or 10,000×. The depth of sequencing of a sample can about 1× to about 5×, about 1× to about 10×, about 1× to about 20×, about 5× to about 10×, about 5× to about 20×, about 5× to about 30×, about 10× to about 20×, about 10× to about 25×, about 10× to about 30×, about 10× to about 40×, about 30× to about 100×, about 100× to about 200×, about 100× to about 500×, about 500× to about 1000×, about 1000×, to about 2000×, about 1000× to about 5000×, or about 5000× to about 10,000×. Depth of sequencing can be the number of times a sequence (e.g., a genome) is sequenced. In some cases, the Lander/Waterman equation is used for computing coverage. The general equation can be: C=LN/G, where C=coverage; G=haploid genome length; L=read length; and N=number of reads.

In some cases, different barcodes can be added to polynucleotides in different samples (e.g., by using primers and/or adapters), and the different samples can be pooled and analyzed in a multiplexed assay. The barcode can allow the determination of the sample from which a polynucleotide originated.

The compositions, kits, and methods provided herein can be used to treat, prevent, diagnose, and/or prognose a variety of methylation related diseases. Such methylation related diseases can be cancer, mental retardation, neurodegenerative disorders, imprinting disorders, and syndromes involving chromosomal abnormalities. Such methylation related diseases can be Immunodeficiency-centromeric instability-facial anomalies syndrome (ICF), Rett syndrome, Beckwith-Wiedemann Syndrome (BWS), ATRX-linked mental retardation, fragile X syndrome. The cancer can be breast, ovarian, lung, head and neck, testicular, colon, or brain cancer. The cancer can be medulloblastoma, hepatoblastoma, uterine leiomyosarcomata, cervical carcinoma, renal cell carcinoma, rhadbomyosarcoma, gliomas, colorectal cancer, Wilm's tumour, Burkitt's lymphoma, or leukemia. In some cases, the methods described herein are used to determine the status of one or more genes associated with methylation related disorders. The status can include the presence or absence of a nucleic acid modification (i.e. methylation) at one or more bases in a nucleic acid sequence. In some cases, the methods disclosed herein are used to determine or recommend a course of treatment or administration of a therapy based on the status of one or more genes. The therapy can reduce one or more signs or symptoms of a methylation related disease. The therapy can prevent one or more signs or symptoms of any methylation related diseases. In some cases, the methods disclosed herein are used to determine the outcome or progress of a course of treatment or administration of a therapy based on the status of one or more genes. Genes associated with methylation related diseases can be, but are not limited to Socs1, Cdkn1c, Slc22a11, Bmp3b, Wit1, Rassf1a, Brca1, p16, Dapk, Mgmt, D4z4, Nbl2, H19, Igf2, G6pd, Rasgrf1 Sybl1, Ar, Pgk1, Dyz2, or Fmr1. In some cases, the status of 1, 2, 3, 4, 5, 6, 7, 8, 9, 10, 11, 12, 13, 14, 15, 16, 17, 18, 19, or 20 of any of the genes associated with methylation related diseases are analyzed.

The methods, kits, and compositions described herein can be used to prevent the development of one or more signs and/or symptoms of methylation related diseases or reduce the severity of one or more signs and/or symptoms of methylation related diseases. The severity of the sign and/or symptom can be reduced by about, or more than about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent. The severity of the sign or symptom can be decreased by about 1 percent to about 10 percent, about 1 percent to about 20 percent, about 1 percent to about 30 percent, about 1 percent to about 50 percent, about 1 percent to about 90 percent, about 1 percent to about 99 percent, about 10 percent to about 20 percent, about 10 percent to about 30 percent, about 10 percent to about 50 percent, about 50 percent to about 75 percent, about 75 percent to about 90 percent, about 75 percent to about 99 percent. The severity of the sign and/or symptom can be reduced by about, more than about, or at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 200-fold, 300-fold, 400-fold, 500-fold, 600-fold, 700-fold, 800-fold, 900-fold, or 1000-fold. The severity of the sign and/or symptom can be reduced by about 2-fold to 10-fold, about 2-fold to about 50-fold, about 2-fold to about 100-fold, about 10-fold to about 20-fold, about 10-fold to about 50-fold, about 10-fold to about 75-fold, about 10-fold to about 100-fold, about 50-fold to about 75-fold, about 50-fold to about 100-fold, about 100-fold to about 500-fold, about 100-fold to about 1000-fold, or about 500-fold to about 1000-fold.

The methods, kits, and compositions described herein can be used to decrease the likelihood that a subject will develop one or more signs and/or symptoms of methylation related diseases. The decrease in likelihood can be about, or more than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent. The decrease in likelihood can be about 1 percent to about 10 percent, about 1 percent to about 20 percent, about 1 percent to about 30 percent, about 1 percent to about 50 percent, about 1 percent to about 90 percent, about 1 percent to about 99 percent, about 10 percent to about 20 percent, about 10 percent to about 30 percent, about 10 percent to about 50 percent, about 50 percent to about 75 percent, about 75 percent to about 90 percent, about 75 percent to about 99 percent. The decrease in likelihood can be about, more than about, or at least about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 200-fold, 300-fold, 400-fold, 500-fold, 600-fold, 700-fold, 800-fold, 900-fold, or 1000-fold. The decrease in likelihood can be about 2-fold to 10-fold, about 2-fold to about 50-fold, about 2-fold to about 100-fold, about 10-fold to about 20-fold, about 10-fold to about 50-fold, about 10-fold to about 75-fold, about 10-fold to about 100-fold, about 50-fold to about 75-fold, about 50-fold to about 100-fold, about 100-fold to about 500-fold, about 100-fold to about 1000-fold, or about 500-fold to about 1000-fold.

A diagnosis and/or prognosis of a methylation associated neurological in a subject can be made by a health care provider, e.g., a developmental-behavioral pediatrician, a neurologist, a pediatric psychologist, or a psychiatrist. A diagnosis and/or prognosis of a neurological condition can be made or supported by a genetic test performed by a diagnostic laboratory. In some cases, a neurological assessment is administered to a subject by an individual trained and certified to administer a neurological assessment.

In some cases, a procedure can be performed to diagnose a methylation associated neurological condition in a subject, e.g., angiography, biopsy, a brain scan (e.g., computed tomography (CT), magnetic resonance imaging (MRI), positron emission tomography (PET)), cerebrospinal fluid analysis (by, e.g., lumbar puncture or spinal tap), discography, intrathecal contrast-enhanced CT scan (cisternograhpy), electronencephalography (EEG), electromyography (EMG), nerve conduction velocity (NCV) test, electronystagmography (ENG), evoked potentials (evoked response; e.g., auditory evoked potentials, visual evoked potentials, somatosensory evoked potentials), myelography, polysomnogram, single photon emission computed tomography (SPECT), thermography, or ultrasound imaging (e.g., neurosonography, transcranial Doppler ultrasound). One or more procedures that can diagnose a neurological condition can be performed on a subject.

Instruments that can be used in neurological examination can include, e.g., a tuning fork, flashlight, reflex hammer, ophthalmoscope, X-ray, fluoroscope, or a needle.

The methods, kits, and compositions provided herein can be used to treat, prevent, diagnose, and/or prognose a methylation associate disease or condition in a subject. The subject can be a male or female. The subject can have, or be suspected of having, a methylation associated disease. The subject can have a relative (e.g., a brother, sister, monozygotic twin, dizygotic twin, father, mother, cousin, aunt, uncle, grandfather, grandmother) that was diagnosed with a methylation associate disease. The subject can be, for example, a newborn (birth to about 1 month old), an infant (about 1 to 12 months old), a child (about 1 year old to 12 years old), a teenager (about 13 years old to 19 years old), an adult (about 20 years old to about 64 years old), or an elderly person (about 65 years old and older). The subject can be, for example, about 1 day to about 120 years old, about 1 day to about 110 years old, about 1 day to about 100 years old, about 1 day to about 90 years old, about 1 day to about 80 years old, about 1 day to about 70 years old, about 1 day to about 60 years old, about 1 day to about 50 years old, about 1 day to about 40 years old, about 1 day to about 30 years old, about 1 day to about 20 years old, about 1 day to about 15 years old, about 1 day to about 10 years old, about 1 day to about 9 years old, about 1 day to about 8 years old, about 1 day to about 7 years old, about 1 day to about 6 years old, about 1 day to about 5 years old, about 1 day to about 4 years old, about 1 day to about 3 years old, about 1 year to about 2 years old, about 3 years to about 15 years old, about 3 years to about 10 years old, about 3 years to about 7 years old, or about 3 years to about 5 years old. The subject can be about, more than about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old.

The methods for generating directional polynucleotide libraries as described herein can be used for detecting the presence of fetal DNA in a maternal sample. In some cases, the method comprises: (a) generating directional, bisulfite treated DNA libraries as described herein using a sample obtained from a pregnant woman comprising maternal and fetal DNA; (b) detecting the methylation status of DNA sequence of one or more genes from the sample comprising maternal and fetal DNA; and (c) comparing the methylation status the one or more genes from the sample comprising maternal and fetal DNA to a reference maternal DNA sample comprising only maternal DNA. In some cases, step (b) of the method comprises an amplification process. In some cases, the amplification process is a polymerase chain reaction (PCR), such as real-time PCR. In other embodiments, step (b) determines the quantity of the DNA sequence. In some cases, the methods provided herein can be used to determine the Rhesus D (RhD) blood group compatibility between a pregnant woman and a fetus. In some cases, the methods for generating directional polynucleotide libraries as described herein can be used for diagnosing, monitoring, or risk assessment of a number of prenatal conditions. For example, the prenatal conditions can include, but are not limited to, beta-thalassemia, cystic fibrosis, congenital adrenal hyperplasia, chromosomal aneuploidies, preeclampsia, preterm labor, and intrauterine growth retardation (IUGR). In some cases, the method comprises (a) generating directional, bisulfite treated DNA libraries as described herein using a sample obtained from a pregnant woman comprising maternal and fetal DNA; (b) detecting the amount of DNA sequence of one or more genes from the sample comprising maternal and fetal DNA; and (c) comparing the amount of the DNA sequence with a standard control, wherein an increase from the control indicates the presence of or an increased risk for developing the pregnancy-associated condition. In some cases, step (b) of the method comprises an amplification process, which can be accomplished by various means, including polymerase chain reaction (PCR), such as real-time PCR. The one or more genes can be RASSF1A, APC, CASP8, RARB, SCGB3A1, DAB2IP, PTPN6, THY1, TMEFF2, or PYCARD. The sample can be whole blood, plasma, serum, urine, or saliva. The DNA can be cell-free DNA and/or DNA derived from maternal and fetal cells present in the sample from the pregnant woman. "Standard control value" as used herein refers to a predetermined amount of a genomic sequence that is originated from a fetus and is present in an established sample. The standard control value is suitable for the use of a method described herein, in order for comparing the amount of a gene of interest (or a non-coding sequence) that is present in a test sample. The standard control can provide an average amount of a fetal gene of interest that is typical for a defined time (e.g., first trimester) during pregnancy in the blood of an average, healthy pregnant woman carrying a normal fetus, both of whom are not at risk of developing any pregnancy-associated disorders or complications. A standard control value can vary depending on the genomic sequence of interest and the nature of the sample.

The methods for generating directional polynucleotide libraries as described herein can be combined with one or more methods for measuring DNA methylation at specific genomic loci. For example, the methods for measuring DNA methylation can include, but are not limited to, immunoprecipitation of methylated DNA, methyl-binding protein enrichment of methylated fragments, and/or digestion with methylation-sensitive restriction enzymes.

The methods for generating directional polynucleotide libraries as described herein can be combined with one or more methods for profiling methylation status of the whole genome, i.e. the methylome. For example, the methods provided herein can be combined with reduced representation bisulfite sequencing (RRBS). RRBS involves digestion of a DNA sample with a methylation-insensitive restriction endonuclease that has CpG dinucleotide as a part of its recognition site, followed by bisulfite sequencing of the selected fragments (Meissner et al., *Nucleic Acids Res.* 33(18):5868-5877, 2005).

XI. Compositions and Reaction Mixtures

The present methods further provide one or more compositions or reaction mixtures. In some cases, the reaction mixture comprises: (a) a duplex adapter comprising a ligation strand of the comprising cytosine analogs resistant to bisulfite treatment and a non-ligation strand wherein the non-ligation strand is blocked at the 3' and 5' ends and is enzymatically unreactive; (b) a strand displacing polymerase; (c) unmodified dNTPs; and (d) bisulfite. In some cases, the reaction mixture further comprises (e) amplification primers directed to unique priming sites created at each end of the DNA fragments following bisulfite treatment. In some cases, at least one of the amplification primers is directed against adapter sequence following bisulfite treatment, whereby cytosine residues have been converted to uracil residues. In some cases, the reaction mixture further comprises (f) sequencing primers directed against sequences present in the adapter sequence. In some cases, at least one of the sequencing primers is directed against adapter sequence following bisulfite treatment, whereby cytosine residues have been converted to uracil residues and subsequently replaced with thymine residues following amplification. In some cases, the reaction mixture comprises: (a) a duplex adapter comprising a ligation strand and a non-ligation strand wherein the non-ligation strand is blocked at the 3' and 5' ends and is enzymatically unreactive; (b) a strand displacing polymerase; (c) modified dCTP (i.e. 5-methyl-dCTP, 5-hydroxymethyl-dCTP, or 5-propynyl-dCTP); (d) dATP, dGTP, and dTTP; and (e) bisulfite. In some cases, the reaction mixture further comprises (f) amplification primers directed to unique priming sites created at each end of the DNA fragments following bisulfite treatment. In some cases, at least one of the amplification primers is directed against adapter sequence following bisulfite treatment, whereby cytosine residues have been converted to uracil residues. In some cases, the reaction mixture further comprises (g) sequencing primers directed against sequences present in the adapter sequence. In some cases, at least one of the sequencing primers is directed against adapter sequence following bisulfite treatment, whereby cytosine residues have been converted to uracil residues and subsequently replaced with thymine residues following amplification XII. Kits Any of the compositions described herein can be comprised in a kit. In a non-limiting example, the kit, in a suitable container, comprises: an adapter or several adapters, one or more of oligonucleotide primers and reagents for ligation, primer extension and amplification. The kit can also comprise means for purification, such as a bead suspension, and nucleic acid modifying enzymes.

The containers of the kits will generally include at least one vial, test tube, flask, bottle, syringe or other containers, into which a component can be placed, and, suitably aliquotted. Where there is more than one component in the kit, the kit also will generally contain a second, third or other additional container into which the additional components can be separately placed. However, various combinations of components can be comprised in a container.

When the components of the kit are provided in one or more liquid solutions, the liquid solution can be an aqueous solution. However, the components of the kit can be provided as dried powder(s). When reagents and/or components are provided as a dry powder, the powder can be reconstituted by the addition of a suitable solvent.

The present methods provide kits containing one or more compositions described herein and other suitable reagents suitable for carrying out the methods described herein. The methods described herein provide, e.g., diagnostic kits for clinical or criminal laboratories, or nucleic acid amplification or analysis kits for general laboratory use. The present methods thus include kits which include some or all of the reagents to carry out the methods described herein, e.g., sample preparation reagents, oligonucleotides, binding molecules, stock solutions, nucleotides, polymerases, enzymes, positive and negative control oligonucleotides and target sequences, test tubes or plates, fragmentation reagents, detection reagents, purification matrices, and an instruction manual. In some cases, the kit comprises a binding molecule, wherein the binding molecule is a nucleotide analog binding protein. In some cases, the nucleotide analog binding protein comprises a methylcytosine binding protein. In some cases, the methylcyotsine binding protein comprises an anti-5-methylcytosine antibody. In some cases, the kit contains a modified nucleotide. Suitable modified nucleotides include any nucleotides provided herein including but not limited to a nucleotide analog. In some cases, the nucleotide analog can be a cytosine analog. In some cases, the cytosine analogs can be 5-methyl dCTP, 5-hydroxymethyl dCTP, and/or 5-propynl dCTP. In some cases, the kit comprises a converting agent. In some cases, the converting agent is bisulfite or its equivalent.

In some cases, the kit can contain one or more reaction mixture components, or one or more mixtures of reaction mixture components. In some cases, the reaction mixture components or mixtures thereof can be provided as concentrated stocks, such as 1.1×, 1.5×, 2×, 2.5×, 3×, 4×, 5×, 6×, 7×, 10×, 15×, 20×, 25×, 33×, 50×, 75×, 100× or higher concentrated stock. The reaction mixture components can include any of the compositions provided herein including but not limited to buffers, salts, divalent cations, azeotropes, chaotropes, dNTPs, labeled nucleotides, modified nucleotides, dyes, fluorophores, biotin, enzymes (such as endonucleases, exonucleases, glycosylases), or any combination thereof.

In some cases, the kit can contain one or more oligonucleotide primers, such as the oligonucleotide primers provided herein. For example, the kit can contain one or more oligonucleotide primers comprising sequence directed against the ligation strand of an adapter or its complement and/or sequence directed against the ligation strand of an adapter or its complement whose sequence is altered by treatment with a converting agent. In some cases, the converting agent is bisulfite. In some cases the kit can contain tailed primers comprising a 3'-portion hybridizable to the target nucleic acid and a 5'-portion which is not hybridizable to the target nucleic acid. In some cases, the kit can contain chimeric primers comprising an RNA portion and a DNA portion. In some cases, the 5' portion of the tailed primers comprises one or more barcode or other identifier sequences. In some cases, the identifier sequences comprises flow cell sequences, TruSeq primer sequence, and/or second read barcode sequences.

In some cases, the kit can contain one or more polymerases or mixtures thereof. In some cases, the one or more polymerases or mixtures thereof can comprise strand displacement activity. Suitable polymerases include any of the polymerases provided herein. The kit can further contain one or more polymerase substrates such as for example dNTPs, non-canonical or modified nucleotides, or nucleotide analogs.

In some cases, the kit can contain one or more means for purification of the nucleic acid products, removing of the fragmented products from the desired products, or combination of the above. Suitable means for the purification of the nucleic acid products include but are not limited to single stranded specific exonucleases, affinity matrices, nucleic acid purification columns, spin columns, ultrafiltration or dialysis reagents, or electrophoresis reagents including but not limited acrylamide or agarose, or any combination thereof.

In some cases, the kit can contain one or more reagents for producing blunt ends. For example, the kit can contain one or more of single stranded DNA specific exonucleases including but not limited to exonuclease 1 or exonuclease 7; a single stranded DNA specific endonucleases such as mung bean exonuclease or S1 exonuclease, one or more polymerases such as for example T4 DNA polymerase or Klenow polymerase, or any mixture thereof. Alternatively, the kit can contain one or more single stranded DNA specific exonucleases, endonucleases and one or more polymerases, wherein the reagents are not provided as a mixture. Additionally, the reagents for producing blunt ends can comprise dNTPs.

In some cases, the kit can contain one or more reagents for preparing the double stranded products for ligation to adapter molecules. For example, the kit can contain dATP, dCTP, dGTP, dTTP, or any mixture thereof. In some cases, the kit can contain a polynucleotide kinase, such as for example T4 polynucleotide kinase. Additionally, the kit can contain a polymerase suitable for producing a 3' extension from the blunt ended double stranded DNA fragments. Suitable polymerases can be included, for example, exo-Klenow polymerase.

In some cases, the kit can contain one or more adapter molecules such as any of the adapter molecules provided herein. Suitable adapter molecules include single or double stranded nucleic acid (DNA or RNA) molecules or derivatives thereof, stem-loop nucleic acid molecules, double stranded molecules comprising one or more single stranded overhangs of 1, 2, 3, 4, 5, 6, 7, 8, 9, 10 bases or longer, proteins, peptides, aptamers, organic molecules, small organic molecules, or any adapter molecules known in the art that can be covalently or non-covalently attached, such as for example by ligation, to the double stranded DNA fragments. In some cases, contains adapters, wherein the adapters can be duplex adapters wherein one strand comprises nucleotide analogs resistant to conversion by a converting agent, while the other strand comprises a 5' and 3' block. In a further embodiment, the duplex adapter is a partial duplex adapter. In some cases, the partial duplex adapter comprises a long strand comprising nucleotide analogs resistant to conversion by a converting agent, and a short strand comprising a 5' and 3' block. In some cases, the nucleotide analog is a cytosine analog. In some cases, the cytosine analogs present in the adapter can be 5-methylcytosine, 5-hydroxymethylcytosine, and/or 5-propynlcytosine. In some cases, the 5' block comprises a biotin moiety. In some cases, the 3' block is blocked with a terminal dideoxycytosine.

In some cases, the kit can contain one or more reagents for performing gap or fill-in repair on the ligation complex formed between the adapters and the double stranded products of the methods described herein. The kit can contain a polymerase suitable for performing gap repair. Suitable polymerases can be included, for example, Taq DNA polymerase.

The kit can further contain instructions for the use of the kit. For example, the kit can contain instructions for generating directional cDNA libraries or directional cDNA libraries representing the methylome or the methylation status of a specific genomic region or locus useful for large scale analysis of including but not limited to e.g., pyrosequencing, sequencing by synthesis, sequencing by hybridization, single molecule sequencing, nanopore sequencing, and sequencing by ligation, high density PCR, digital PCR, massively parallel Q-PCR, and characterizing amplified nucleic acid products generated by the methods described herein, or any combination thereof. The kit can further contain instructions for mixing the one or more reaction mixture components to generate one or more reaction mixtures suitable for the methods described herein. The kit can further contain instructions for hybridizing the one or more oligonucleotide primers to a nucleic acid template. The kit can further contain instructions for extending the one or more oligonucleotide primers with for example a polymerase and/or nucleotide analogs. The kit can further contain instructions for treating the DNA products with a converting agent. In some cases, the converting agent is bisulfite. The kit can further contain instructions for purification of any of the products provided by any of the steps of the methods provided herein. The kit can further contain instructions for producing blunt ended fragments, for example by removing single stranded overhangs or filling in single stranded overhangs, with for example single stranded DNA specific exonucleases, polymerases, or any combination thereof. The kit can further contain instructions for phosphorylating the 5' ends of the double stranded DNA fragments produced by the methods described herein. The kit can further contain instructions for ligating one or more adapter molecules to the double stranded DNA fragments.

A kit will can include instructions for employing, the kit components as well the use of any other reagent not included in the kit. Instructions can include variations that can be implemented.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like. While embodiments have been shown and described herein, it will be obvious to those skilled in the art that such embodiments are provided by way of example only. Numerous variations, changes, and substitutions will now occur to those skilled in the art without departing from the methods, compositions, and kits described herein. It should be understood that various alternatives to the embodiments described herein can be employed. It is intended that the following claims define the scope of the methods, compositions, and kits described herein and that methods and structures within the scope of these claims and their equivalents be covered thereby.

EXAMPLES

Example 1—Generation of a Directional, Bisulfite-Converted NGS Library Using Modified Duplex Adapters This example describes the generation of a directional, bisulfite-converted NGS library from genomic DNA using a single, partial duplex-forming adapter ligated at both ends of each DNA fragment, as depicted in FIG. 1. The long strand of the duplex adapter contains several 5-methylcytosine (5-MeC) residues in place of cytosine residues, which are protected from bisulfite conversion. The short strand of the duplex adapter contains no 5-methylcytosines and does not ligate to the DNA fragment. Consequently, following primer extension and bisulfite treatment, distinct sequences and priming sites are created at each end of the DNA fragments, maintaining directional (strandedness) information of the original DNA sample. An additional feature of the partial duplex adapter is that the 5' and 3' ends of the short strand of the partial duplex adapter are blocked and enzymatically unreactive.

Generation of DNA Fragments with Ligated 5-MeC Adapters

Human female genomic DNA (Promega #G1521) was sheared with a Covaris S-series device using the 200 bp sonication protocol provided with the instrument (10% duty cycle, 200 cycles/burst, 5 intensity, 180 seconds). One microgram of sheared genomic DNA was treated with 1.5 µL 10× Blunting Buffer, 0.5 µL Blunting Enzyme (both from NEB p/n E1201) and 1.2 µL 2.5 mM each dNTP mix in a total volume of 15 µL for 30 minutes at 25° C. followed by 10 minutes at 70° C. A second reaction containing no genomic DNA was also performed as a negative control. After addition of 4.5 µL water, 3 µL Adapter mix (10 µM each of oligonucleotides 147 and 148), 6 µL 5× NEBNext Quick Ligation Reaction Buffer and 1.5 µL Quick T4 DNA Ligase (both from NEB p/n E6056) to each, the reactions were incubated for 30 minutes at 25° C. followed by 10 minutes at 70° C.

Primer Extension and Purification of the Extended DNA Fragments

Next, 23.6 µL water, 2.4 µL 25 mM each dNTP mix, 3 µL 10× PCR Buffer and 1 µL Taq-B DNA Polymerase (both from Enzymatics p/n P725L) were added and the reaction was incubated for 10 minutes at 70° C. Purification of the DNA was accomplished by adding 1.5 volumes of Ampure XP beads (Agencourt Genomics), washing twice with 70% ethanol and eluting with 100 µL of 10 mM Tris pH 8.0.

Bisulfite Conversion, Amplification and Purification of the Library

Ten microliters of purified library was bisulfite converted with the EpiTect Bisulfite Kit (Qiagen p/n 59104) according to the supplied instructions and eluted in a total of 40 µL. Libraries were amplified in 1× MyTaq Reaction Buffer and 0.05 Units/µL MyTaqHS DNA Polymerase (Bioline p/n BIO-21111) with primers 11 and 142 (1 µM each), and supplemented with 1× EvaGreen (Biotium p/n 31000) when real-time PCR was performed. Cycling conditions were 95° C. for 3 minutes followed by 12 cycles (30 cycles for realtime analysis) of 95° C. for 15 seconds, 60° C. for 60 seconds, and 72° C. for 30 seconds. PCR amplified library was purified with the QIAquick PCR Purification Kit (Qiagen p/n 28104) according to the supplied instructions and eluted in 60 µL. Library concentration was determined using the KAPA Library Quantification Kit (KAPA Biosystems p/n KK4835) according to the supplied instructions.

Sequencing and Data Analysis

The library was mixed with PhiX control library and sequenced in single end format 40 nt reads on an Illumina Genome Analyzer IIx instrument. Raw data were processed using Illumina base calling software and reads were analyzed with Bismark software (see Krueger and Andrews, Bioinformatics 27(11): 1571-1572, 2011).

Oligonucleotide Sequences

The oligonucleotide sequences listed below correspond to the adapter and primer sequences of Example 1. Underlined cytosines (c) indicate replacement of unmodified cytosines with 5-methylcytosine (5-MeC). Other modifications are indicated as follows: 5Biosg; 5'biotinylation, and 3ddc; 3' dideoxycytosine.

11:
(SEQ ID NO: 1)
aat gat acg gcg acc acc gag atc tac act ctt tcc cta cac cac gac gct ctt ccg at 142:
(SEQ ID NO: 2)
aag cag aag acg gca tac gag atg tga ctg gag ttc aga cgt gtg ctc ttc cga tct aca ctc tct ccc tac aca aca ctc ctc caa cct 147:
(SEQ ID NO: 3)
tac act ctc tcc cta cac gac gct cct ccg acc t 148:
(SEQ ID NO: 4)
5Biosg/agg tcg gag gag/3ddc

Example 2—Generation of a Directional, Bisulfite-Converted NGS Library Using Modified Duplex Adapters Generation of DNA Fragments with Ligated 5-MeC Adapters
Genomic DNA was sheared with a Covaris S-series device using the 200 bp sonication protocol provided with the instrument (10% duty cycle, 200 cycles/burst, 5 intensity, 180 seconds). DNA was treated with 1.5 µL 10× Blunting Buffer, 0.5 µL Blunting Enzyme (both from NEB p/n E1201) and 1.2 µL 2.5 mM each dNTP mix in a total volume of 15 µL for 30 minutes at 25° C. followed by 10 minutes at 70° C. After addition of 4.5 µL water, 3 µL Adapter mix (10 uM each oligos 227 and 228), 6 µL 5× NEBNext Quick Ligation Reaction Buffer and 1.5 µL Quick T4 DNA Ligase (both from NEB p/n E6056) to each, the reactions were incubated for 30 minutes at 25° C. followed by 10 minutes at 70° C.

Primer Extension and Purification of the Extended DNA Fragments
Next, 17.1 µL water, 1.88 µL 25 mM each dNTP mix, and 1 µL Taq-B DNA Polymerase (both from Enzymatics p/n P725L) were added and the reaction was incubated for 10 minutes at 70° C. Purification of the DNA was accomplished by adding 1.5 volumes of Ampure XP beads (Agencourt Genomics), washing twice with 70% ethanol and eluting with 22 µL of 10 mM Tris pH 8.0.

Bisulfite Conversion, Amplification and Purification of the Library
Twenty microliters of purified library was bisulfite converted with the EpiTect Bisulfite Kit (Qiagen p/n 59104) according to the supplied instructions and eluted in a total of 40 µL. Libraries were amplified in 1× MyTaq Reaction Buffer and 0.05 Units/µL MyTaqHS DNA Polymerase (Bioline p/n BIO-21111) with primers 229 and 232 (1 µM each). Cycling conditions were 95° C. for 3 minutes followed by 14 of 95° C. for 15 seconds, 60° C. for 60 seconds, and 72° C. for 30 seconds. PCR amplified library was purified by adding 1.2 volumes of Ampure XP beads (Agencourt Genomics), washing twice with 70% ethanol and drying. Beads were resuspended in 25 µL 10 mM Tris pH 8. Library concentration was determined using the KAPA Library Quantification Kit (KAPA Biosystems p/n KK4835) according to the supplied instructions Sequencing and Data Analysis
The library was sequenced in single end format 40 nt reads on an Illumina Genome Analyzer IIx instrument using Read 1 sequencing primer 235 and TruSeq Index sequencing primer. Raw data were processed using Illumina base calling software and reads were analyzed with Bismark.

Oligonucleotides Sequences
The oligonucleotide sequences listed below correspond to the adapter and primer sequences of Example 2. Underlined cytosine residues (c) indicate replacement of unmodified cytosines with 5-methylcytosine (5-MeC). Other modifications are indicated as follows: 5Biosg; 5'biotinylation, and 3ddc; 3' dideoxycytosine.

227:
(SEQ ID NO: 5)
gtg acc gga gtc cag acg tgc gct cct ccg atc c

228:
(SEQ ID NO: 6)
5Biosg/gga tcg gag gag/3ddc

229:
(SEQ ID NO: 7)
aat gat acg gcg acc acc gag atc tac aca taa cca aaa tcc aaa cat aca ctc ctc ca 232:
(SEQ ID NO: 8)
caa gca gaa gac ggc ata cga gat gtg act gga gtt cag acg tgt gct ct 235:
(SEQ ID NO: 9)
ata acc aaa atc caa aca tac act cct cca atc c

Example 3—Generation of a Directional, Bisulfite-Converted NGS Library Using Unmodified Duplex Adapters and Adapter Extension in the Presence of 5-Methyl dCTP This example describes the generation of a directional, bisulfite-converted NGS library from genomic DNA using a partial duplex-forming adapter with no modified cytosines but instead performing the adapter extension step in the presence of 5-methyl dCTP, as depicted in FIG. 2. As with Examples 1 and 2, the 5' and 3' ends of the short strand of the partial duplex adapter are blocked and enzymatically unreactive.

Generation of DNA Fragments with Ligated Adapters
Genomic DNA was sheared with a Covaris S-series device using the 200 bp sonication protocol provided with the instrument (10% duty cycle, 200 cycles/burst, 5 intensity, 180 seconds). DNA was treated with 1.5 µL 10× Blunting Buffer, 0.5 µL Blunting Enzyme (both from NEB p/n E1201) and 1.2 µL 2.5 mM each dNTP mix in a total volume of 15 µL for 30 minutes at 25° C. followed by 10 minutes at 70° C. After addition of 4.5 µL water, 3 µL Adapter mix (10 µM each of oligonucleotides 38 and 242-249, depending on desired index), 6 µL 5× NEBNext Quick Ligation Reaction Buffer and 1.5 µL Quick T4 DNA Ligase (both from NEB p/n E6056) to each, the reactions were incubated for 30 minutes at 25° C. followed by 10 minutes at 70° C.

Purification of the DNA Fragments and Extension Reaction Using dNTP Mix Containing 5-MeC
Purification of the DNA was accomplished by adding 1.5 volumes of Ampure XP beads (Agencourt Genomics), washing twice with 70% ethanol and drying. Beads were resuspended in 22 µL of fill-in reagent [19.4 µL water, 2 µL 10× PCR Buffer and 0.4 µL Taq-B DNA Polymerase (both from Enzymatics p/n P725L), and 0.2 μL 10 mM 5-Methylcytosine dNTP Mix (Zymo Research p/n D1030)] for 5 minutes, then removed with a magnet. Supernatant (20 μL) was incubated at 70° C. for 10 minutes.

Bisulfite Conversion, Amplification and Purification of the Library

Supernatant was then subjected to bisulfite conversion with the EpiTect Bisulfite Kit (Qiagen p/n 59104) according to the supplied instructions and eluted in a total of 40 μL. Alternatively, resuspended libraries were pooled prior to bisulfite conversion. Libraries were amplified in 1× MyTaq Reaction Buffer and 0.05 Units/μL MyTaqHS DNA Polymerase (Bioline p/n BIO-21111) with primers 193 and 237 (1 μM each). Cycling conditions were 95° C. for 3 minutes followed by 14 cycles of 95° C. for 15 seconds, 60° C. for 60 seconds, and 72° C. for 30 seconds. PCR amplified library was purified by adding 1.2 volumes of Ampure XP beads (Agencourt Genomics), washing twice with 70% ethanol and drying. Beads were resuspended in 25 μL 10 mM Tris pH 8. Library concentration was determined using the KAPA Library Quantification Kit (KAPA Biosystems p/n KK4835) according to the supplied instructions.

Sequencing and Data Analysis

The library was mixed with PhiX control library and sequenced in single end format 40 nt reads on an Illumina Genome Analyzer IIx instrument using Read 1 sequencing primer 241 and TruSeq Index sequencing primer. Raw data were processed using Illumina base calling software and reads were analyzed with Bismark.

Oligonucleotides Sequences

The oligonucleotide sequences listed below correspond to the adapter and primer sequences of Example 3. Modifications are indicated as follows: 5Biosg; 5'biotinylation, and 3ddc; 3' dideoxycytosine.

38:
(SEQ ID NO: 10)
5Biosg/aga tcg gaa gag/3ddC

193:
(SEQ ID NO: 11)
caa gca gaa gac ggc ata cga

237:
(SEQ ID NO: 12)
att gat acg gcg acc acc gag atc tac tac acg tga ttg gag ttt aga tgt gtg ttt ttt tga t 241:
(SEQ ID NO: 13)
cca cgc aga tct aca cgt gat tgg agt tta gat gtg tgt ttt ttt gat tt 242:
(SEQ ID NO: 14)
caa gca gaa gac ggc ata cga gat tcc ctt gtg act gga gtt cag acg tgt cgt ctt ccg atc t 243:
(SEQ ID NO: 15)
caa gca gaa gac ggc ata cga gat tga agg gtg act gga gtt cag acg tgt gct ctt 244:
(SEQ ID NO: 16)
caa gca gaa gac ggc ata cga gat ggg tcc gtg act gga gtt cag acg tgt gct ctt ccg atc t 245:
(SEQ ID NO: 17)
caa gca gaa gac ggc ata cga gat gct gaa gtg act gga gtt cag acg tgt gct ctt ccg atc t 246:
(SEQ ID NO: 18)
caa gca gaa gac ggc ata cga gat cgt ctt gtg act gga gtt cag acg tgt gct ctt ccg atc t 247:
(SEQ ID NO: 19)
caa gca gaa gac ggc ata cga gat ccg agg gtg act gga gtt cag acg tgt gct ctt ccg atc t 248:
(SEQ ID NO: 20)
caa gca gaa gac ggc ata cga gat aca tcc gtg act gga gtt cag acg tgt gct ctt ccg atc t 249:
(SEQ ID NO: 21)
caa gca gaa gac ggc ata cga gat agc gaa gtg act gga gtt cag acg tgt gct ctt ccg atc t

---

What is claimed is:

1. A method for generating a nucleic acid library, the method comprising:
   ligating first strands of oligonucleotide adapters of similar construct to 5' ends of double-stranded DNA fragments in a sample, wherein the first strand of each adapter comprises one or more guanine;
   extending 3' ends of the double-stranded DNA fragments with a DNA polymerase in the presence of a dCTP analog resistant to bisulfite treatment, thereby creating extension products comprising one or more cytosines resistant to bisulfite treatment and complementary to the guanines;
   treating the extension products with bisulfite, thereby converting unmodified cytosines bases in the DNA fragments and adapter sequences to uracil; and
   amplifying the bisulfite-treated extension products.

2. The method of claim 1, wherein prior to treating the extension product with bisulfite, the extension product is denatured.

3. The method of claim 2, wherein the denaturing step generates a single-stranded DNA fragment comprising the sequence of a first strand of a ligated adapter at the 5' end and a sequence complementary to a first strand of a ligated adapter at the 3' end.

4. The method of claim 3, wherein the oligonucleotide adapters have the same sequence.

5. The method of claim 4, wherein the amplifying step includes contacting the bisulfite treated extension products with a first primer, wherein the first primer is directed against a sequence complementary to the first strand of the adapters which comprise uracil bases following the bisulfite treatment.

6. The method of claim 5, wherein the amplifying step further includes contacting the bisulfite treated extension products with a second primer, wherein the second primer is directed against a sequence complementary to the first strand of the adapters.

7. The method of claim 6, wherein the first and/or second primer comprise a barcode sequence.

8. The method of claim 7, wherein the first and/or second primer comprise a non-hybridizable tail.

9. The method of claim 8, wherein the non-hybridizable tail comprises the barcode sequence, a flow cell sequence, and/or an index sequence.

10. The method of claim 9, wherein the index sequence is a primer sequence compatible with a next generation sequencing platform.

11. The method of claim 1, further comprising sequencing amplicons of the amplified bisulfite-treated extension products.

12. The method of claim 1, wherein the adapters are duplex adapters.

13. The method of claim 12, wherein the adapters comprise a second strand that is incapable of ligation to the 3' end of the double-stranded DNA fragments.

14. The method of claim 13, wherein a 5' end of the second strand comprises a biotin moiety.

15. The method of claim 13, wherein a 3' end of the second strand comprises a terminal dideoxycytosine.

16. The method of claim 1, wherein the adapters are partial duplex adapters, wherein each adapter comprises the first strand and a second strand.

17. The method of claim 16, wherein a long strand of the partial duplex is the first strand and a shorter strand of the partial duplex is the second strand.

18. The method of claim 1, wherein the dCTP analog resistant to bisulfite treatment is 5-methyl dCTP, 5-hydroxymethyl dCTP, or 5-propynyl dCTP.

19. The method of claim 1, further comprising before the bisulfite treatment, performing methylcytosine capture, wherein the dCTP analog is a cytosine analog other than 5-methyl dCTP.

20. The method of claim 19, wherein the methylcytosine capture is performed using a methylcytosine binding protein or an anti-methylcytosine antibody.

\* \* \* \* \*

SEQUENCE LISTING

<160> NUMBER OF SEQ ID NOS: 21

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aatgatacgg cgaccaccga gatctacact ctttccctac accacgacgc tcttccgat      59

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
aagcagaaga cggcatacga gatgtgactg gagttcagac gtgtgctctt ccgatctaca    60
ctctctccct acacaacact cctccaacct                                     90

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methylcytosine
<220> FEATURE:
<221> NAME/KEY: modified_base
<222> LOCATION: (5)..(5)
<223> OTHER INFORMATION: 5-methylcytosine
<220> FEATURE:
<221> NAME/KEY: modified_base
<222> LOCATION: (7)..(7)
<223> OTHER INFORMATION: 5-methylcytosine
<220> FEATURE:
<221> NAME/KEY: modified_base
<222> LOCATION: (11)..(13)
<223> OTHER INFORMATION: 5-methylcytosine
<220> FEATURE:
<221> NAME/KEY: modified_base
<222> LOCATION: (16)..(16)
<223> OTHER INFORMATION: 5-methylcytosine
<220> FEATURE:
<221> NAME/KEY: modified_base
<222> LOCATION: (18)..(18)
<223> OTHER INFORMATION: 5-methylcytosine
<220> FEATURE:
<221> NAME/KEY: modified_base
<222> LOCATION: (21)..(21)
<223> OTHER INFORMATION: 5-methylcytosine
<220> FEATURE:
<221> NAME/KEY: modified_base
<222> LOCATION: (23)..(23)
<223> OTHER INFORMATION: 5-methylcytosine
<220> FEATURE:
<221> NAME/KEY: modified_base
<222> LOCATION: (25)..(25)
<223> OTHER INFORMATION: 5-methylcytosine
<220> FEATURE:
<221> NAME/KEY: modified_base
<222> LOCATION: (28)..(29)
<223> OTHER INFORMATION: 5-methylcytosine
<220> FEATURE:
<221> NAME/KEY: modified_base
<222> LOCATION: (33)..(33)
<223> OTHER INFORMATION: 5-methylcytosine

<400> SEQUENCE: 3
tacactctct ccctacacga cgctcctccg acct                                34

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: 5'-biotin
<222> LOCATION: (1)..(1)
<223> OTHER INFORMATION: 5'-biotin
<220> FEATURE:
<221> NAME/KEY: modified_base
<222> LOCATION: (14)..(14)
<223> OTHER INFORMATION: dideoxycytosine

```
<400> SEQUENCE: 4
gaggtcggag gagc                                                    14

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 5-methylcytosine
<220> FEATURE:
<221> NAME/KEY: modified_base
<222> LOCATION: (13)..(13)
<223> OTHER INFORMATION: 5-methylcytosine
<220> FEATURE:
<221> NAME/KEY: modified_base
<222> LOCATION: (17)..(17)
<223> OTHER INFORMATION: 5-methylcytosine
<220> FEATURE:
<221> NAME/KEY: modified_base
<222> LOCATION: (23)..(23)
<223> OTHER INFORMATION: 5-methylcytosine
<220> FEATURE:
<221> NAME/KEY: modified_base
<222> LOCATION: (25)..(25)
<223> OTHER INFORMATION: 5-methylcytosine
<220> FEATURE:
<221> NAME/KEY: modified_base
<222> LOCATION: (28)..(29)
<223> OTHER INFORMATION: 5-methylcytosine
<220> FEATURE:
<221> NAME/KEY: modified_base
<222> LOCATION: (33)..(33)
<223> OTHER INFORMATION: 5-methylcytosine

<400> SEQUENCE: 5
gtgaccggag tccagacgtg cgctcctccg atcc                              34

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: 5'-biotin
<222> LOCATION: (1)..(1)
<223> OTHER INFORMATION: 5'-biotin
<220> FEATURE:
<221> NAME/KEY: modified_base
<222> LOCATION: (14)..(14)
<223> OTHER INFORMATION: dideoxycytosine

<400> SEQUENCE: 6
gggatcggag gagc                                                    14

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgatacgg cgaccaccga gatctacaca taaccaaaat ccaaacatac actcctcca   59
```

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagcagaag acggcatacg agatgtgact ggagttcaga cgtgtgctct                50

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ataaccaaaa tccaaacata cactcctcca atcc                                 34

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: 5'-biotin
<222> LOCATION: (1)..(1)
<223> OTHER INFORMATION: 5'-biotin
<220> FEATURE:
<221> NAME/KEY: modified_base
<222> LOCATION: (14)..(14)
<223> OTHER INFORMATION: dideoxycytosine

<400> SEQUENCE: 10
gagatcggaa gagc                                                       14

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagcagaag acggcatacg a                                               21

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
attgatacgg cgaccaccga gatctactac acgtgattgg agtttagatg tgtgtttttt     60
tgat                                                                  64

<210> SEQ ID NO 13
<211> LENGTH: 50
<212> TYPE: DNA

<213> ORGANISM: Artificial Sequence
<220> FEATURE:
<223> OTHER INFORMATION: Description of Artificial Sequence: Synthetic primer

<400> SEQUENCE: 13
ccacgcagat ctacacgtga ttggagttta gatgtgtgtt tttttgattt    50

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
caagcagaag acggcatacg agattcccctt gtgactggag ttcagacgtg tcgtcttccg    60
atct    64

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
caagcagaag acggcatacg agattgaagg gtgactggag ttcagacgtg tgctctt    57

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
caagcagaag acggcatacg agatgggtcc gtgactggag ttcagacgtg tgctcttccg    60
atct    64

<210> SEQ ID NO 17
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
caagcagaag acggcatacg agatgctgaa gtgactggag ttcagacgtg tgctcttccg    60
atct    64

<210> SEQ ID NO 18
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
caagcagaag acggcatacg agatcgtctt gtgactggag ttcagacgtg tgctcttccg    60

```
atct                                                                    64

<210> SEQ ID NO 19
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caagcagaag acggcatacg agatccgagg gtgactggag ttcagacgtg tgctcttccg       60
atct                                                                    64

<210> SEQ ID NO 20
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caagcagaag acggcatacg agatacatcc gtgactggag ttcagacgtg tgctcttccg       60
atct                                                                    64

<210> SEQ ID NO 21
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
caagcagaag acggcatacg agatagcgaa gtgactggag ttcagacgtg tgctcttccg       60
atct                                                                    64
```